(12) United States Patent
O'Donnell

(10) Patent No.: US 9,233,076 B2
(45) Date of Patent: Jan. 12, 2016

(54) CONTROLLED RELEASE DOSAGE FORMS

(75) Inventor: Edward O'Donnell, Basking Ridge, NJ (US)

(73) Assignee: Purdue Pharma L.P., Stamford, CT (US)

( * ) Notice: Subject to any disclaimer, the term of this patent is extended or adjusted under 35 U.S.C. 154(b) by 28 days.

(21) Appl. No.: 13/880,841

(22) PCT Filed: Dec. 12, 2011

(86) PCT No.: PCT/IB2011/003139
§ 371 (c)(1),
(2), (4) Date: Apr. 22, 2013

(87) PCT Pub. No.: WO2012/080833
PCT Pub. Date: Jun. 21, 2012

(65) Prior Publication Data
US 2013/0259941 A1    Oct. 3, 2013

Related U.S. Application Data

(60) Provisional application No. 61/422,512, filed on Dec. 13, 2010.

(51) Int. Cl.
| A61K 9/50 | (2006.01) |
| A61K 9/20 | (2006.01) |
| A61K 9/28 | (2006.01) |
| A61K 31/485 | (2006.01) |

(52) U.S. Cl.
CPC .............. *A61K 9/50* (2013.01); *A61K 9/2072* (2013.01); *A61K 9/2846* (2013.01); *A61K 9/2866* (2013.01); *A61K 31/485* (2013.01); *A61K 9/2031* (2013.01)

(58) Field of Classification Search
CPC . A61K 9/2866; A61K 9/4891; A61K 9/2846; A61K 9/0004; A61K 9/2072; A61K 9/4808; A61K 9/2031; A61K 9/5026; A61K 9/2081; A61K 9/5042; A61K 31/485; A61K 9/0053; A61K 9/2086; A61K 9/50; A61K 9/5089; A61K 9/2077
See application file for complete search history.

(56) References Cited

U.S. PATENT DOCUMENTS

| 4,218,433 A | 8/1980 | Kooichi et al. |
| 4,609,374 A | 9/1986 | Ayer |
| 4,806,337 A | 2/1989 | Snipes et al. |

(Continued)

FOREIGN PATENT DOCUMENTS

| EP | 0 542 364 | 10/1993 |
| EP | 0 631 781 | 1/1995 |

(Continued)

OTHER PUBLICATIONS

The International Search Report and the Written Opinion of the International Searching Authority issued on Jul. 10, 2012, in connection with International Application No. PCT/IB2011/003139.

(Continued)

*Primary Examiner* — Isis Ghali
(74) *Attorney, Agent, or Firm* — Davidson, Davidson & Kappel, LLC

(57) ABSTRACT

Dosage forms having a core having a surface having means for controlling release(s) on an active agent(s); methods of manufacturing, tools used in manufacturing; and uses of the dosage forms are described.

19 Claims, 37 Drawing Sheets

(56) References Cited

U.S. PATENT DOCUMENTS

| | | |
|---|---|---|
| 4,839,177 A | 6/1989 | Colombo et al. |
| 5,004,614 A | 4/1991 | Staniforth |
| 5,256,440 A | 10/1993 | Appel et al. |
| 5,391,378 A | 2/1995 | Sanderson |
| 5,464,633 A | 11/1995 | Conte et al. |
| 5,534,263 A | 7/1996 | Wong et al. |
| 5,902,598 A | 5/1999 | Chen et al. |
| 5,945,125 A | 8/1999 | Kim |
| 6,264,985 B1 | 7/2001 | Cremer |
| 6,488,962 B1 | 12/2002 | Berner et al. |
| 6,514,530 B2 | 2/2003 | Skluzacek et al. |
| 7,195,778 B2 | 3/2007 | Fleshner-Barak et al. |
| 7,300,668 B2 | 11/2007 | Pryce Lewis et al. |
| 7,416,738 B2 | 8/2008 | Sowden et al. |
| 2002/0119197 A1 | 8/2002 | Dyar et al. |
| 2004/0005360 A1 | 1/2004 | Wang et al. |
| 2004/0022852 A1 | 2/2004 | Chopra |
| 2004/0146559 A1 | 7/2004 | Sowden et al. |
| 2007/0264331 A1 | 11/2007 | Regalado et al. |
| 2009/0081290 A1 | 3/2009 | McKenna et al. |
| 2009/0258039 A1 | 10/2009 | Bunick et al. |
| 2010/0151020 A1 | 6/2010 | Rosenberger et al. |

FOREIGN PATENT DOCUMENTS

| | | |
|---|---|---|
| EP | 1 915 988 | 4/2008 |
| WO | 2004/093843 | 11/2004 |
| WO | WO 2008106429 A2 * | 9/2008 |
| WO | 2010/060564 | 6/2010 |

OTHER PUBLICATIONS

Liu, "Preparation of bilayer-core osmotic pump tablet by coating the indented core tablet", Science Direct, International Journal of Pharmaceutics, College of Pharmaceutics, Zhejiang University, Hangzhou 310058, PR China, Mar. 4, 2007.

Pictures of Bottle Caps Candy, Nov. 2011.

Tableting Specification Manual, Sixth Edition, American Pharmaceutical Association, Washington, D.C., 2003.

International Preliminary Report on Patentability issued on Jun. 27, 2013, in connection with International Application No. PCT/IB2011/003139.

* cited by examiner

CONTROLLED RELEASE DOSAGE FORMS

TECHNICAL FIELD OF THE INVENTION

The present invention relates to a controlled release dosage form, a method of altering the release and a method of manufacturing the controlled release dosage form and uses thereof.

BACKGROUND OF THE INVENTION

Over the years, various drugs have been developed to assist in treatment of a wide variety of ailments and diseases. Various dosage forms for providing a release of drugs at a controlled release rate were also developed. There however remains an unfilled need for simple and reliable controlled release dosage forms that release active agents at predetermined times, predetermined release rates, and for predetermined duration, which dosage forms can be manufactured with relative ease and at an acceptable cost. Controlled release coatings, in particular prolonged release coatings are used to provide a specific release profile of the active contained in a core surrounded by such coatings. In order to ensure the target release profile the coating is prepared such that it provides the target release and that a rupture of the coating during the release is avoided. Typically the target release is achieved by including plasticizers and/or pore formers in the coating system to control drug diffusion through the coating.

SUMMARY OF THE INVENTION

In contrast to the prior art, the invention aims at deliberately preparing a core with a controlled release coating in such a way that the coating ruptures after being placed in an aqueous medium, e.g., simulated gastric fluid (SGF), and provides for said aqueous medium limited direct access to the core. The time and extent of the rupture is controlled in accordance with the invention by the surface topography of the core.

According to certain embodiments the present invention relates to a controlled release dosage form comprising a prolonged release core comprising an active agent and having a surface with at least one structure, said surface being completely coated with a prolonged coating, said coating rupturing after the dosage form is placed in an aqueous medium, e.g., SGF, to provide at least one passageway directly exposing said core to said aqueous medium, wherein the active agent is released from the dosage form for about 6 or more hours. The dosage form preferably comprises a subcoat as part of the core comprising a hydroxypropylmethylcellulose (e.g., Opadry). The coating is between the controlled release coating and the core. The subcoat preferably adheres to the core throughout the perimeter of the dosage form. The uncoated core may provide an immediate or a controlled release/prolonged release of the active agent.

The present invention relates to controlled release dosage forms that release active agents at predetermined times, predetermined release rates, and/or for predetermined duration, and that can be manufactured with conventional processes with relative ease and at an acceptable cost.

A dosage form of the present invention comprises a core having an active agent and a surface having means for controlling the release of the active agent at a predetermined time, predetermined rate and/or for a predetermined duration, wherein the core is coated with a controlled release coating.

The present invention provides for control of the release rate of an active agent from the dosage form by varying the topography of the surface of the core by, e.g., using conventional compression processes, as compared to more complex drug delivery systems (e.g., osmotic pump tablets) or multi-layer systems (e.g., bi-layer or tri-layer tablets). In certain embodiments, the compression is done with punches having punch tip faces that have been specially designed to produce at least one structure (e.g., a peak or indentation, or combination thereof) of predetermined dimensions (e.g., height, width, depth, shape and/or size) on the surface of the core.

The present invention also relates to methods of manufacturing these dosage forms.

The present invention also relates to uses of these dosage forms, e.g., in treatment of medical conditions.

DEFINITIONS

The term "dosage form" means a formulation containing a therapeutically effective amount of an active agent for the prophylaxis or treatment of a medical condition, and does not encompass confectionaries or "sweets" (i.e., candies or gums). In a preferred embodiment, the active agent is a pharmaceutical agent that is or has been the subject of regulatory review by the United States Food and Drug Administration and/or a corresponding regulatory review agency in a foreign jurisdiction. In certain embodiments, the dosage form is not available over-the-counter (i.e., may not be sold directly to a consumer without a prescription from a health care professional), and may only be sold to consumers possessing a valid prescription from a health care professional.

The term "completely coated" in reference to the core of the dosage form means that, when the dosage form is placed in an aqueous medium, the core of the dosage form is not initially exposed to (i.e., not in direct contact with) the aqueous medium, e.g., SGF, because it is separated from the aqueous medium by a coating surrounding the core until the coating ruptures and at least one passageway is formed in the coating at some time after the placement of the dosage form into the aqueous medium.

The phrase "surface with at least one structure," and the like, means that the topography of the surface of the core is not substantially uniform, but has at least one raised portion (e.g., a peak) or indentation which is visibly discernible without the aid of any magnifying equipment, in contrast to the substantially uniform surface of a conventional dosage form (e.g., a conventional tablet or capsule having a smooth surface with a substantially flat, concave or convex shape). The edges created by the band of a conventional tablet are not considered as a structure in accordance with the invention.

The term "controlled release" refers to a release other than immediate release/release of the active agent itself in that the overall release is prolonged. The overall controlled release or prolonged release of the dosage form is provided by all features contributing to the controlled/prolonged release such as the prolonged release coating and the structures on the core and optionally the prolonged release core.

The terms "prolonged release core" or "controlled release core" refer to a core providing as such prolonged release of the active agent contained therein in comparison to immediate release of the active agent and/or the release of the active agent which is not altered to prolong the release beyond the release provided by the active itself. Preferably the prolonged release of the core is provided by a prolonged release matrix. For example an immediate release of the active will refer to a release of at least 80% of the active in 30 minutes.

The terms "prolonged release coating" and "controlled release coating" refer to a coating providing prolonged release of the active agent contained in the core in comparison to the release of the active agent from the core without said coating. In certain embodiments the prolonged release coating itself does substantially not allow any release of the active agent from the core. In such embodiment the release of the active agent from the core may only take place via the one or more passageways formed due to the rupture of the coating. The thickness of the coating is in certain embodiments substantially the same throughout the perimeter of the dosage form so that the structure on the surface of the core is still visible after coating. According to certain embodiments, the structure of the coated core is visually not distinguishable from the structure of the core.

The term "zero order release rate" means that an active agent is released from the dosage form at a substantially constant rate.

For purposes of the present invention, the dissolution rate of the dosage form or release rate of the active agent(s) from the dosage form is measured using the U.S.P. apparatus 1 basket method (10 mesh SS) with spring insert, 900 ml of SGF (simulated gastric fluid), with a rotation speed of 100 rpm at 37° C.

DETAILED DESCRIPTION

Figure 1:
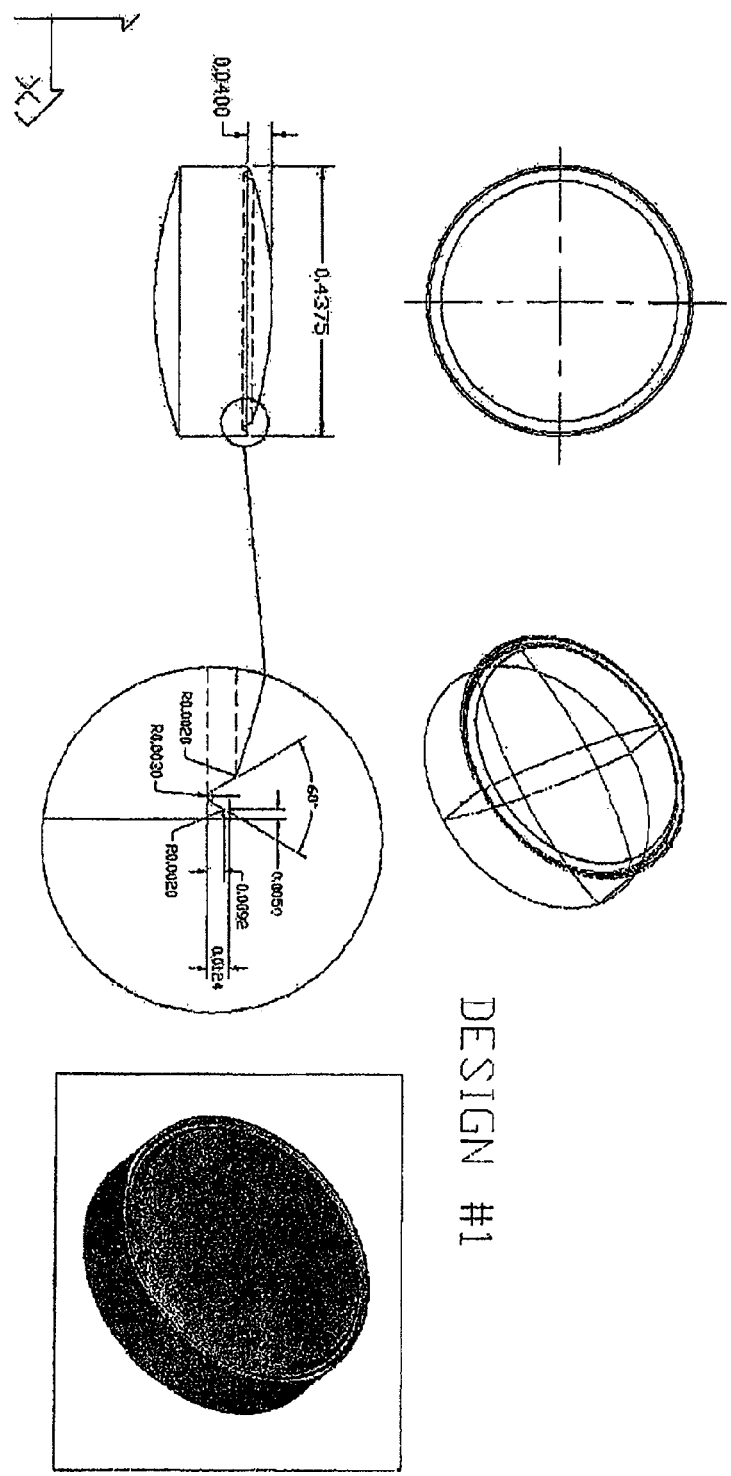
FIG. 1 is a drawing of a tablet core of design 1.
Figure 2:
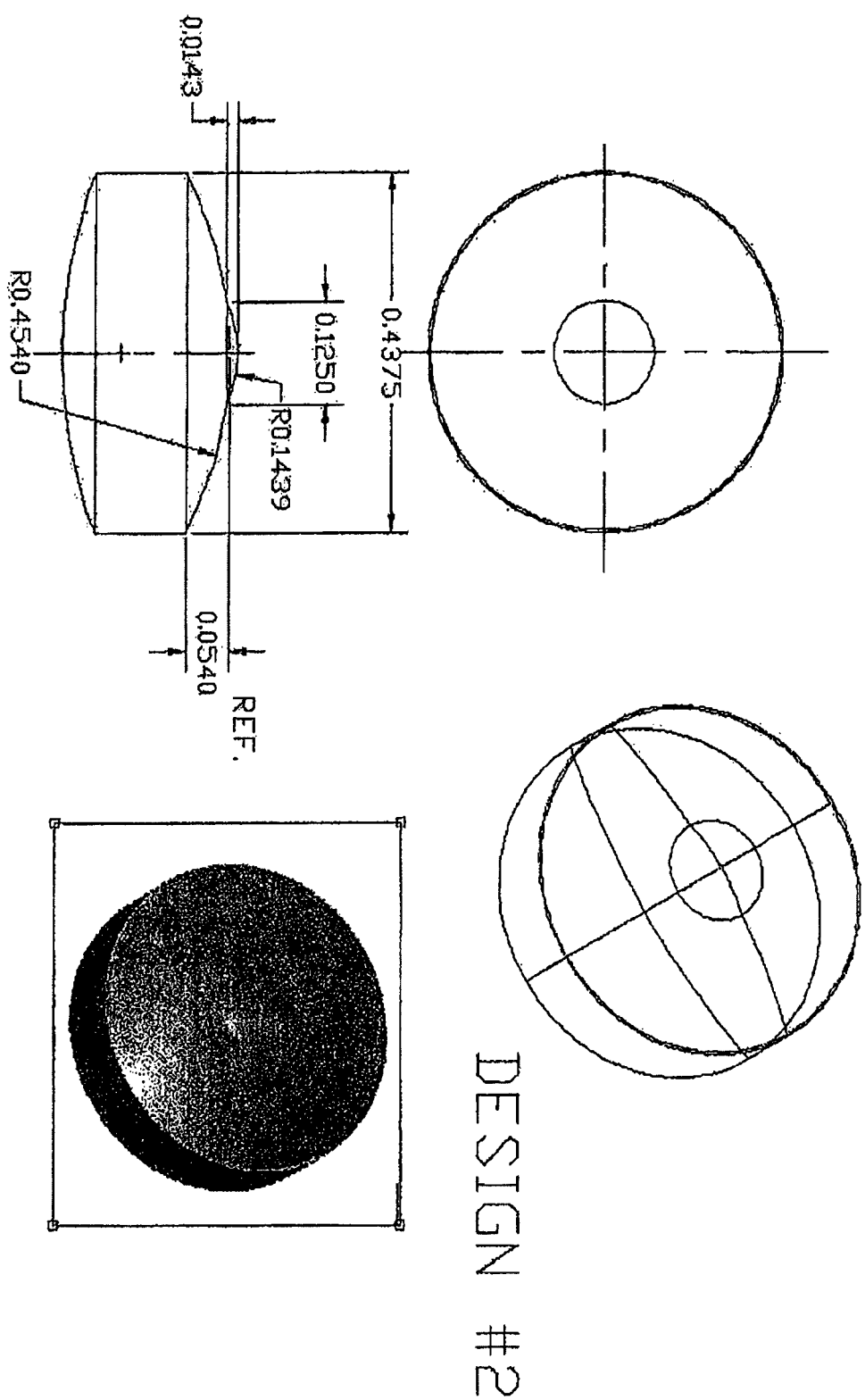
FIG. 2 is a drawing of a tablet core of design 2.
Figure 3:
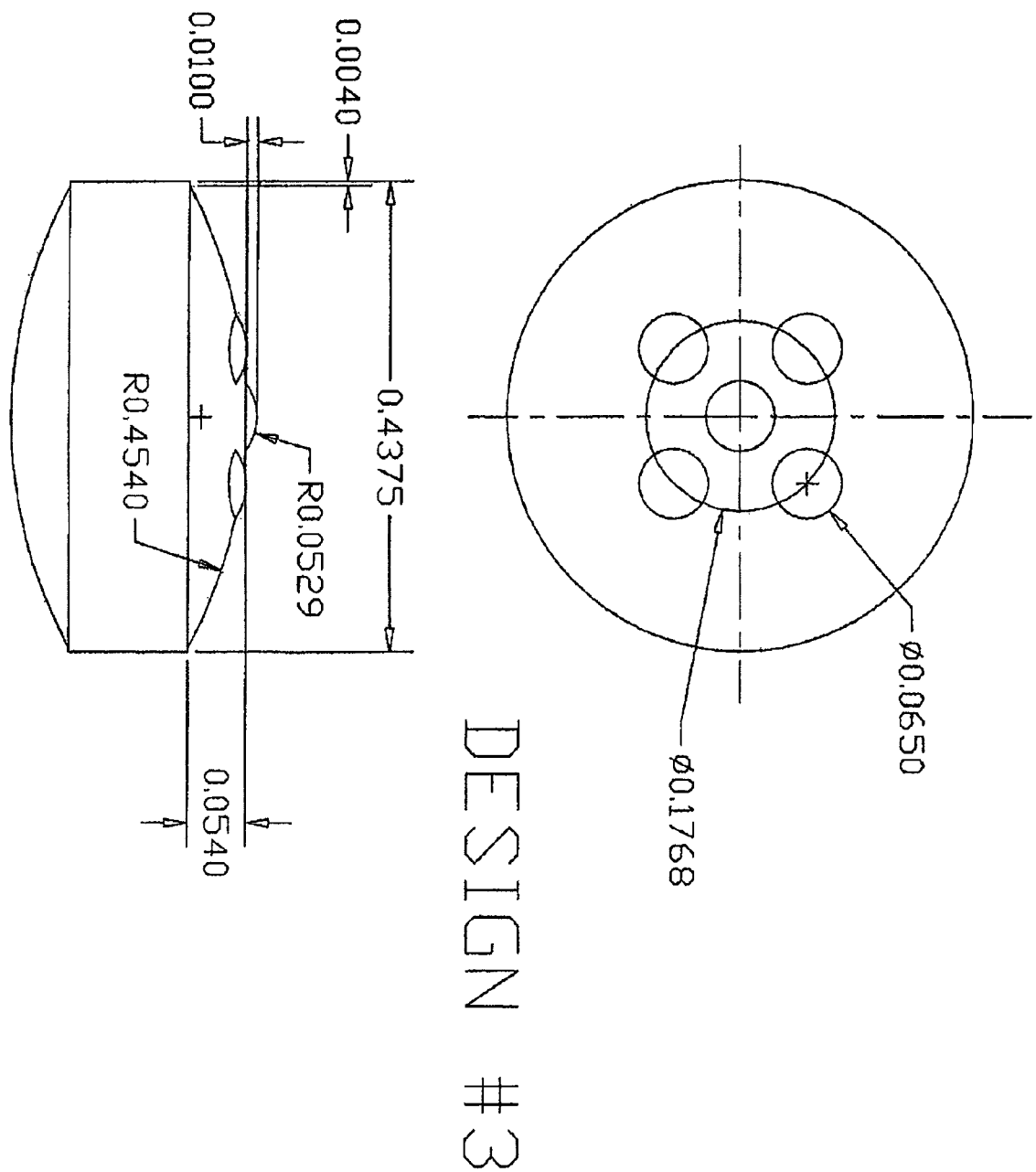
FIG. 3 is a drawing of a tablet core of design 3.
Figure 4:
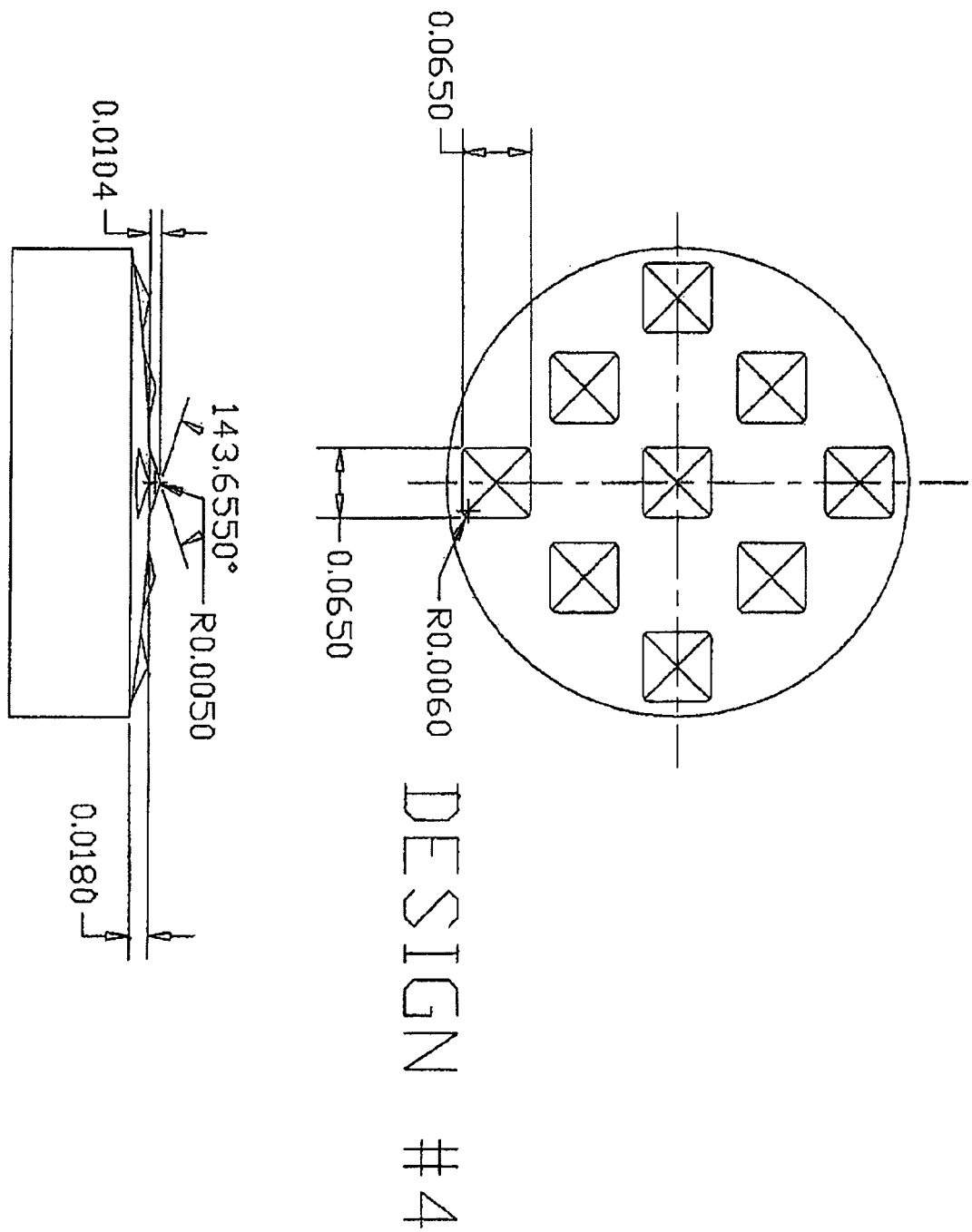
FIG. 4 is a drawing of a tablet core of design 4. There could also be conical round formations instead of squares.
Figure 5:
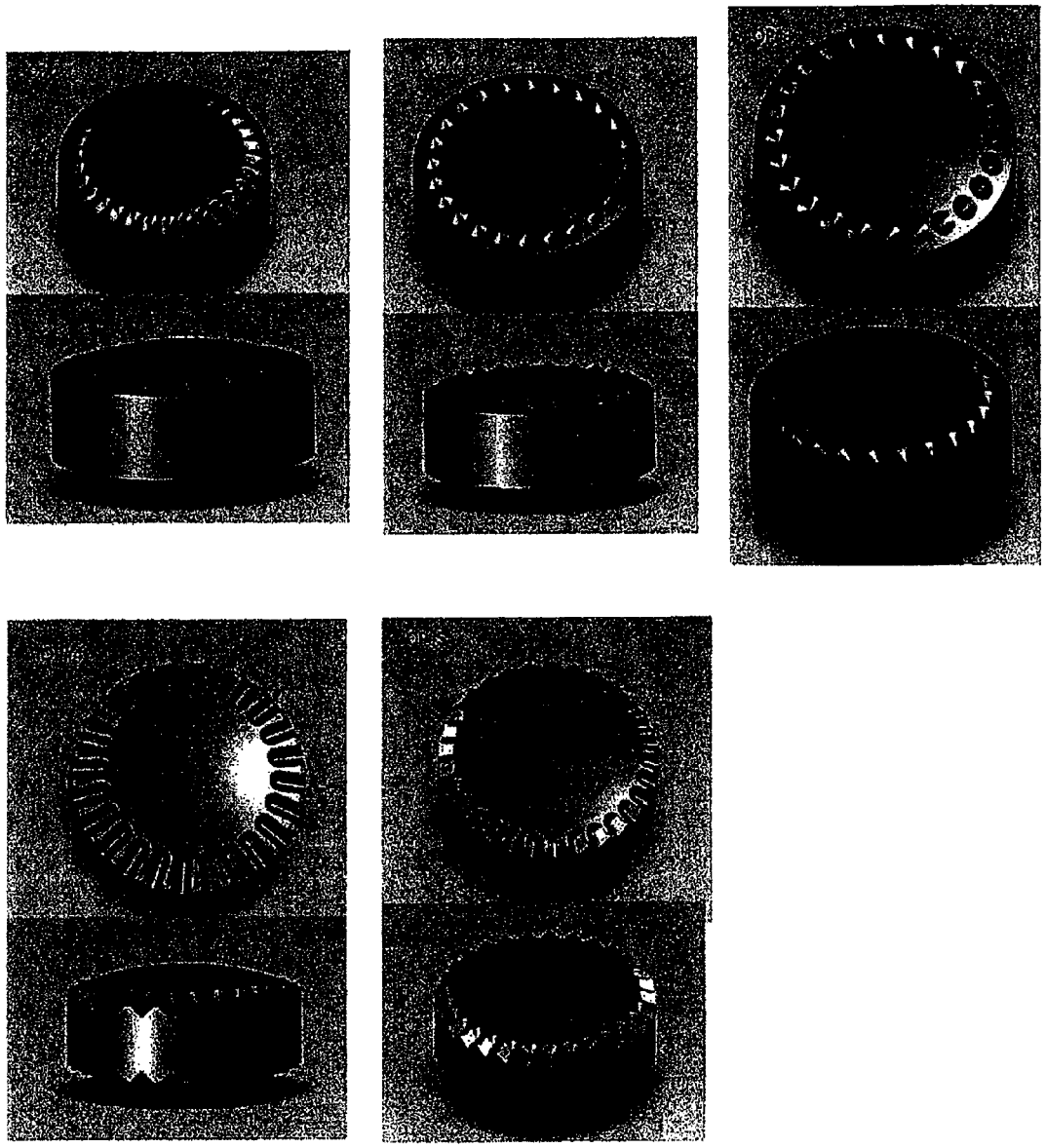
FIG. 5 shows computerized images of tablet cores having surfaces with different structures according to the present invention.

In contrast to the prior art the invention aims at deliberately preparing a core with a controlled release coating in such a way that it ruptures after being placed in an aqueous medium and provides for the aqueous medium limited direct access to the core. By controlling the time and extent of the rupture the release profile is controlled. The time and extent of the release is controlled in accordance with the invention by the surface topography of the core.

An exemplary dosage form in accordance with the present invention comprises a core having an active agent, the core having a surface with means for controlling the release of the active agent at a predetermined time, predetermined rate and/or for a predetermined duration, wherein the core, including the means, is initially completely coated with a coating. The means for controlling the release of the active agent includes one or more topographical structural features on and attached to and/or forming part of the surface of the core.

The means on the surface of the core for controlling the release of the active agent are topographical structural features that function by providing a focal point where the coating proximal to, or immediately above, the means on the dosage form will preferentially rupture, as compared to areas of the coating distal to or not immediately above the means, upon placement of the dosage form in an aqueous medium. In one embodiment, such topographical features are selected from peaks, bumps, mounds, indentations, pits, grooves, serrations, embossments, engravings, imprints, and combinations thereof.

The thickness and composition of the coating, as well as the dimensions (e.g., height, width, depth, shape and/or size) and number of the topographical features on the surface of the core are selected such that upon placement of the coated core (or a dosage form comprising the coated core) into an aqueous medium (e.g., simulated gastric fluid (SGF)), the coating will preferentially rupture at a predetermined time above the features, thereby forming at least one passageway exposing the core to the aqueous medium, and thereby allowing release of the active agent from the core for a predetermined period of time (e.g., 4, 6, 8, 12 or 24 hours) after the coated core is placed into aqueous media.

In certain embodiments, rupture of the coating immediately above or proximal to the means improves structural stability of the dosage form (e.g., by relieving the internal pressure inside the core and preserving the integrity of the portions of the coating which are not immediately above or proximal to the means).

In certain embodiments, rupture of the coating immediately above or proximal to the means controls the rate of release and improves the safety of the dosage form (e.g., by minimizing the risk of the active agent being released too quickly and causing an inadvertent overdose of the active agent).

In certain embodiments, rupture of the coating immediately above or proximal to the means allows for a reduction in the amount of excipients required to provide controlled release of an active agent from the dosage form over a predetermined period of time (e.g., a 12-hour formulation can be processed to provide a 24-hour release profile, while utilizing the same type and amount of excipients as the 12-hour formulation), thereby making the dosage form cheaper to manufacture and smaller in size than it otherwise would need to be. In certain embodiments, this may improve patient compliance as a smaller and longer acting dosage form (e.g., once a day vs. twice a day) is easier to administer.

In other embodiments, the invention is directed to a controlled release dosage form having a core which is (i) coated with a coating and (ii) has a surface with at least one structure (e.g., a peak and/or indentation). The thickness of the coating is generally the same throughout the perimeter of the dosage form. The coating may or may not be a compression coating. The structure(s) disrupts the integrity of the coating in that portion of the coating which is immediately above or proximal to the structure(s), upon placement of the dosage form into an aqueous medium, creating a weak point in the portion of the coating above the structure(s) such that the coating ruptures at the weak point(s) after the coated core (or the dosage form comprising the coated core) is placed in the aqueous medium, forming at least one passageway in the portion of the coating immediately above or proximal to the structure(s), thereby allowing the aqueous medium to enter the core and/or the active agent to be released from the coated core at a controlled rate substantially through the passageway(s), which was (were) not present in the dosage form before the coated core was exposed to the aqueous medium.

In certain embodiments, the invention is directed to a controlled release dosage form comprising a core comprising an active agent and having a surface with one or more structures (e.g., peaks and/or indentations) integral with the surface, wherein the core and the structure(s) are coated with a coating comprising a controlled release material and, preferably, having a thickness which is substantially the same throughout the perimeter of the dosage form, wherein the coating completely covers the core and the structure(s), has at least one weak point in a portion of the coating immediately above or proximal to the structure(s), and ruptures at the weak point(s) at a predetermined time after the coated core (or a dosage form containing the coated core) is placed in an aqueous medium, forming at least one passageway in the portion of the coating immediately above the structure(s), wherein the active agent is released from the dosage form substantially through the passageway(s) at a predetermined rate (e.g., controlled rate) for about 6 or more hours. In certain embodiments, the coating is not a compression coating. In certain embodiments, portions of the coating which are not immediately above or proximal to the structure(s) remain substantially intact and/or adhered to the core for about 6 to 36 hours, about 8 to 24 hours, about 10 to 24 hours, about 12 to 24 hours, or about 8 to 28 hours after the coated core is placed in the aqueous medium.

In further embodiments, the invention is directed to a controlled release dosage form comprising a core comprising an active agent and having a rippled edge, the core and the rippled edge are coated with a coating comprising a controlled release material, wherein the active agent is released from the dosage form substantially through at least one passageway formed in the coating immediately above or proximal to the rippled edge at a predetermined time after the dosage form is placed in an aqueous medium. Preferably, the thickness of the coating is substantially the same throughout the perimeter of the dosage form. The coating may or may not be a compression coating. In certain embodiments, portions of the coating which are not immediately above or proximal to the rippled edge remain substantially intact and/or adhered to the core for about 6 to 36 hours, about 8 to 24 hours, about 10 to 24 hours, about 12 to 24 hours, or about 8 to 28 hours after the dosage form is placed in the aqueous medium.

In additional embodiments, the invention is directed to a controlled release dosage form comprising a core comprising an active agent and having a serrated edge, the core and the serrated edge are coated with a coating comprising a controlled release material, wherein the active agent is released from the coated core (or a dosage form comprising the coated core) substantially through at least one passageway formed in the coating immediately above or proximal to the serrated edge at a predetermined time after the coated core is placed in an aqueous medium. Preferably, the thickness of the coating is substantially the same throughout the perimeter of the dosage form. The coating may or may not be a compression coating. In certain embodiments, portions of the coating which are not immediately above or proximal to the serrated edge remain substantially intact and/or adhered to the core for about 6 to 36 hours, about 8 to 24 hours, about 10 to 24 hours, about 12 to 24 hours, or about 8 to 28 hours after the coated core is placed in the aqueous medium.

In additional embodiments, the invention is directed to a controlled release dosage form comprising (i) a core comprising an active agent, (ii) at least one structure attached to the surface of the core, and (iii) a coating comprising a controlled release material, the core and the structure(s) coated with the coating, the coating having at least one weak point in a portion of the coating immediately above or proximal to the structure(s), and rupturing at the weak point at a predetermined time after the coated core (or the dosage form containing the coated core) is placed in an aqueous medium, forming at least one passageway in the portion of the coating immediately above or proximal to the structure(s), wherein the active agent is released from the coated core substantially through the passageway(s) at a predetermined rate (e.g., controlled rate) for about 6 or more hours. In these embodiments, the structure(s) attached to the core is (are) not formed by the compression of the core, but is (are) attached to the core after the core is formed (e.g., by spraying on the compressed core or by an additional compression). The attached structure(s) may or may not have the same composition as the core. The coating in these embodiments may or may not be a compression coating. The thickness of the coating may or may not be substantially the same throughout the perimeter of the dosage form. The portions of the coating which are not immediately above or proximal to the structure(s) will generally remain substantially intact and/or adhered to the compressed core for about 6 to 36 hours, about 8 to 24 hours, about 10 to 24 hours, about 12 to 24 hours, or about 8 to 28 hours after the dosage form is placed in the aqueous medium.

The invention is also directed to a controlled release dosage form comprising a core comprising an active agent, the core having a surface with at least one structure (e.g., a peak and/or indentation) and coated with a coating comprising a polymer, wherein the active agent is released from the dosage form through at least one passageway formed in the portion of the coating immediately above or proximal to the structure(s) at a predetermined time after the coated core (or a dosage form comprising the coated core) is placed in an aqueous medium, and portions of the coating which are not immediately above or proximal to the structure(s) remain intact and/or adhered to the core for about 8 to 36 hours after the dosage form is placed in the aqueous medium. The polymer in these embodiments is generally a hydrophobic polymer (e.g., ethyl cellulose or an acrylic polymer) or an aqueous dispersion of a hydrophobic polymer (e.g., a neutral copolymer based on ethyl acrylate and methyl methacrylate such as Eudragit NE 30 D). The release rate of the active agent(s) is determined by the number and dimensions (e.g., height, width, depth, shape and/or size) of the structure(s) and the amount of the polymer in the coating and optionally by the core. Portions of the coating which are not immediately above or proximal the structure(s) remain substantially intact for about 6 to 36 hours, about 8 to 24 hours, about 10 to 24 hours, about 12 to 24 hours, or about 8 to 28 hours after the coated core is placed in the aqueous medium. The coating in these embodiments may or may not be a compression coating. The thickness of the coating may or may not be substantially the same throughout the perimeter of the dosage form.

In certain embodiments, the invention is directed to a controlled release dosage form comprising a monolithic core comprising an active agent, the core having a surface with at least one structure (e.g., a peak and/or indentation), the core and the structure(s) coated with a coating comprising a polymer and, optionally, having substantially the same thickness throughout the perimeter of the dosage form, wherein the active agent is released from the dosage form through at least one passageway formed in the portion of the coating immediately above or proximal to the structure(s) at a predetermined time after the dosage form is placed in an aqueous medium. The release rate of the active agent(s) is determined by the number and dimensions (e.g., height, width, depth, shape and/or size) of the structure(s) and the amount and/or composition of the coating. Portions of the coating which are not immediately above or proximal to the structure(s) will remain intact and/or adhered to the core for about 6 to 36 hours, about 8 to 24 hours, about 10 to 24 hours, about 12 to 24 hours, or about 8 to 28 hours after the dosage form is placed in the aqueous medium.

In certain embodiments, the invention is directed to a controlled release dosage form comprising a core having a surface with at least one structure (e.g., a peak and/or indentation), the core comprising an active agent and at least one polyethylene oxide, and coated with a coating having substantially the same or different thickness throughout the perimeter of the dosage form, wherein the active agent is released from the dosage form through at least one passageway formed in the portion of the coating immediately above or proximal to the structure(s) at a predetermined time after the dosage form is placed in an aqueous medium. The release rate of the active agent is determined by the dimensions (e.g., number, height, width, depth, shape and/or size) of the structure(s) and the amount of the polymer in the coating. In these embodiments, portions of the coating which are not immediately above or proximal to the structure(s) will tend to remain intact and/or adhered to the core for about 6 to 36 hours, about 8 to 24 hours, about 10 to 24 hours, about 12 to 24 hours, or about 8 to 28 hours after the dosage form is placed in the aqueous medium.

In certain embodiments, the present invention is directed to a controlled release dosage form comprising a core having a surface with at least one structure (e.g., a peak and/or indentation), the core comprising an active agent dispersed in a matrix of at least one polyethylene oxide, and coated with a coating comprising a polymer, wherein the active agent is released from the dosage form through at least one passageway formed in the portion of the coating immediately above or proximal to the structure(s) at a predetermined time after the dosage form is placed in an aqueous medium. At least one polymer in these embodiments is generally a hydrophobic polymer (e.g., ethyl cellulose or an acrylic polymer) or an aqueous dispersion of a hydrophobic polymer (e.g. a neutral copolymer based on ethyl acrylate and methyl methacrylate such as Eudragit NE 30D®). Portions of the coating which are not immediately above or proximal to the structure(s) will tend to remain substantially intact and/or adhered to the core for about 6 to 36 hours, about 8 to 24 hours, about 10 to 24 hours, about 12 to 24 hours, or about 8 to 28 hours after the dosage form is placed in the aqueous medium. The coating in these embodiments may or may not be a compression coating, and the thickness of the coating may or may not be substantially the same throughout the perimeter of the dosage form.

In certain embodiments, the present invention is directed to a controlled release dosage form comprising a core comprising an active agent, the core having a surface with at least one structure (e.g., a peak and/or indentation), wherein the core is coated with a coating comprising a polymer having substantially the same or different thickness throughout the perimeter of the dosage form, wherein the active agent is released at a zero order release rate from the dosage form through at least one passageway formed in the portion of the coating immediately above or proximal to the structure(s) at a predetermined time for about 8 to 36 hours, about 8 to 24 hours, about 10 to 24 hours, about 12 to 24 hours, or about 8 to 28 hours after the dosage form is placed in the aqueous medium. In certain embodiments, the dosage form releases the active agent at substantially zero order release rate for about 4, 6, 8, 10, 12, 14, 15, 16, 17, 18, 19, 20, 21 or 22 hours after the dosage form is placed into the aqueous medium.

In certain embodiments, the present invention is directed to a controlled release dosage form comprising a core comprising an active agent, the core having a surface having a plurality of structures (e.g., peaks and/or indentations) and coated with a coating comprising a polymer, wherein the active agent is released at a predetermined time, predetermined rate and for a predetermined period of time from the dosage form substantially through a plurality of passageways formed in the coating immediately above or proximal to the structures after the dosage form is placed in an aqueous medium. The release rate of the active agent is determined by the number and dimensions (e.g., height, width, depth, shape and/or size) of the individual structures and the amount of the polymer in the coating. The coating in these embodiments may or may not be a compression coating, and the thickness of the coating may or may not be substantially the same throughout the perimeter of the dosage form.

In certain embodiments, the present invention is directed to a controlled release dosage form comprising a compressed core comprising an active agent and having a surface with at least one structure (e.g., peak and/or indentation), the compressed core coated with a coating, wherein the structure(s), has (have) dimensions (e.g., height, width, depth, shape and/or size) such that, upon placement of the dosage form into an aqueous medium, at least one passageway is formed in the coating immediately above or proximal to the structure(s) at a predetermined time after the dosage form is placed in an aqueous medium, and the active agent is released from the dosage form substantially through the passageway(s) at a controlled release rate for about six or more hours. The coating in these embodiments may or may not be a compression coating, and the thickness of the coating may or may not be substantially the same throughout the perimeter of the dosage form.

In certain embodiments, the present invention is directed to a controlled release dosage form comprising a monolithic core comprising an active agent and having a surface comprising at least one concave or convex structure, the core coated with a coating comprising a polymer, wherein the active agent is released from the dosage form through one or more passageways formed in the coating above the concave or convex structure(s) at a predetermined time after the dosage form is placed in an aqueous medium, and the release rate of the active agent is determined by the number and dimensions (e.g., height, width, depth, shape and/or size) of the concave or convex structure(s) and the amount of the polymer in the coating. Portions of the coating which are not immediately above the concave or convex structure(s) will tend to remain intact and/or adhered to the core for about 8 to 36 hours after the dosage form is placed in the aqueous medium. The coating in these embodiments may or may not be a compression coating, and the thickness of the coating may or may not be substantially the same throughout the perimeter of the dosage form.

In certain embodiments, the present invention is directed to a controlled release dosage form comprising a monolithic core comprising an active agent, the core having a surface comprising at least one structure (e.g., a peak and/or indentation) and coated with a coating comprising a polymer, wherein the active agent is released from the dosage form through one or more passageways formed in the portions of the coating immediately above or proximal to the structures at a predetermined time after the coated core (or the dosage form comprising the coated core) is placed in an aqueous medium, and portions of the coating which are not immediately above the structure(s) remain intact for about 8 to 36 hours after the dosage form is placed in the aqueous medium. The coating in these embodiments may or may not be a compression coating, and the thickness of the coating may or may not be substantially the same throughout the perimeter of the dosage form.

The release rate of an active agent from the dosage forms of the invention may be manipulated, e.g., by varying the number and dimensions (i.e., the height, width, depth, shape and/or size) of at least one structure and/or the thickness and composition of the coating. The dimensions of the structure(s) may be varied by using compression tooling (e.g., punch tip faces) with different height, width, depth, shape and/or size structures, peaks and/or indentations on the compression surface thereof.

In certain embodiments, the present invention is directed to a method of controlling a rate of release of an active agent from a pharmaceutical dosage form, the dosage form comprising a core coated with a coating having the same or different thickness throughout the perimeter of the dosage form, the method comprising altering the surface topography of the core to provide at least one structure (e.g., a peak or indentation) of a dimensions (e.g., height, width, depth, shape and/or size) sufficient to create at least one passageway in the coating at a predetermined location after the dosage form is placed in an aqueous medium, and such that the active agent is released from the dosage form substantially through the passageway(s).

In certain embodiments, the dosage form is resistant to ethanol extraction or "dose dumping" when exposed to ethanol. For example, in certain embodiments, the release profile of a dosage form of the present invention does not substantially change upon exposure of the dosage form to up to 40% ethanol in simulated gastric fluid (SGF), as compared to the release profile of the dosage form in SGF (0% ethanol). In further embodiments, the release rate of an active agent(s) from the dosage form in up to 40% ethanol in simulated gastric fluid (SGF) is slower that the release rate of the dosage form in simulated gastric fluid (SGF) (0% ethanol).

In certain embodiments, the present invention is directed to a method of controlling a rate of release of an active agent from a pharmaceutical dosage form, the dosage form comprising a core coated with a coating having the same or different thickness throughout the perimeter of the dosage form, the method comprising altering the surface topography of the core and adjusting the thickness of the coating such that at least one passageway is created in portions of the coating directly above areas of the core having the altered topography after the dosage form is placed in an aqueous medium, and the active agent is released from the dosage form substantially through the passageways at a predetermined time, predetermined rate and/or for a predetermined duration of time.

In certain embodiments, the present invention is directed to a method of controlling a rate of release of an active agent from a pharmaceutical dosage form, the dosage form comprising a core comprising the active agent and coated with a coating having the same or different thickness throughout the perimeter of the dosage form, the method comprising adjusting the number and dimension (i.e., the height, width, depth, shape and/or size) of structures (e.g., peak and/or indentation) on a surface of the core, and optionally adjusting the amount of a polymer in the coating, such that at least one passageway is created in the coating immediately above or proximal to the structure(s) at a predetermined time after the dosage form is placed in an aqueous medium, and the active agent is released from the dosage form substantially through the passageway(s) at a predetermined rate.

In certain embodiments, the present invention is directed to a method of preparing a controlled release dosage form comprising: (i) preparing a blend of an active agent with one or more pharmaceutically acceptable excipients; (ii) compressing the blend into a tablet core such that a surface of the core comprises at least one structure (e.g., peak and/or indentation) having predetermined dimensions (i.e., height, width, depth, shape and/or size); and (iii) coating the core with a polymer, wherein the dimensions of the structure(s) are such that at least one passageway is formed in the coating immediately above or proximal to the structure(s) at a predetermined time after the dosage form is placed in an aqueous medium, and the active agent is released from the dosage form substantially through the passageway(s) at a predetermined rate and for a predetermined duration of time. The thickness of the coating may or may not be substantially the same throughout the perimeter of the dosage form in these embodiments.

In further embodiments, the present invention is directed to a method of rendering a dosage form resistant to extraction by ethanol, or resistant to enhanced extraction by ethanol, (e.g., dose dumping), the method comprising: i) preparing a blend of an active agent with one or more pharmaceutically acceptable excipients which is (are) of a type(s) and in an amount(s) that will render the dosage form resistant to extraction by ethanol, or dose dumping when exposed to ethanol, (ii) compressing the blend into a tablet core such that at least one structure (e.g., a peak or indentation) having predetermined dimensions (e.g., height, width, depth, shape and/or size) is formed on a surface of the core, and (iii) coating the core with a coating comprising a polymer, wherein the dimensions of the structure(s) are such that at least one passageway is created in the portion of the coating immediately above or proximal to structure(s) at a predetermined time after the dosage form is placed in an aqueous medium, and the active agent is released from the dosage form substantially through the passageway(s) at a predetermined rate. In certain embodiments, the excipient that renders the dosage form resistant to extraction, or resistant to enhanced extraction, by ethanol (e.g., dose dumping) is polyethylene oxide or ethylcellulose, or a combination thereof. The thickness of the coating may or may not be the same throughout the perimeter of the dosage form in these embodiments.

In additional embodiments, the present invention is directed to a method of rendering a dosage form tamper-resistant, the method comprising: i) preparing a blend of an active agent with one or more pharmaceutically acceptable excipients which is (are) of a type and in an amount(s) that will render the dosage form tamper-resistant to mechanical, thermal and/or chemical tampering (e.g., tampering by means of crushing, shearing, grinding, chewing and/or dissolution in a solvent optionally in combination with heating (e.g., greater than about 45° C.) of the oral dosage form); (ii) compressing the blend into a tablet core such that at least one structure (e.g., a peak and/or indentation) of predetermined dimensions (i.e., height, width, depth, shape and/or size) is created on a surface of the core; and (iii) coating the core with a coating comprising a polymer, wherein the height, width, shape and/or size of the structure(s) is such that at least one passageway is created in the portion of the coating immediately above or proximal to the structure(s) at a predetermined time after the dosage form is placed in an aqueous medium, and the active agent is released from the dosage form substantially through the passageway(s) at a predetermined rate. In certain embodiments, the excipient is selected from the group comprising polyethylene oxide, polycaprolactone, Eudragit NE, and mixtures thereof. In certain embodiments, the dosage form is tamper resistant as described in U.S. application Ser. No. 11/844,872, filed on Aug. 24, 2007, hereby incorporated by reference. The thickness of the coating may or may not be the same throughout the perimeter of the dosage form in these embodiments. In further embodiments, the present invention is directed to a method of treating a medical condition in a human patient, the method comprising administering a dosage form of the present invention, the dosage form comprising a therapeutically effective amount of an active agent for the treatment or prophylaxis of the medical condition, to the patient. In certain embodiments, the dosage form is administered twice-a-day or once-a-day. In certain embodiments, the medical condition is pain. In certain embodiments, the dosage form comprises an opioid analgesic and/or an NSAID, and is administered twice-a-day or once-a-day.

In certain embodiments, the invention is directed to a tooling (e.g., a punch tip face) for creating at least one structure (e.g., a peak and/or indentation) on the surface of the core of a dosage form of the present invention. The tooling has a compression surface that has a topography which is the inverse of the topography of a surface of the core of the dosage form of the present invention.

Core

The core of the dosage form of the present invention comprises an active agent(s) and one or more pharmaceutically acceptable excipients, and has a surface with: (i) means for controlling the rate of release of the active agent from the dosage form, and/or (ii) means for initiating release of the active agent at a predetermined time and/or predetermined rate from the dosage form. According to certain embodiments the core itself provides some prolonged release of the active contained therein.

Active Agent(s)

Active agents in accordance with the present invention include, e.g., analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, mucolytics, muscle relaxants, osteoporosis preparations, opioid antagonists, respiratory agents, urinary tract agents, vitamins, minerals, stereoisomers, polymorphs, salts, prodrugs, metabolites, and mixtures of any of the foregoing.

In certain embodiments, the active agent is an opioid analgesic. In certain embodiments, the opioid analgesic is selected from alfentanil, buprenorphine, butorphanol, carfentanil, codeine, dipanone, fentanyl, hydrocodone, hydromorphone, oxycodone, oxymorphone, levorphanol, lofentanil, morphine, meperidine, methadone, remifantil, heroin, tramadol, etorphine, dihydroetorphine, sufentanil, stereoisomers, polymorphs, salts, metabolites, prodrugs, and mixtures of any of the foregoing.

In certain embodiments, the opioid analgesic is selected from hydrocodone, hydromorphone, oxycodone, morphine, stereoisomers, polymorphs, salts, metabolites, prodrugs, and mixtures of any of the foregoing.

In embodiments where the opioid analgesic is hydrocodone, a stereoisomer, polymorph or pharmaceutically acceptable salt thereof, the core (or the dosage form comprising the core) comprises from about 5 mg to about 360 mg of hydrocodone. In certain embodiments, the core comprises about 5 mg, about 7.5 mg, about 10 mg, about 12.5 mg, about 15 mg, about 17.5 mg, about 20 mg, about 25 mg, about 30 mg, about 40 mg, about 50 mg, about 60 mg, about 70 mg, about 80 mg, about 90 mg, about 100 mg, about 110 mg, about 120 mg, about 140 mg, about 150 mg, about 160 mg, about 170 mg, about 180 mg, about 190 mg, about 200 mg, about 210 mg, about 220 mg, about 230 mg, about 240 mg, or about 260 mg of hydrocodone.

In embodiments where the opioid agonist is oxycodone, stereoisomer, polymorph or pharmaceutically acceptable salt thereof, the core (or the dosage form comprising the core) comprises from about 5 to about 360 mg of oxycodone. In certain embodiments, the core comprises about 5 mg, about 10 mg, about 15 mg, about 20 mg, about 30 mg, about 40 mg, about 60 mg, about 80 mg, about 100 mg, about 120 mg, about 140 mg, about 160 mg, or about 180 mg of oxycodone.

In embodiments where the opioid analgesic is hydromorphone, stereoisomer, polymorph or pharmaceutically acceptable salt thereof, the core (or the dosage form comprising the core) comprises from about 2 to about 50 mg of hydromorphone. In certain embodiments, the dosage form comprises about 2 mg, about 4 mg, about 6 mg, about 8 mg, about 10 mg, about 12 mg, about 16 mg, about 20 mg, about 36 mg, about 32 mg or about 40 mg of hydromorphone.

In embodiments, where the active agent is morphine, or a stereoisomer, polymorph or pharmaceutically acceptable salt thereof, the core (or the dosage form comprising the core) comprises from about 15 to about 600 mg of morphine. In certain embodiments, the core comprises about 15 mg, about 30 mg, about 45 mg, about 60 mg, about 80 mg, about 100 mg, about 120 mg, about 160 mg, or about 200 mg morphine.

The active agent(s) generally comprises from about 0.1 to about 45% of the core by weight. In certain embodiments, the active agent comprises from about 0.2% to about 40% of the core by weight, from about 5% to about 35% of the core by weight, or from about 10% to about 30% of the core by weight.

In the embodiments of the invention, where the core comprises two active agents, one of the active agents may comprise from about 0.0007% to about 0.01% of the core by weight. For example, a core weighting 680 mg may comprise 0.0625 mg naltrexone and 5 mg of hydrocodone bitartrate.

The active agent(s) is (are) generally uniformly distributed throughout the core, and the concentration of an active agent in the core is substantially uniform throughout the core.

Excipients

Suitable excipients for inclusion in the core include, e.g., fillers, binders, insoluble polymers, disintegrants, lubricants, glidants, surfactants, effervescent bases, osmotically active agents, swelling agents like hydrophilic polymers (such as polyethyleneoxide), agents that slow/prolong the release of the active agent from the core, ion exchange resins, hydrophobic and hydrophilic materials like hydrophobic or hydrophilic polymers controlling/prolonging the rate of release of the active agent from the core, substances of a type and in an amount which form a semisolid or gel composition upon crushing, heating and/or exposure of the crushed core to an aqueous medium, and the like.

Suitable fillers include, e.g., water-soluble, compressible carbohydrates such as sugars, which include, e.g., dextrose, sucrose, isomaltalose, fructose, maltose, lactose, and polydextrose; sugar-alcohols including, e.g., mannitol, sorbitol, isomalt, maltitol, xylitol, and erythritol; starch hydrolysates including, e.g., dextrins, and maltodextrins, and the like; water insoluble, plastically deforming materials such as, e.g., microcrystalline cellulose and other cellulosic derivatives; water-insoluble brittle fracture materials such as, e.g., dicalcium phosphate, tricalcium phosphate and the like; and mixtures thereof.

Suitable binders include, e.g., dry binders such as, e.g., polyvinyl pyrrolidone, hydroxypropylmethylcellulose, and the like; wet binders such as, e.g., water-soluble polymers, including hydrocolloids such as, e.g., alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan, polyvinyl pyrrolidone, cellulosics, starches, and the like; and derivatives and mixtures thereof.

Suitable disintegrants include, e.g., sodium starch glycolate, cross-linked polyvinylpyrrolidone, cross-linked carboxymethylcellulose, starches, microcrystalline cellulose, and the like, and mixtures thereof.

Suitable lubricants include, e.g., long chain fatty acids and their salts, such as magnesium stearate and stearic acid, talc, waxes, and the like, and mixtures thereof.

Suitable glidants include, e.g., colloidal silicon dioxide, and the like.

In certain embodiments, a surfactant or an effervescent base is included in the core. The surfactant may be helpful in certain cases to overcome surface tension effects. Surfactants useful as release-modifying agents in the present invention can be anionic, cationic, nonionic, and/or amphoteric. For example, sodium lauryl sulfate, sodium dodecyl sulfate, sorbitan esters, polysorbates, pluronics, potassium laurate, and the like, may be included in the core.

In certain embodiments, osmotically active agents or osmagents may be included in the core. Such agents are particularly useful when the active agent has limited solubility in the environment of use. In certain embodiments, these agents may reduce internal pressure of the core.

In certain embodiments, the core includes swelling agents provided in an amount sufficient to facilitate the entry of an aqueous fluid into the core, without causing uncontrolled disruption of the coating(s) surrounding the core.

The core may also include agents which slow/prolong the release of active agent from the core. Examples of such agents include hydrophobic materials and insoluble polymers as well as hydrophilic materials such as hydrophilic polymers (e.g. polyethyleneoxide). Examples of suitable hydrophobic materials useful as release-modifying/prolonging agents include vegetable oils such as hydrogenated cottonseed oil, hydrogenated castor oil, and the like, acrylic polymers and cellulosic materials, and mixtures of any of the foregoing.

The core may also include one or more ion exchange resins.

Effervescent bases useful as release-modifying agents in the present invention include sodium glycine carbonate, sodium carbonate, potassium carbonate, sodium bicarbonate, potassium bicarbonate, calcium bicarbonate, and the like.

Osmagents useful as release-modifying agents in the present invention include, for example, sodium chloride, calcium chloride, calcium lactate, sodium sulfate, lactose, glucose, sucrose, mannitol, urea, and many other organic and inorganic compounds known in the art.

Examples of suitable swelling agents include synthetic gums such as hydroxypropylmethylcelluloses (HPMC), hydroxypropyl cellulose (HPC), carboxymethyl cellulose, and natural gums such as xanthan gum, locust bean gum, acacia, tragacanth, guar gum, carrageenan, and propylene glycol alginate as well as polyethyleneoxide Other release-modifying agents which may be useful in the present invention provide a soluble or insoluble polymer backbone to the core. Such agents may decrease unequal density areas of the core formed during the compression molding of the same. Suitable soluble polymers which may be incorporated into the core include those which melt upon compression and fuse upon cooling to provide nearly uniform cross-sectional density, such as polyethylene glycols having a molecular weight of from about 900 to about 20,000. Other water soluble polymers are those that can become sufficiently viscous upon contacting an aqueous fluid to provide the same effect, such as high molecular weight polyvinylpyrollidone (e.g., K90 grade, commercially available from GAF Corporation and having a molecular weight of about 360,000).

In certain embodiments, one of the excipients is a substance of a type and in an amount which forms a semisolid or gel composition upon crushing, heating and/or exposure of the crushed dosage to an aqueous medium. The semisolid composition serves to sequester the active agent in the crushed dosage form and renders the active agent undeliverable by injection or snorting. In certain embodiments, the substance is polyethylene oxide.

The excipients generally comprise from about 55% to about 99.9% or from about 55% to about 97% of the core by weight.

In certain embodiments, one of the excipients is polyethylene oxide. Polyethylene oxide comprises from about 60% to about 99%, or about 65% to about 95%, or at least about 60%, or at least about 90%, or at least about 92%, or at least about 94% of the core by weight.

Polyethylene oxide used in the dosage forms of the present invention may have a molecular weight of from about 25,000 to about 20,000,000, based on rheological measurements. In certain embodiments, the core comprises polyethylene oxide with molecular weight of from about 2,000,000 to about 15,000,000, or from about 2,000,000 to about 8,000,000. In certain embodiments, the polyethylene oxide has a molecular weight of about 2,000,000, or about 4,000,000, or about 7,000,000, or about 8,000,000. High molecular weigh polyethyleneoxide has a molecular weight of 1,000,000 to 20,000,000. Polyethylene oxide is considered to have an approximate molecular weight of 1,000,000 when a 2% (by wt) aqueous solution of said polyethylene oxide using a Brookfield viscometer Model RVF, spindle No. 1, at 10 rpm, at 25° C. shows a viscosity range of 400 to 800 mPa s (cP). Polyethylene oxide is considered to have an approximate molecular weight of 2,000,000 when a 2% (by wt) aqueous solution of said polyethylene oxide using a Brookfield viscometer Model RVF, spindle No. 3, at 10 rpm, at 25° C. shows a viscosity range of 2000 to 4000 mPa s (cP). Polyethylene oxide is considered to have an approximate molecular weight of 4,000,000 when a 1% (by wt) aqueous solution of said polyethylene oxide using a Brookfield viscometer Model RVF, spindle No. 2, at 2 rpm, at 25° C. shows a viscosity range of 1650 to 5500 mPa s (cP). Polyethylene oxide is considered to have an approximate molecular weight of 5,000,000 when a 1% (by wt) aqueous solution of said polyethylene oxide using a Brookfield viscometer Model RVF, spindle No. 2, at 2 rpm, at 25° C. shows a viscosity range of 5500 to 7500 mPa s (cP). Polyethylene oxide is considered to have an approximate molecular weight of 7,000,000 when a 1% (by wt) aqueous solution of said polyethylene oxide using a Brookfield viscometer Model RVF, spindle No. 2, at 2 rpm, at 25° C. shows a viscosity range of 7500 to 10,000 mPa s (cP). Polyethylene oxide is considered to have an approximate molecular weight of 8,000,000 when a 1% (by wt) aqueous solution of said polyethylene oxide using a Brookfield viscometer Model RVF, spindle No. 2, at 2 rpm, at 25° C. shows a viscosity range of 10,000 to 15,000 mPa s (cP). Regarding the lower molecular weight polyethylene oxides; Polyethylene oxide is considered to have an approximate molecular weight of 100,000 when a 5% (by wt) aqueous solution of said polyethylene oxide using a Brookfield viscometer Model RVT, spindle No. 1, at 50 rpm, at 25° C. shows a viscosity range of 30 to 50 mPa s (cP) and polyethylene oxide is considered to have an approximate molecular weight of 900,000 when a 5% (by wt) aqueous solution of said polyethylene oxide using a Brookfield viscometer Model RVF, spindle No. 2, at 2 rpm, at 25° C. shows a viscosity range of 8800 to 17,600 mPa s (cP).

A combination of polyethylene oxides having different molecular weights may be used in certain embodiments of the invention, e.g., to adjust the release rate of the active agent from the core (e.g., to increase the release rate when the release rate would otherwise be too slow for a particular purpose). In certain embodiments, the core comprises a combination of: (i) polyethylene oxide having a molecular weight of less than about 1,000,000, or less than about 900,000; and (ii) polyethylene oxide having a molecular weight of more than about 1,000,000, or more than about 1,500,000 or more than about 2,000,000. In certain embodiments, the polyethylene oxide having a molecular weight of less than about 1,000,000 or less than about 900,000 comprises about 5%, about 10%, about 15% or about 20% of the core by weight.

In certain such embodiments, polyethylene oxide having a molecular weight of more than about 1,000,000 comprises at least about 80% by weight of the core. In certain embodiments, polyethylene oxide having a molecular weight of more than about 1,000,000 comprises at least about 85% or at least about 90% by weight of the core. In such embodiments, a polyethylene oxide having a molecular weight of at least 4,000,000 or at least 7,000,000 may be employed.

In certain embodiments, the active agent is dispersed in a matrix comprising polyethylene oxide(s).

In certain embodiments, the core comprises hydroxyl alkylcellulose (e.g., hydroxypropyl cellulose) and/or microcrystalline cellulose. In certain embodiments, hydropropyl cellulose comprises from about 0.1% to about 7% by weight of the core, or from about 0.2% to about 6% by weight of the core, or from about 0.2% to about 5% by weight of the core. In certain embodiments, microcrystalline cellulose comprises from about 0.1% to about 7% by weight of the core, or from about 0.2% to about 6% by weight of the core, or from about 0.2% to about 5% by weight of the core.

In certain embodiments, the core consists essentially of an active agent, polyethylene oxide and a lubricant. In certain embodiment, the lubricant is magnesium stearate. In certain embodiments, the core comprises magnesium stearate in an amount of from about 0.1% to about 5%, or from about 0.1% to about 2%, or from about 0.2% to about 1% by weight of the core.

In certain embodiments, the core comprises a material selected from the group consisting of polyethylene oxide, hydroxypropyl cellulose, hydroxypropyl methylcellulose, hydroxyethyl cellulose, microcrystalline cellulose, polycaprolactone, glyceryl behenate, magnesium stearate, and mixtures of any of the foregoing.

Means for Controlling Release Provided by the Surface of the Core

The core of the present dosage forms of the invention has a shape that has been modified to provide at least one means for controlling the release of the active agent(s). Although not wishing to be bound by any particular theory, the inventor believes that the release-controlling means on the core creates a weak point within a coating that has been coated over the core, and this can be used to facilitate a consistent and reproducible rupturing of the coating in that portion of the coating which is situated immediately above or proximal to the release-controlling means upon placement of the coated core into an aqueous medium.

In certain embodiments, the release-controlling means comprises at least one structure (e.g., a peak, indentation, serration, groove, embossment, engraving, imprint, or combination thereof) on the surface of the core. This topographical modification to the surface of the core is of a size and shape that will serve to create a weak point in that portion of the coating located immediately above or proximal to the release-controlling means, thereby facilitating a consistent and reproducible rupturing of the coating above the release-controlling means, resulting in a controlled release of the active agent for a desired period of time (e.g., 12 or 24 hours) at a desired rate upon placement of the coated core (or a dosage form comprising the coated core) into an aqueous medium.

In certain embodiments, the structure(s) on the surface of the core does (do) not have the same composition as the core.

In certain embodiments, the structure(s) on the surface of the core has (have) the same composition as the core.

In certain embodiments, the core has at least one structure on the surface thereof. In certain embodiments the core has a total of from 1 to 50 structures on the surface thereof. In certain embodiments, the core has a total of from 1 to 30, 1 to 20, 2 to 30, 3 to 20, or 4 to 20 structures on the surface thereof. In certain embodiments, the core contains a total of 1, 2, 3, 4, 5, 6, 7, 8, 9, or 10 structures on the surface thereof.

In certain embodiments, the total surface area occupied by the structure(s) is generally less than about ⅕, less than about ⅙, less than about ⅐, less than about ⅛, less than about ⅑, or less than ¹/₁₀ of the total surface area of the core.

The total surface area of the structure(s) generally is from about 0.1% to about 25% of the total surface area of the core. In certain embodiments, the total surface area of the structure(s) is from about 0.5% to about 20% of the total surface area of the core. In certain embodiments, the total surface area of the structure(s) generally is from about 1% to about 15% of the total surface area of the core.

Surface area can be estimated, e.g., by caliper measurement (or using other non-contact measurement methods) of each axis of the core, and using appropriate mathematics to calculate surface area. Alternatively, other surface area measurement techniques (e.g., BET measurements) can be used. For example, a surface area of a standard radius concave tablet, can be calculated by using the following formula:

$$\text{Surface area} = 2\pi[(D/2)(t-2cd)+(D/2)^2+cd^2],$$

wherein D is a diameter, cd is a cup depth, and t is thickness.

In certain embodiments, the surface area of the structure(s) provides (provide) an increase in the total surface area of the core of from about 1% to about 25% of the total surface area of the core. In certain embodiments, the increase in the surface area of the core provided by the addition of the structure(s) is about 4%, about 5%, about 6%, about 7%, about 8%, about 9%, about 10%, about 11%, about 12%, about 13% or about 14% of the total area of the core, as compared to the core without the structure(s) on the surface thereof.

In certain embodiments, where the core comprises a tablet comprising a top face, a bottom face, and a side band connecting the top face and the bottom face, the structure(s) provides (provide) an increase in the surface area of the top face and/or bottom face of from about 0.5% to about 25%. In certain embodiments, the increase in the surface area of the top face and/or the bottom face provided by the structure(s) is about 4%, about 5%, about 6%, about 7%, about 8%, about 9%, about 10%, about 11%, about 12%, about 13% or about 14%, as compared to the surface area of an identical top face and/or bottom face which has not been modified to have such structure(s).

The percent increase in the surface area may be calculated by: (1) measuring/calculating plain cup surface area of the top face before the top surface is modified to have the structure(s); (2) measuring/calculating the surface area of the top face after it has been modified to have the structure(s); (3) subtracting the surface area of the top face calculated in (1) from the surface area of the top face calculated in (2); and (4) calculating the percent increase in the surface area of the top face after it has been modified. For example, the percent increase in surface area for a core comprising a tablet with a plain cup surface area (i.e., before the surface of the tablet has been modified to have one or more structures) of 0.159519 in², and a top face surface area after modifications of 0.178467 in² will have an increase in surface area of about 10.6% ((0.1785467−0.159519)/0.1785467)×100%=10.6%).

The release rate of the active agent from the core is determined by a number of factors, including the number and dimensions (i.e., the height, width, depth, shape and/or size) of the release-controlling means on the surface of the core, and the composition and amount of the polymer in the coating.

The number and dimensions of the structures on the surface of the core are such that they will be sufficient to create at least one weak point(s) in the coating coated immediately thereover or proximal thereto, such that upon exposure of the dosage form to an aqueous medium, the coating will tend to rupture first at the site of the weak point(s), thereby forming at least one passageway in that portion of the coating which is immediately above or proximal to each structure, thereby allowing the aqueous medium to enter the core such that the active agent will be released from the dosage form at a controlled rate substantially through the passageway(s).

The number and dimensions of the structures necessary to provide results in accordance with the present invention may be determined by one of ordinary skill in the art via the following steps: (i) preparing different cores having different numbers of structures and/or structures of different dimensions; (ii) optionally curing the cores (e.g., at a temperature of about 45° C. to about 85° C. for about 0.2 to about 4 hours); (iii) coating the cores with a coating having the same thickness on each core; (iv) optionally curing the coated cores; (v) optionally adding a film coat to the coated cores; (vi) optionally curing the film coated cores; (vii) performing dissolution tests of the coated cores; (viii) examining the coated cores after dissolution testing; and (ix) choosing those coated cores having the appropriate numbers and dimensions of structures such that, upon exposure to the aqueous medium, they form one or more passageways in the coatings immediately above or proximal to the structure(s) and release the active agent substantially through said passageway(s) at a controlled release rate for the desired period of time (e.g., about 6, about 12, or about 24 hours). In those embodiments where the core comprises polyethylene oxide, the cores may be cured at about a melting temperature of polyethylene oxide (about 65° C. to 85° C.) for about 15 to about 60 minutes.

In certain embodiments, the number and dimension of the structure(s) may be determined using mathematical formulas and the desired rate of release. For example, a surface area required to provide a desired rate of release from a compressed soluble disc in a dissolution-controlled dosage form may be estimated using the following equation: A=(dm/dt/dx/dt)/C, wherein A is the surface area; C is the concentration of an active agent; dm/dt is the rate of release; and dx/dt is the mass erosion rate. The number and dimension of the structure(s) required to provide such a surface are then determined. The number and dimension of structures can then be further adjusted by formulating and testing the coated cured cores as described in the preceding paragraph.

In certain embodiments, the height, width, and/or depth of each structure is from about 20 microns to about 5 millimeters, from about 30 microns to about 4 millimeters, from about 30 microns to about 3 millimeters, from about 30 microns to about 2 millimeters, from about 30 microns to about 0.5 millimeters, from about 100 microns to about 2 millimeters, from about 200 microns to about 2 millimeters, from about 500 microns to about 2 millimeters, from about 1 millimeters to about 4 millimeters, from about 0.5 millimeter to about 3 millimeters, from about 2 to about 5 millimeters, or from about 1 millimeter to about 2 millimeters.

In certain embodiments, the structure(s) on the surface of the core has (have) a concave or a convex shape.

Types of Cores

In certain embodiments, the core is non-erodible and does not decrease in dimensions when the coated or uncoated core is placed in an aqueous medium (e.g., a Simulated Gastric Fluid (SGF)). For example, in certain embodiments, the surface area of the core remains about the same for at least about 2 to about 24 hours, about 3 to about 24 hours, about 4 to about 24 hours, about 6 to about 24 hours, about 2 to about 12 hours, about 2 to about 10 hours, or about 4 to about 8 hours, after the coated core (or the dosage form containing the coated core) is placed in the aqueous medium.

In certain embodiments (e.g., those dosage forms having a core comprising an eroding matrix), the surface area of the core decreases as the time interval during which the dosage form containing the core is exposed to an aqueous medium increases.

In certain embodiments (e.g., those dosage forms having a core comprising polyethylene oxide), the surface area of the core will increase, e.g., due to the hydration and swelling of the core, as the time interval during which the dosage form containing the core is exposed to an aqueous medium increases.

In certain embodiments, the core is not expandable and does not increase in dimensions in the presence of an aqueous medium.

In certain embodiments, the core comprises a hydrophilic matrix.

In certain embodiments, the core is a tablet. In certain embodiments, the tablet comprises a groove around the periphery of the tablet face edge. In certain embodiments, the tablet comprises a uniform notched (i.e., serrated) edge (e.g., "a saw-like" edge) around the periphery of the tablet face edge. In certain embodiments, the tablet comprises a rippled edge (e.g., "a wave-like" edge).

In certain embodiments, the core is a monolithic core.

In certain embodiments, the core is a compressed core.

In certain embodiments, the core is a tamper-resistant core, e.g., as described in U.S. application Ser. No. 11/844,872, which is herein incorporated by reference.

In certain preferred embodiments, the core comprises a controlled-release matrix comprising one or more of the excipients mentioned above.

In certain embodiments, the core is a cured core which is resistant to crushing or enhanced extraction in up to 40% ethanol, e.g., as described in U.S. application Ser. No. 11/844,872.

In certain embodiments, the core comprises an immediate-release matrix comprising one or more of the excipients mentioned above.

Primary Coating/Controlled Release Coating

The dosage forms of the present invention comprise a core that is coated with a primary coating. The primary coating provides for a controlled release of the active agent. The coating comprises a suitable amount of a material to completely cover and isolate the core from the environment of use until, e.g., at least one passageway is formed in the coating immediately above or proximal to at least one structure attached to the core after the coated core is exposed to an aqueous medium (e.g., simulated gastric fluid, (SGF)). The primary coating is preferably not a compression coating. In certain embodiments, the coating is a dipped or enrobed coating. In other embodiments, the coating is a spray coating or a pan coating. The thickness of the coating may or may not be the same throughout the perimeter of the dosage form.

In certain preferred embodiments, the primary coating attains essentially the same shape as the underlying core (i.e., the outer surface of the coating presents topographical features that generally mimic or approximate the shape and size of any structures located below on the surface of the core). In certain other embodiments, the primary coating does not attain the same shape as the core (e.g., the outer surface of the coating is essentially smooth overall, and does not have any visible surface features that would indicate the presence of any underlying structures located below on the surface of the core). Furthermore, the topographical features of the inner and outer surfaces of the coating will be different due to the presence of structures on the surface of the underlying core. In other words, the inner surface of the coating will present structures that will be the inverse of any structures located on the surface of the core, while the outer surface of the coating may or may not have any visible topographical features corresponding to the shape and size of any structures located on the surface of the core.

The primary coating on the core does not initially contain any passageways (i.e., those purposely created in the coating during manufacturing (e.g., laser drilled passageways)).

The primary coating generally contains from about 0.5% to about 30% of the dosage form by weight. In certain embodiments, the coating contains from about 1% to about 25%, from about 1% to about 20%, from about 2% to about 15%, or from about 1% to about 10% of the dosage form by weight. In certain embodiments, the coating contains about 1, 2, 3, 4, 5, 6, 7, 8, 9 or 10% of the dosage form by weight.

The thickness of the primary coating necessary to provide results in accordance with the present invention may be empirically determined by one of ordinary skilled in the art via: (i) coating cores (cured or uncured) having a surface with at least one structure created thereon with differing coating thicknesses; (ii) performing dissolution tests of the coated cores in an aqueous medium; (iii) examining the coated cores after dissolution; and (iii) choosing the thickness of the coating which, upon exposure to the aqueous medium, forms passageways in the portion of the coating immediately above or proximal to the structure(s) and releases the active agent substantially through the passageway(s) at a controlled release rate for the desired period of time (e.g., about 6, about 12, or about 24 hours). The thickness of the coating may or may not be the same throughout the perimeter of the dosage form. Cores comprising polyethylene oxide may be cured at about the melting temperature of the particular polyethylene oxide (about 65° C. to 85° C.) for about 15 to about 60 minutes.

The coating may be applied in the form of an organic or aqueous solution or dispersion. Coatings derived from aqueous dispersions are described in detail, e.g., in U.S. Pat. Nos. 5,273,760 and 5,286,493, assigned to the Assignee of the present invention and hereby incorporated by reference.

Representative materials suitable for use in the primary coating include those materials commonly considered to be insoluble in the art, such as an alkyl cellulose (e.g., ethyl cellulose), acrylate polymers, polyamides (nylons), polymethacrylates, polyalkenes (polyethylene, polypropylene), bio-degradable polymers (including homo- or hetero-polymers of polyhydroxy butyric or valeric acids and homo or hetero-polymers of polylactic, polyglycolic, polybutyric, polyvaleric, and polycaprolactic acids), waxes, natural oils, other hydrophobic insoluble materials such as polydimethylsiloxane, hydrophilic materials such as cross-linked sodium carboxymethyl cellulose and cross-linked sodium or uncrosslinked carboxy-methyl starch. Many other polymers considered to be relatively insoluble may also be useful in the present invention.

In certain embodiments, the primary coating comprises a material comprising: (i) an alkylcellulose; (ii) an acrylic polymer; or (iii) mixtures thereof.

In certain embodiments, an alkylcellulose is ethylcellulose. In certain embodiments, an ethylcellulose coating contains from about 0.5% to about 6% by weight of the coated core. In certain other embodiments, an acrylic or ethylcellulose coating contains from about 7% to about 12% or from about 5 to about 10% by weight of the coated core.

One commercially available aqueous dispersion of ethylcellulose is Aquacoat® (FMC Corp., Philadelphia, Pa., U.S.A.). Aquacoat® is prepared by dissolving ethylcellulose in a water-immiscible organic solvent, and then emulsifying the same in water in the presence of a surfactant and a stabilizer. After homogenization to generate submicron droplets, the organic solvent is evaporated under vacuum to form a pseudo-latex. Plasticizer is not incorporated in the pseudo-latex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion that can be applied directly onto substrates.

In certain embodiments, the controlled-release material comprising the primary coating is selected from pharmaceutically acceptable acrylic polymers, including but not limited to acrylic acid and methacrylic acid copolymers, methyl methacrylate copolymers such as copolymers of ethyl acrylate and methyl methacrylate, ethoxyethyl methacrylates, cyanoethyl methacrylate, poly(acrylic acid), poly(methacrylic acid), methacrylic acid alkylamide copolymer, poly (methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain embodiments, the acrylic polymer is comprised of one or more ammonio methacrylate copolymers. Ammonio methacrylate copolymers are well-known in the art, and are described in NF XVII as fully polymerized copolymers of acrylic and methacrylic acid esters with a low content of quaternary ammonium groups.

In certain embodiments, the primary coating comprises a mixture of two acrylic resin lacquers commercially available from Evonik under the tradename Eudragit®, e.g., Eudragit RL30D and Eudragit® RS30D. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. The code designations RL (high permeability) and RS (low permeability) refer to the permeability properties of these agents. Eudragit® RL/RS mixtures are insoluble in water and in digestive fluids.

The Eudragit® RL/RS dispersions of the present invention may be mixed together in any desired ratio in order to ultimately obtain a sustained release formulation having a desirable dissolution profile. Desirable sustained release formulations may be obtained, for example, from a retardant coating derived from 100% Eudragit® RL, or 50% Eudragit® RL and 50% Eudragit® RS, or 10% Eudragit® RL:Eudragit® 90% RS.

In embodiments of the present invention where the primary coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating-containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can generally only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although other water-insoluble plasticizers (such as acetylated monoglycerides, phthalate esters, castor oil, etc.) may be used. Triethyl citrate is an especially preferred plasticizer for aqueous dispersions of ethyl cellulose.

Examples of suitable plasticizers for acrylic polymers include but are not limited to citric acid esters such as triethyl citrate NF XVI, tributyl citrate, dibutyl phthalate, and possibly 1,2-propylene glycol. Other plasticizers suitable for enhancing the elasticity of the films formed from acrylic films such as Eudragit® RL/RS lacquer solutions include polyethylene glycols, propylene glycol, diethyl phthalate, castor oil, and triacetin.

It has further been found that the addition of a small amount of talc reduces the tendency of the aqueous dispersion to stick during processing, and acts as a polishing agent. Accordingly, talc may be included in the primary coating in certain embodiments of the invention.

Controlled-release materials which may be included in the primary coating may be selected, e.g., from alkylcelluloses, hydroxyalkylcelluloses, acrylic polymers, shellac, zein, hydrogenated castor oil, hydrogenated vegetable oil, and mixtures thereof. In certain embodiments of the invention, the controlled-release material in the primary coating is a pharmaceutically acceptable acrylic polymer selected from acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid) (anhydride), polymethacrylate, polyacrylamide, poly(methacrylic acid anhydride), glycidyl methacrylate copolymers, and mixtures thereof. In certain embodiments, the controlled-release material comprises a hydroxyalkylcellulose such as e.g., hydroxypropylmethylcellulose.

While some of the above materials exhibit a certain degree of permeability to environmental fluids such as water, in certain embodiments the coating is applied at such a thickness that the core is not exposed to environmental fluid until at least one passageway is formed in the coating immediately above or proximal to at least one structure attached to the core according to the present invention after the dosage form is placed into the environmental fluid.

It is also possible to use a relatively thick coating of a material otherwise considered in the art to be relatively soluble in an environmental fluid to effectively achieve the purpose of the present invention. Examples of such materials include polyvinylpyrrolidone; cellulose ethers including hydroxypropylmethylcellulose, methylcellulose, hydroxyethylcellulose, and hydroxypropylcellulose; sodium carboxymethyl cellulose, sodium carboxymethyl starch and enteric materials (such as cellulose acetate phthallate, polyvinylalcohol phthallate, shellac, zein, hydroxypropylmethyl cellulose phthallate, cellulose acetate trimaleate, etc).

It is also possible to use coatings comprising combinations of relatively insoluble and relatively soluble materials to effectively achieve the purpose of the present invention.

In certain embodiments, the coating contains from about 90 to about 96.5 percent hydrogenated vegetable oil, from about 3 to about 5 percent polyvinylpyrrolidone, and from about 0.5 to about 5 percent magnesium stearate or other similar lubricant.

In certain embodiments, the coating is permeable to the active agent, but is impermeable to water.

In other embodiments, the coating is impermeable to the active agent but is permeable to water.

In certain embodiments, the coating is a hydrophobic coating.

In certain embodiments, the coating is a non-porous coating.

In certain embodiments, the controlled release coating comprises gelatin. In certain embodiments, the coating is a gel coating.

In certain embodiments, the coating uniformly adheres to the core, meaning that there are no gaps or open spaces between the inner surface of the coating and the outer surface of the core.

In certain embodiments, the coating remains intact and adheres to the core, with the exception of the one or more passageways that form(s) in the coating immediately above or proximal to at least one structure for a time period of from about 1 hour to about 24 hours, from about 1 hour to about 12 hours, from about 1 hour to about 8 hours, from about 1 hour to about 6 hours, from about 1 hour to about 4 hours, or from about 1 to about 3 hours, during which the dosage form is exposed to an aqueous medium.

In certain embodiments, the coating remains continuous and intact until the coating ruptures at the position of at least one weak point immediately above or proximal to at least one structure on the surface of the core. In certain embodiments, the dimensions or width of each passageway once formed is essentially constant. In other embodiments, the width of each passageway once formed increases with time. The width of each passageway may be measured using an electronic microscope and/or a digital image via image analysis software. In certain embodiments, the width of each passageway 24 hours after the passageway is initially formed is not more than about 60% larger, or not more than about 50% larger, or not more than about 40% larger, or not more than about 30% larger, or not more than about 20% larger, or not more that about 10% larger than the width of the passageway at the time of its initial formation.

In certain embodiments, the width of the passageway 12 hours after the passageway was initially formed is not more than about 50% larger, or not more than about 40% larger, or not more than about 30% larger, or not more than about 20% larger, or not more than about 10% larger than the width of the passageway at the time of its initial formation.

In certain embodiments, the width of the passageway once formed remains essentially constant, i.e., it remains about the same, for a time period of from about 1 hour to about 24 hours, or from about 1 hour to about 12 hours, or from about 1 hour to about 8 hours, or from about 1 hour to about 6 hours, or from about 1 hour to about 4 hours, or from about 1 to about 3 hours, after the dosage form has been exposed to an aqueous medium.

In certain embodiments, the coating remains substantially completely attached to the core for at least about 2, 3, 4, 5, 6, 7, 8, 9, 10, 11, 12, 13, 14, 15, 16, 17, 18, 19, 20, 21, 22, 23, 24, 26, 28, 32 or 36 hours after the dosage form is exposed to an aqueous medium. In certain embodiments, less than about ⅕, or ⅙, or ⅐, or ⅛, or ⅑ or ⅒ of the total surface area of the core is exposed to an aqueous medium for at least 12, 24 or 36 hours after the dosage form has been placed into the aqueous medium. In certain embodiments, from about 1% to about 10% of the total surface area of the core is exposed to an aqueous medium for at least 12, 24 or 36 hours after the dosage form has been placed into the aqueous medium.

In certain embodiments, portions of the coating which are not immediately above or proximal to the structure remain substantially intact and adhered to the core for about 6 to 36 hours after the dosage form containing the coated core is placed in an aqueous medium. In certain embodiments, the portions of the coating which are not immediately above or proximal to the structure remain substantially intact and adhered to the core for about 7, 8, 10, 11, 12, 16, 18 or 24 hours after the dosage form is placed in an aqueous medium.

In certain embodiments, the coating completely disintegrates only after substantially all of the active agent has been released from the dosage form.

In certain embodiments, each passageway formed in the coating immediately above or proximal to each structure is about 0.1 mm to about 1 mm in width, is about 0.1 mm to about 0.5 mm in depth, and exposes less than about ⅙ of the total surface area of the core. Such passageways may facilitate the release of the active agent from the core at a zero-order release rate.

In certain embodiments, each passageway formed in the coating immediately above or proximal to each structure is greater than about 1 mm in width and/or 0.5 mm in depth.

Such passageways may facilitate the release of the active agent from the core at a first-order release rate.

Additional Coatings

The dosage form can, optionally, have one or more additional coatings, each of which may be coated over and/or under the primary coat described above. In certain embodiments, an additional coating under the primary coating as part of the core may improve adhesion of the primary coat to the core or and/or act as a physical barrier between the core and the primary coating. In certain embodiments, the dosage form has a coating comprising hydroxylpropyl methyl cellulose (e.g., Opadry®) coated under the primary coat.

In certain embodiments, an additional coating over the primary coating may improve palatability and swallowability of the dosage form.

In certain embodiments, an additional coating is coated under the primary coating described above. This additional coating may prevent or minimize ruptures in the primary coating produced during curing of the dosage form. This additional coating may also minimize or prevent tacking (e.g., during the curing of the tablet cores), provide better adhesion of the primary coat to the core, provide improved stability of the dosage form (e.g., by acting as an oxygen barrier to prevent degradation of the API or by preventing migration of the active agent into the primary coating during manufacturing and/or storage), or provide for product identification from a security perspective (e.g., by providing a detectable marker to authorities to enable identification of counterfeit products or products that have been diverted).

In certain embodiments, the additional coating comprises hydroxypropyl methyl cellulose (e.g., Opadry®). The additional coating will preferably be coated directly onto the surface of the core and under the primary coat. In certain embodiments, the additional coating is coated to obtain a weight gain of from about 0.1 to about 8% by weight of the uncoated core. In certain embodiments, the weight gain is about 0.2%, about 0.4%, about 0.6%, about 0.7%, about 0.8%, about 1%, about 1.4%, about 1.6%, about 1.8%, about 1.9%, about 2%, about 2.5%, or about 3%. The additional coating is preferably coated in an effective amount to prevent or minimize ruptures in the primary coat during curing. In certain embodiments, the effective amount to prevent or minimize ruptures in the primary coat during curing is from about 1.2% to about 2.5%. In preferred embodiments, the additional coat completely surrounds the core. In other embodiments, the additional coat only surrounds a portion of the core.

In certain embodiments, an additional coating over the primary coating may be a functional coating. For example, such additional coating may be an enteric coating (i.e., a coating designed to dissolve only in certain regions of the gastrointestinal tract). An enteric coating may contain from about 0.5 to about 35% of the uncoated core by weight.

An enteric coating may comprise a methacrylic acid ester-type polymer, or mixtures thereof. For example, the enteric coating may comprise a methacrylic acid copolymer which swells and dissolves in acidic media (e.g., Eudragit® E), a methacrylic acid copolymer which does not swell at about pH<5.7 and is soluble at about pH>6 (e.g., Eudragit® L), or a methacrylic acid copolymer which does not swell at about pH<6.5 and is soluble at about pH>7 (e.g., Eudragit® S).

An enteric coating may comprise cellulose acetate phthalate, hydroxypropyl methylcellulose phthalate, carboxymethyl ethylcellulose, hydroxypropyl methylcellulose acetate succinate, polyvinyl acetate phthalate, cellulose acetate trimellatate, cellulose acetophthalate, cellulose acetate terephthalate, polyvinyl alcohol phthalate, or a mixture of any of the foregoing.

In other embodiments, the additional coating may be an opacifying coating (designed to block light from reaching a light-sensitive drug).

In certain embodiments, an adhesive coat such as shellac or polyvinyl acetate phthalate (PVAP) is applied to the core prior to applying the impermeable coating in order to improve adhesion of the impermeable coating to the core.

In certain embodiments, all of the portions of the coating in contact with the core are substantially homogeneous (e.g., are free from any impermeable discs as described in U.S. Pat. No. 5,902,598).

In certain embodiments, the additional coating may contain an active agent, either the same or different from that in the core. In certain embodiments, the additional coating over the primary coat comprises an active agent(s) in immediate release form, in addition to the active agent(s) in the core. In certain embodiments, the active agent in the additional coating is the same as the active agent in the core. In other embodiments, the active agent in the additional coating is different from the active agent in the core.

The dosage form of the invention may further incorporate one or more pharmaceutically acceptable excipients selected, for example, from preservatives; high intensity sweeteners such as aspartame, acesulfame potassium, cyclamate, saccharin, sucralose, and the like; other sweeteners such as dihydroalcones, glycyrrhizin, and the like; flavors; antioxidants; surfactants; and coloring agents.

Dosage Forms

The dosage form of the present invention may be an oral dosage form, an oromucosal dosage form, a sublingual dosage form, a buccal dosage form, an intravaginal dosage form, a cervical dosage form, an intrauterine dosage form, a rectal dosage form, an implant dosage form, or an injectable dosage form. In preferred embodiments, the dosage form is an oral dosage form.

A tablet comprises a top face, a bottom face, and a side wall or band. The side wall and the top face may form a top face edge or corner at the intersection of the side wall and the top face. The side wall and the bottom face may form a bottom face edge or corner at the intersection of the side wall and the bottom face. The tablet may be coated with a coating having the same or different thickness throughout the perimeter of the dosage form.

In certain embodiments, the dosage form of the present invention is a tablet comprising a groove around the periphery of the top and/or bottom face edge and coated with a coating. This groove may serve as a structure according to the present invention. Thus, the size and the shape of the groove are such that at least one passageway is created in the portion of the coating immediately above or proximal to the groove at a predetermined time after the dosage form is placed in an aqueous medium, and the portions of the coating not immediately above nor proximal to the groove will tend to remain substantially intact and adhered to the core for about 8 to 36 hours after the dosage form is placed in the aqueous medium. In certain embodiments the groove is a V-shape grove.

In certain embodiments, the dosage form of the present invention is a tablet comprising a uniform notched (i.e., serrated) edge around the periphery of the top and/or bottom face edge and coated with a coating. The number and dimensions of the serrations are such that at least one passageway is created in the portion of the coating immediately above or proximal to the notched edge at a predetermined time after the dosage form is placed in an aqueous medium, and the portions of the coating not immediately above nor proximal to the notched edge will tend to remain substantially intact and adhered to the core for about 8 to 36 hours after the dosage form is placed in the aqueous medium.

In certain embodiments, the dosage form of the present invention is a tablet comprising a core having at least one convex and/or at least one concave structure on one or both faces of the core, which core is then coated with a coating according to the present invention. The number and dimensions of the convex or concave structure(s) are such that at least one passageway is created in the coating immediately above or proximal to the convex and/or concave structure(s) at a predetermined time after the dosage form is placed in an aqueous medium, and the portions of the coating not immediately above nor proximal to the convex and/or concave structure(s) will tend to remain substantially intact and adhered to the core for about 8 to 36 hours after the dosage form is placed in the aqueous medium.

In certain embodiments, the dosage form of the present invention comprises a plurality of multiparticulates, each multiparticulate comprising a core having a surface with at least one structure and a coating according to the invention. In certain embodiments, the multiparticulates are disposed in a pharmaceutically acceptable capsule or in a pharmaceutically acceptable diluent (solid or liquid).

Method of Manufacturing

A dosage form in accordance with certain embodiments of the present invention may be manufactured by first creating a core having a surface with at least one structure. The core may or may not then be cured. The core is then coated with a coating to completely cover the surface of the core. The coated core may or may not then be cured. Thus, preparation of the final dosage form may involve no curing step, or at least one or two curing steps, depending on the particular formulation.

The core of the dosage form of the present invention may be prepared by any suitable method including, for example, by compression or molding. Depending on the method by which the core is made, it will typically comprise, in addition to the API, one or more excipients.

For example, the core with a surface having at least one structure may be prepared by direct compression. Generally, a method of preparing a core by direct compression comprises blending together the materials that will comprise the core (e.g., an active agent(s) and one or more excipients), preferably as dry powders, and then feeding the blend into an apparatus that applies pressure to form the core. Any suitable compacting apparatus may be used, including for example a roller compactor such as a chilsonator or drop roller, or a conventional tablet press. In certain embodiments, the blend is compressed more than once to form the core with a surface having at least one structure (first compression to form the core having, e.g., substantially flat, convex, or concave surfaces or a combination thereof; second compression to form at least one structure on the surface of the core).

In a different embodiment, the one or more structures on the surface of the core are created by spraying a material(s) onto the surface of the core to form one or more structures. Ink jet technologies may be applicable for this purpose.

In certain embodiments, a lubricant is mixed with the API and other excipients prior to compression into a solid core. Any generally accepted pharmaceutical lubricant, such as calcium or magnesium salts, may be used. In certain embodiments, the lubricant is magnesium stearate in an amount of about 0.25-6% by weight of the core.

In certain embodiments, the core is formed by compaction using a rotary tablet press. In a rotary tablet press, a metered volume of powder is filled into a die cavity, which rotates as part of a "die table" from the filling position to a compaction position where the powder is compacted between an upper and a lower punch to an ejection position where the resulting tablet is pushed from the die cavity by the lower punch.

In certain embodiments, the direct compression process enables the minimization or elimination of water-soluble, non-saccharide polymeric binders such as polyvinyl pyrrolidone, alginates, hydroxypropyl cellulose, hydroxypropylmethylcellulose, hydroxyethylcellulose, and the like, which may have an adverse effect on dissolution in some circumstances.

The core may also be prepared by a wet-granulation method. Generally, a wet granulation method comprises mixing and granulating an active agent(s) and appropriate excipients as a solution or dispersion with a wet binder (e.g. an aqueous cooked starch paste, or a solution of polyvinyl pyrrolidone). Suitable apparatuses for wet granulation include low shear mixers (e.g. planetary mixers); high shear mixers; and fluid beds, including rotary fluid beds. The resulting granulated material is dried and optionally dry-blended with further ingredients, e.g., adjuvants and/or excipients such as for example lubricants, colorants, and the like. The final dry blend is then suitable for compression by the methods described above.

In certain embodiments, the core is created by preparing a blend of an active agent(s) with one or more pharmaceutically acceptable excipients, and compressing the blend into a monolithic tablet having at least one structure of predetermined dimensions on a surface thereof.

In certain embodiments, the core is created by preparing a blend of an active agent(s) with one or more pharmaceutically acceptable excipients, compressing the blend into a monolithic core, and subsequently modifying the topography of the surface of the compressed monolithic core to create at least one structure of predetermined dimensions on a surface thereof, for example by: (i) an additional compression step using a die defining at least one structure (e.g., a peak or indentation); and/or (ii) spraying the monolithic core with the blend such so as to form one or more structures on the surface of the monolithic core.

In certain embodiments, the core having at least one structure according to the present invention is created by subjecting a core to selective application of force at one or more locations (e.g., by engraving, scratching, striking; etc.).

Once the core having a surface with at least one structure according to the present invention is created, it may or may not be cured, depending on the particular formulation. Under some circumstances, the curing step is carried out at a temperature of about 45° C. to about 85° C. for about 0.2 to about 3 hours. It is believed that such a curing step may, e.g., increase the tamper-resistance of a dosage form comprising the cured core.

In certain embodiments of the invention, magnesium stearate or talc is added during or after the curing step in order to prevent the cores from sticking together. In certain embodiments, the magnesium stearate or talc is added at the end of the curing step before cooling of the cores or during the cooling of the cores. Other anti-tacking agents that could be used include silica, fumed silica, colloidal silica dioxide, calcium stearate, carnauba wax, long chain fatty alcohols and waxes, such as stearic acid and stearyl alcohol, mineral oil, paraffin, micro crystalline cellulose, glycerin, propylene glycol, and polyethylene glycol.

Each core is then coated with a coating(s) as described above. In certain embodiments, the coating is created by compression. In certain other embodiments, the coating is applied by spray or pan coating. In certain embodiments, the coating is applied by spray coating. In certain embodiments, the coating is applied by dipping or enrobing. When the dosage form is applied by compression, the coating may or may not have the same density throughout the perimeter of the dosage form.

In certain embodiments, the coating is formed by film formation from a polymer in solution, or suspension using pouring or spraying onto a pre-formed tablet core. Preferably, this process is carried out by spraying the coating onto the tablet core in a rotating pan coater or in a fluidized bed coater until the desired coating thickness is achieved. Alternatively, a tablet core may be dip coated or melt coated. This is especially useful with waxes and oils. In other embodiments, the core may be compression-coated. In other words, a suitable impermeable coating material may be pressed onto a pre-formed tablet core.

In certain embodiments, e.g., with a coating comprising an aqueous dispersion of hydrophobic polymers (e.g., acrylic polymers or ethylcellulose), the coated core (which core may or may not have already been subjected to a first curing step) may or may not then be subjected to a curing step at a temperature above the glass transition temperature of the coating material (e.g., acrylic polymer or ethylcellulose) contained in the coating for about 24 to 72 hours. With a coating comprising ethylcellulose, the post-coating curing step may be conducted at a relative humidity of from about 60% to about 100%. This post-coating curing step may result in a coated cured core exhibiting stabilized dissolution, meaning that after storage at accelerated storage conditions (i.e., at least one month at a temperature of 40° C. and a relative humidity of 75%), the release profile of the active agent from the coated cured core at any given time will not vary by more than about 30% from the release profile of the active agent before the subject to the accelerated storage conditions.

In certain embodiments, there is only one curing step during manufacture of the final dosage form, either before coating of the core or after coating of the core, depending on the particular formulation. In other embodiments, there are two curing steps during manufacture of the final dosage form, both before coating and again after coating of the core.

In certain embodiments, the initial curing is at a temperature of about 45° C. to about 85° C. for about 0.2 to 3 hours. In other embodiments, the initial curing is at a temperature of about 73° C. for about 20 to 40 minutes.

This application claims priority from U.S. Provisional Application Ser. No. 61/422,512, filed Dec. 13, 2010, the disclosure of which is hereby incorporated by reference.

Example 1

Monolithic tablets, each comprising 20 mg hydrocodone bitartrate, were prepared using the following procedure.

1. A granulation of the formulation set forth in Table 1 was prepared.

TABLE 1

| Formulation for Granulation (Lot Number CW1M80) | | |
| --- | --- | --- |
| Ingredient | mg/unit | Actual Amt Used (kg) |
| Hydrocodone Bitartrate, USP | 120 | 7.04 |
| Hydroxypropyl Cellulose (Klucel EXF) | 8.18 | 0.48 |
| Microcrystalline Cellulose, NF (Avicel PH 101) | 8.18 | 0.48 |
| Total | 136.36 | 8.00 |
| Water, USP Purified * | | 1.788 |

* Removed during the drying process.

2. The formulation granulation was dried and milled.
3. A tablet blend of the formulation set forth in Table 2 was prepared.

TABLE 2

| Formulation for hydrocodone (HYD) 20 mg uncoated tablets | | | | | |
| --- | --- | --- | --- | --- | --- |
| Formulation: - Tablet Blend (target 20 mg/500 mg tablets) | | | | | |
| Ingredient | mg/unit | Theoretical Amount (g) | Actual Amt Used (g) | Lot Number | Other info |
| Milled HYD granulation | 22.73 (4.546%) | 318.22 | 313.6 [1] | CW1M80 | granulation assay 89.3% (per CoA) |
| PEO 303 | 474.27 (94.854%) | 6639.78 | 6651.4 [2] | XA2255S5R3 | LEO, viscosity 9433 cps (per CoA) |
| BHT (milled) | 0.5 (0.1%) | 7 | 7 | 091038 | from Micron Technologies |
| Magnesium Stearate | 2.5 (0.5%) | 35 | 35 | M02345 | vegetable source; mfg Mallinckrodt |
| Total | 500 | 7000 | 7000 | | |

[1] Amount adjusted based on the granulation assay value; calculation (theoretical amount granulation/actual % assay) × theoretical % assay (318.22 g/0.893) × 0.88 = 313.6 g HYD granulation.

[2] Amount adjusted based on the adjusted granulation amount Calculation: batch total amount − magnesium stearate amount − adjusted granulation amount = adjusted amount of PEO to be used 7000 g − 35 g − 313.6 g = 6651.4 g PEO.

4. Hydrocodone bitartrate (HYD) 20 mg monolithic tablet cores were prepared using a rotary tablet press. The top face of each tablet was imprinted with the designation "500." The bottom face of each tablet was imprinted with the designation "BNS" situated over "9090" in a circular pattern.

5. Tablets prepared in step 4 above were cured for 30 minutes at a target exhaust temperature of 72° C. in a 24-inch coating pan.

6. A coating dispersion of formulation set forth in Table 3 was prepared (12% NE30D Solids, 6% talc, 82.0% aqueous carrier).

TABLE 3

| Material | | grams | % |
|---|---|---|---|
| NE30D dispersion | Solids | 135 | 12.0% |
| | Liquid | 315 | 28.0% |
| Talc | | 67.5 | 6.0% |
| Water | | 607.5 | 54.0% |
| Total | | 1125 | 100.0% |

7. Tablets cured in step 5 above were coated with Eudragit NE30D using a Vector LDCS tablet coater to achieve a target weight gain of 8%. The formulation of the Eudragit NE 30D coated tablet is set forth in Table 4.

TABLE 4

Formulation:- Tablet Film Coating with NE30D

| material | mg/unit | Theoretical amount | Actual amount | Lot number/ information |
|---|---|---|---|---|
| HYD 20 mg Tablets | 500 | 1500 | 1500 | 1722-51 |
| Eudragit NE30D | 40 | 120[1] | 450 (135 g solids[2]) | B080912075 Stability: end of September 2010 (per label) |
| Talc | 20 | 60 | 67.5[2] | L1821 |
| Total | 560 | 1680 | 1702.5 | |

[1] based on NE30D solids weight gain of 8%
[2] includes 12.5 excess

8. Tablets coated with the NE30D film coat were then cured via application of Opadry® coat to a target weight gain of 3% over 121 minutes at a temperature (inlet) of from 18.6° C. at the onset to 37° C. at 121 minutes. Parameters of coating/curing are set forth in Table 5.

The weight gain of 60 tablets (each tablet was numbered) was monitored through the process so that at the end of the process, individual tablet weight gain and coating efficiency could be calculated. The coating level (NE30D solids) for these tablets was determined to be from 6.78 to 8.31%.

Figure 6:
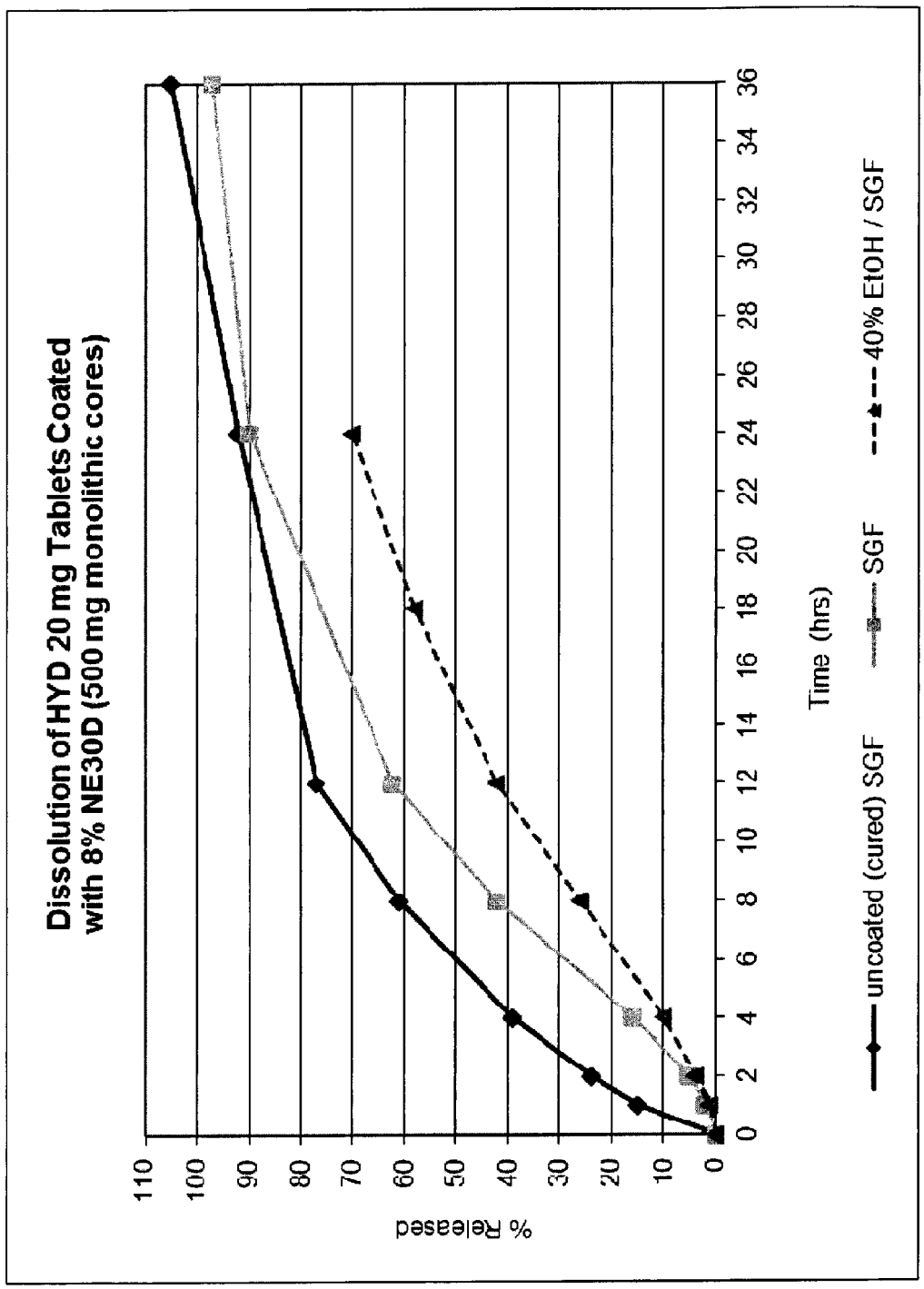
FIG. 6 is a graph showing the results of the dissolution testing of Example 1 with a debossed surface image.

9. Dissolution testing was conducted in SGF (analytical reference 1691-72) and in 40% ethanol/SGF (analytical reference 1739-42). The results of the dissolution are set forth in FIG. 6. The results showed that the release rate of hydrocodone in the tablet in 40% ethanol/SGF fluid was slower than the release rate of hydrocodone in SGF.

10. After the dissolution testing, the leftover coating film was removed and photographed with a microscope. The photographs revealed that the film coat had ruptured around areas of the tablet imprint. This was observed at two different coating levels, 6.8% and 8.2%.

Figure 7:
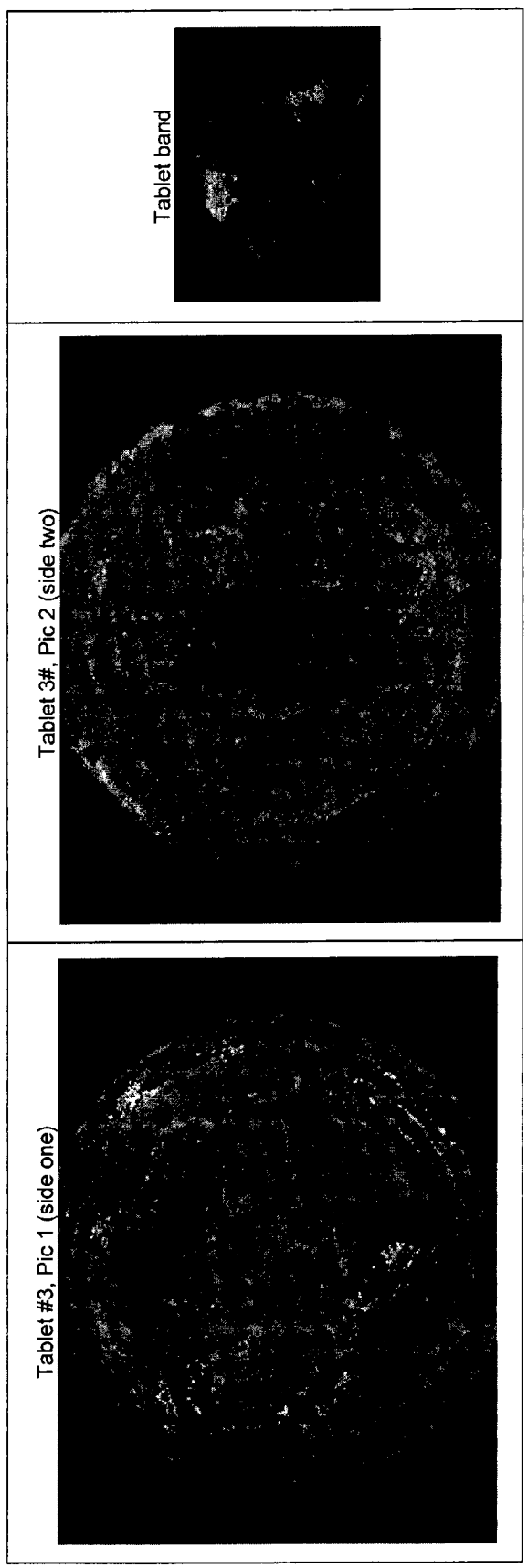
FIG. 7A shows photographs of Tablet 3 of Example 1 after the dissolution testing showing ruptures at the edge of the debossed image.
FIG. 7B shows photographs of Tablet 39 of Example 1 after the dissolution testing.
Figure 7:
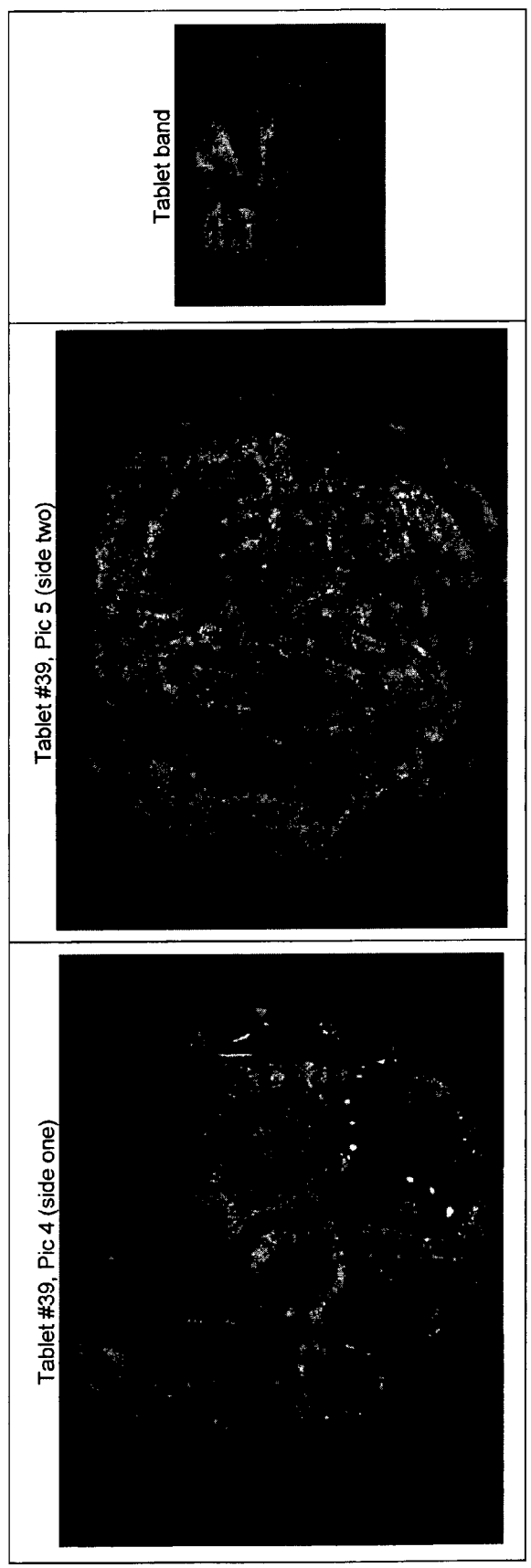
Figure 8:
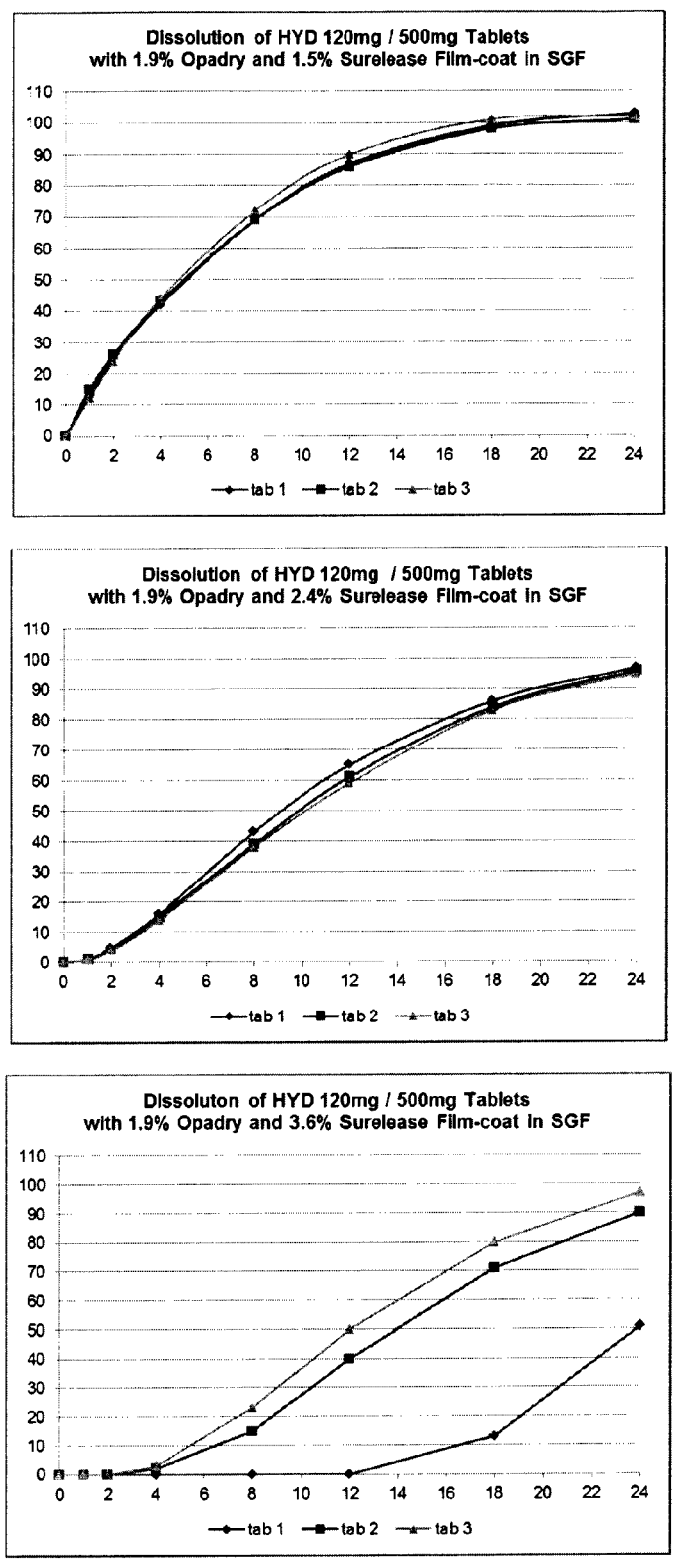
FIG. 8 shows dissolution graphs of the monolithic tablet cores with 1.5% surelease, 2.4% surelease and 3.6% surelease coatings of Example 4.
Figure 9:
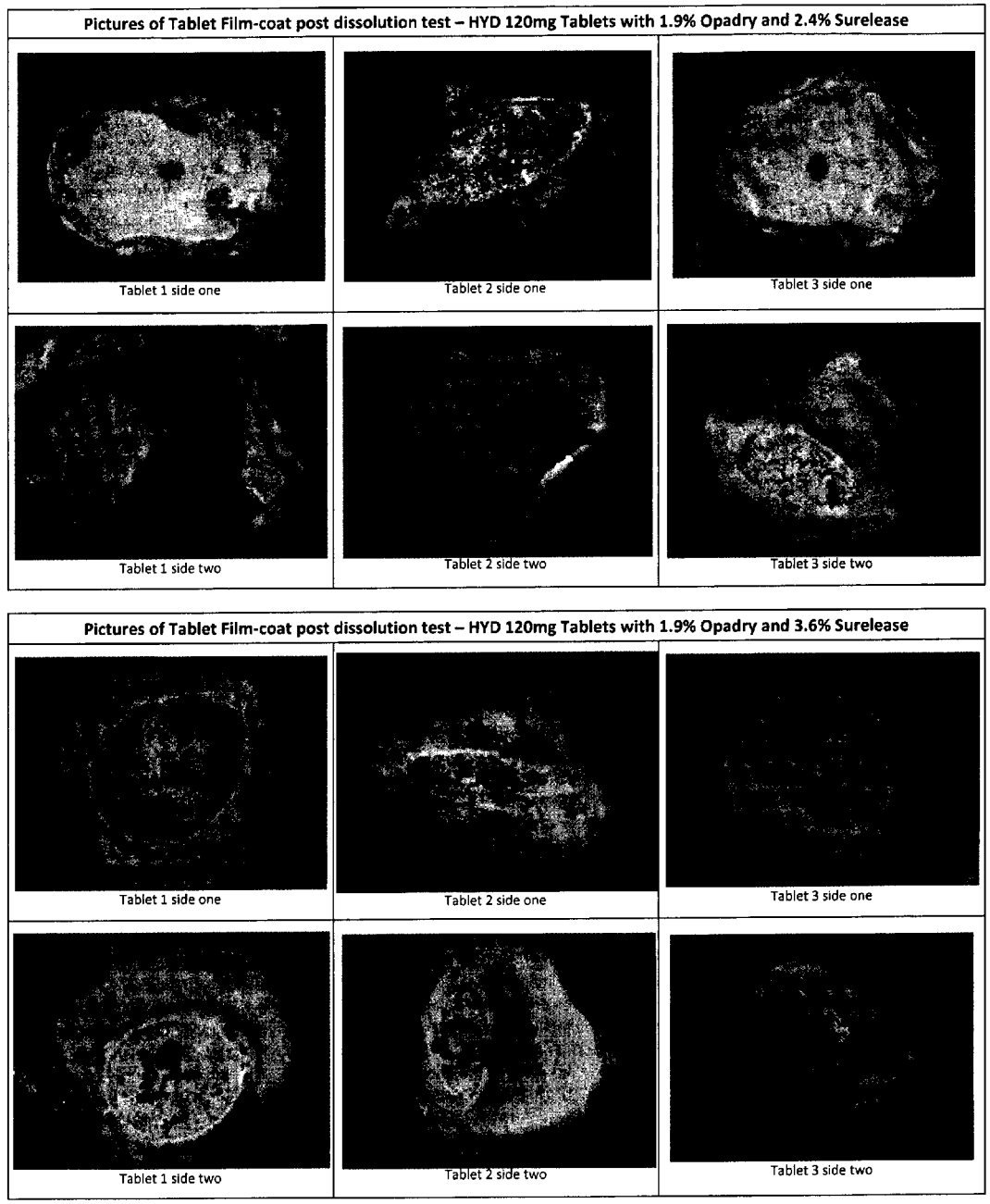
FIG. 9 shows photographs of the monolithic tablet cores after dissolution with 1.5% surelease, 2.4% surelease and 3.6% surelease coatings of Example 4.
Figure 10:
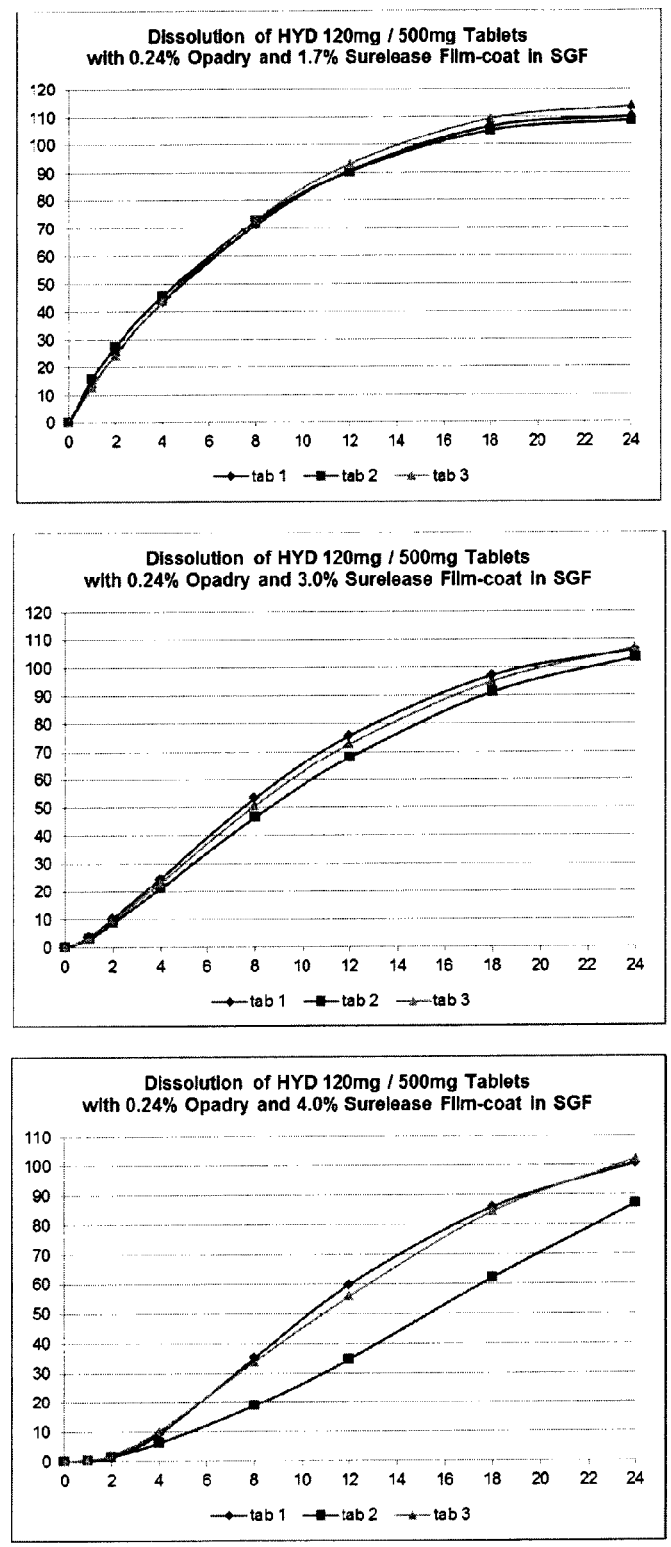
FIG. 10 shows dissolution graphs of the monolithic tablet cores with 1.7% surelease, 3.0% surelease and 4.0% surelease coatings of Example 4.
Figure 11:
FIG. 11 shows photographs of the monolithic tablet cores after dissolution with 1.7% surelease, 3.0% surelease and 4.0% surelease coatings of Example 4.

For example, photographs of coating shells of Tablet 3 and Tablet 39 are presented in FIGS. 7A and 7B. Tablet 3 had 8.2% theoretical NE30D solids applied. Tablet 2 had theoretical 6.8% NE30D coating applied.

Picture 1 of Tablet 3 revealed an area of coat rupture around the imprinted "5" area on the top face of the tablet. Picture 2 of Tablet 3 reveals that the bottom face of the tablet does not appear to have any ruptures. The coating of the tablet bands (side walls) showed some ruptures.

Picture 4 of Tablet 39 revealed an area of coat rupture around the imprinted "5" and center "0" area on the top face of the tablet. Picture 5 revealed an area of coat rupture around the "0" and "9" imprint. The pieces of coating from the tablet bands appeared intact.

Comparative Example 2

A bulk supply of hydrocodone bitartrate (HYD) 120 mg/500 mg monolithic tablet cores was prepared using the following procedure.

1. Hydrocodone granulations of the formulations set forth in Tables 6A and 6 B were prepared. Each lot below uses the same formulation except for different amounts of water to granulate.

TABLE 5

| | Temperature (° C.) | | | Inlet | | Atom | | | Flow | |
|---|---|---|---|---|---|---|---|---|---|---|
| Time (min) | Inlet Set | Inlet Actual | Exhaust | air cfm | Pan rpm | Air psi Gun | Pump rpm | Amt sprayed grams[2] | rate g/min | Comments Weight of 30 tablets: 16.7000 g |
| 0 | 25/40 | 18.6 | 18.5 | 30 | 3 | of/of | off | n/a | n/a | Load tablets start warming |
| 10 | 65 | 50.7 | 27.9 | 30 | 12 | of/of | off | n/a | n/a | Continue warming, no sticking |
| 15 | 62 | 60.6 | 35.2 | 50/30 | 15/20 | 16.0/5.0 | 9 | n/a | ~5 | Start spray, at 19 minutes decrease pump to 8 rpm |
| 25 | 65 | 64.4 | 36.9 | 30 | 25 | 15.0/5.0 | 8 | n/a | ~4 | None |
| 35 | 62 | 61.7 | 37.4 | 30 | 25 | 15.0/5.0 | 9 | n/a | ~5 | None |
| 45 | 62 | 61.9 | 37.8 | 30 | 25 | 15.0/5.0 | 9/10 | n/a | ~6 | Weight of 30 tablets: 16.754 g |
| 75 | 64 | 63.9 | 39.9 | 30 | 25 | 15.0/5.0 | 12 | n/a | ~8 | Weight of 30 tablets: 16.952 g |
| 95 | 64 | 63.9 | 36/1 | 30 | 25 | 15.0/5.0 | 12/14 | n/a | ~8/~10 | Temperature probe at lower bed 50.7° C.p Weight of 30 tablets: 17.062 g[1] |
| 110 | 66/off | 65.8 | 35.1 | 30 | 25/15 | of/of | 14/off | n/a | n/a | Temperature probe 51.2° C.; weight of 30 tablets: 17.166 g |
| 121 | off | 37.0 | 34.0 | 31 | 5 | of/of | 14/off | n/a | n/a | Discharge |

[2]N/A, monitored tablet weight gain

TABLE 6A

Formulation for Granulation (Lot Number CW1M80)

| Ingredient | mg/unit | Actual Amt Used (kg) |
|---|---|---|
| Hydrocodone Bitartrate, USP | 120 | 7.04 |
| Hydroxypropyl Cellulose (Klucel EXF) | 8.18 | 0.48 |
| Microcrystalline Cellulose, NF (Avicel PH 101) | 8.18 | 0.48 |
| Total | 136.36 | 8.00 |
| Water, USP Purified * | | 1.788 |

* Removed during the drying process

TABLE 6B

Formulation for Granulation (Lot Number CW1M90)

| Ingredient | mg/unit | Actual Amt Used (kg) |
|---|---|---|
| Hydrocodone Bitartrate, USP | 120 | 7.04 |
| Hydroxypropyl Cellulose (Klucel EXF) | 8.18 | 0.48 |
| Microcrystalline Cellulose, NF (Avicel PH 101) | 8.18 | 0.48 |
| Total | 136.36 | 8.00 |
| Water, USP Purified * | | 1.600 |

* Removed during the drying process

2. The granulation was milled.
3. The tablet blend formulation set forth in Table 7 was prepared using an 8 qt V-blender:

TABLE 7

| Ingredient | mg/unit | Theoretical amount | Actual amount used | Lot number | Other info |
|---|---|---|---|---|---|
| Milled HYD granulation | 136.3 (27.26%) | 664.6 | 649.57[1] | CW1M80, CW1M90 | Two lots (from four PRC numbers) were used for this batch |
| PEO 303 | 360.7 (72.14%) | 1758.8 | 1719.04[2] | XA2255S5R3 | LEO, viscosity 9433 cps (per CoA) |
| BHT | 0.5 (0.1%) | 2.4 | 2.38 | 091038 | From Micron Technologies |
| Magnesium Stearate | 2.5 (0.5%) | 12.2 | 11.91 | M02345 | vegetable source; mfg Mallinckrodt |
| Total | 500 | 2438 | 2382.9 | | |

[1] actual amount adjusted based on the granulation assay value. Calculation: (theoretical amount granulation/actual % assay) x theoretical % assay.
[2] PEO amount adjusted based on the adjusted granulation amount. Calculation: batch total amount − magnesium stearate amount − BHT amount − adjusted granulation amount = adjusted amount of PEO.

4. A rotary tablet press (Kilian T100) was set-up with 7/16 inch, round, deep cut tooling (8 stations).

5. All of the tablet blend was loaded into the hopper.

6. 500 mg weight tablet cores (each containing 120 mg hydrocodone bitartrate) were compressed.

7. The tablet cores prepared in step 6 were loaded into an 18 inch coating pan.

8. A coat of Opadry® was applied to tablets to a target level of approximately 1% weight gain. This pre-coat was intended to eliminate tablet sticking during the curing process. The actual weight gain was 1.9%.

9. Tablets coated with Opadry® were cured at target exhaust 72° C. in a pan size of 18 inches. The curing process information is set forth in Table 8.

TABLE 8

| Time (min) | Temperature (° C.) | | | Air vol cfm | Pan rpm | Comments |
|---|---|---|---|---|---|---|
| | Inlet Set | Inlet Actual | Exhaust | | | |
| 0 | 22/85 | 21.7 | 23.4 | 349 | 6 | start heating |
| 8 | 85 | 71.2 | 61.3 | 352 | 6/10 | Pan shutdown; quickly restart machine, increase rpm to 10 |
| 19 | 85 | 84.7 | 72.0 | 350 | 10 | Start curing |
| 29 | 77 | 77.0 | 72.2 | 351 | 10 | 10 min cure time, no sticking |
| 39 | 76 | 75.9 | 71.8 | 349 | 10 | 20 min cure time, no sticking |
| 49 | 76.5/22 | 76.5 | 72.4 | 351 | 10 | 30 min cure time, no sticking, start cooling |
| 54 | 22 | 38.0 | 52.8 | 347 | 10 | no sticking observed, continue cooling |
| 70 | 22 | 22.3 | 26.0 | 353 | 10/off | discharge |

Comparative Example 3

Hydrocodone bitartrate monolithic tablet cores containing 120 mg of the formulation set forth in Table 9 were prepared by direct compression (raw API mixed with excipients, then compressed) using the following procedure.

TABLE 9

| Ingredient | mg/unit | Theoretical amount (g) | Actual amount used (g) | Lot Number | Other info |
|---|---|---|---|---|---|
| Hydrocodone bitartrate | 120 (24%) | 1200 | 1200 | 4-09HYD | |
| PEO 303 | 374.5 (74.9%) | 3745 | 3745 | XA2255S5R3 | LEO, viscosity 9433 cps (per CoA) |

TABLE 9-continued

| Ingredient | mg/unit | Theoretical amount (g) | Actual amount used (g) | Lot Number | Other info |
|---|---|---|---|---|---|
| BHT (milled) | 0.5 (0.1%) | 5 | 5 | 091038 | from Micron Technologies |
| Magnesium Stearate | 5 (1%) | 50 | 50 | M02345 | Vegetable source; mfg Mallinckrodt |
| Total | 500 | 5000 | 5000 | | |

1. Hydrocodone bitartrate, milled BHT, and approximately half of the PEO was added to the 16 qt V-Blender, and mixed for 5 minutes with the I-bar ON.

2. Magnesium stearate (screened through a 20-mesh screen) was added and mixed for one minute, NO I-bar.

3. A rotary tablet press (Kilian T100) was set-up with 7/16 inch round, deep cut tooling (8 stations).

4. All of the tablet blend was loaded into the hopper and 500 mg tablet cores (each containing 120 mg of hydrocodone bitartrate) were compressed.

5. The tablets were then coated with Opadry® (Opadry Green Y-5-11167-A Lot TS052509) to a weight gain of 0.24%.

6. Tablets coated with Opadry® were cured for 30 minutes at target exhaust 72° C. in a pan size of 24 inches. The curing process information is set forth in Table 10.

TABLE 10

| | Temperature (° C.) | | | Air | | |
|---|---|---|---|---|---|---|
| Time (min) | Inlet Set | Inlet | Exhaust | vol Cfm | Pan Rpm | comments |
| 0 | 22/85 | 22.5 | 25.9 | 350 | 4 | Start heating |
| 5 | 85 | 77.0 | 54.6 | 354 | 4/8 | Continue |
| 20 | 85 | 85.0 | 72.0 | 353 | 12 | Start curing, no sticking |
| 30 | 77 | 76.8 | 72.3 | 351 | 12 | 10 min cure time point, no sticking |
| 40 | 75.5 | 75.6 | 71.9 | 352 | 12 | 20 min cure time point, no sticking, start cooling |
| 50 | 76/22 | 75.6 | 72.4 | 352 | 12 | 30 min cure time, no sticking, start cooling |
| 56 | 22 | 34.2 | 52.8 | 350 | 12/8 | No sticking observed during cool down, continue cooling |
| 68 | 22 | 22.2 | 29.7 | 351 | 5 | Discharge, weight of 100 tablets: 50.166 g |

Comparative Example 4

Monolithic tablet cores prepared in Examples 2 and 3 were coated with ethylcellulose (Surelease®) coating to target percent weight gain of 1%, 2%, 3%, and 4% (actual percent weight gains of 1.5%, 1.7%, 2.4%, 3.0%, 3.6%, 4.0%, 4.7%, and 5.1%) using the following procedure.

1. A coating dispersion of ethylcellulose formulation set forth in Table 11 was prepared (15% total solids, 85% aqueous carrier).

TABLE 11

| Material | grams | % |
|---|---|---|
| Surelease E-7-1940 288 g | 72 | 15% |
| | 216 | 45% |
| DI-water | 192 | 40% |
| Total | 480 | 100% |

2. Monolithic tablet cores prepared in Examples 2 and 3 were coated with Surelease using Vector LDCS tablet coater. A formulation based on a Surelease solids weight gain of 4% is set forth in Table 12.

TABLE 12

| Formulation:- Tablet Film Coating with Surelease | | | | |
|---|---|---|---|---|
| Material | mg/unit | Theoretical amount(g) | Actual amount (g) | Lot number/ information |
| HYD 120 mg Tablets | 500 | 1500 | 750.0 | Green Opadry subcoat 0.24% |
| | | | 750.2 | Pink Opadry Subcoat 1.9% |
| Surelease Clear E-7-19040 | 20 | 60[1] | 288 (72 g solids)[3] | IN516799 |
| DI-water | n/a | n/a | 192[3] | lab |
| Total | 520 | 1560 | 1572.2 | |

[1] based on Surelease solids weight gain of 4%

[2] includes 20% excess

[3] added to prepare 15% solids suspension

Target coating parameters are set forth in Tablet 13 below.

TABLE 13

| Parameter | Target |
|---|---|
| Pad speed | 14 rpm |
| Gun to bed distance | 2.5 inches |
| Spray rate | 5 g/min (initial) |
| Atomization air | 15 psi |
| Inlet Air Volume | 35-40 cfm |
| Inlet temperature | 50° C. |
| Exhaust Temperature | 38° C. |

Actual coating parameters are set forth in Table 14 below.

TABLE 14

| | Temperature (° C.) | | | | | Amt | Flow | | Comments |
|---|---|---|---|---|---|---|---|---|---|
| Time (min) | Inlet Set | Inlet Actual | Probe | Exhaust | Pan rpm | Pump rpm | sprayed grams | rate g/min | Weight | Tubing size 46410-16 |
| 0 | Off/45 | 21.6 | 22.4 | 20.8 | 5 | off | 0 | n/a | 50.415 | Load tablets, start warming, air vol. 35 cfm |
| 7 | 45 | 44.5 | 38.3 | 28.6 | 5/14 | 7 | 0 | ~5 | n/a | Start spray, spray pattern air 0.8 psi |
| 12 | 45 | 45.0 | 39.0 | 29.6 | 14 | 7 | 20.7 | 4.14 | n/a | none |
| 17 | 45 | 44.9 | 39.2 | 30.1 | 14 | 7 | 42.9 | 4.44 | n/a | none |
| 22 | 45 | 44.9 | 39.3 | 30.5 | 14 | 7 | 65.3 | 4.48 | n/a | none |
| 27 | 45 | 44.8 | 39.3 | 30.9 | 14 | 7 | 87.7 | 4.48 | n/a | none |
| 30 | 45 | 44.8 | 39.4 | 30.9 | 14 | 7 | 101.3 | 4.53 | 51.141 | take sample, ~1% weight gain at 31 minute, increase pump to 8 rpm |
| 35 | 45 | 44.8 | 39.2 | 30.5 | 14 | 8 | 127.3 | 5.2 | n/a | none |
| 40 | 45 | 44.9 | 39.2 | 30.4 | 14 | 8 | 154.4 | 5.42 | n/a | none |
| 45 | 45 | 44.9 | 39.2 | 30.4 | 14 | 8 | 181.7 | 5.46 | n/a | none |
| 49 | 45 | 44.8 | 39.2 | 30.4 | 14 | 8 | 203.4 | 5.43 | 51.728 | take sample, ~2% weight gain |
| 56 | 45 | 44.9 | 39.2 | 30.4 | 14 | 8/9 | 214.7 | 5.47 | n/a | Increase pump to 9 rpm |
| 61 | 45 | 44.7 | 38.9 | 29.7 | 14 | 9 | 273.8 | 6.42 | n/a | none |
| 64 | 45 | 44.8 | 38.9 | 29.7 | 14 | 9 | 296.7 | 7.63 | 52.287 | take sample, ~3% weight gain |
| 69 | 45 | 44.6 | 38.6 | 29.5 | 14 | 9 | 329.0 | 6.46 | n/a | none |
| 74 | 45 | 44.7 | 38.6 | 29.4 | 14 | 9 | 362.6 | 6.72 | n/a | none |
| 80 | 45/off | 44.8 | 38.7 | 29.4 | 14 | 9/off | 405.0 | 7.07 | n/a | Stop stray, ~4% weight gain, decrease pan to 5 rpm |
| 100 | off | 27.2 | 28.7 | 28.6 | 5 | off | n/a | n/a | 52.812 | discharge |

8. Each sample was returned to the tablet bed at the end of spraying.

9. The weight change of tablet samples is set forth in Table 15.

TABLE 15

| Sample | Initial Weight (g) | Post Drying Weight (g) | Change (g) | Weight Gain |
|---|---|---|---|---|
| 1% | 51.141 | 51.137 | 0.004 | 1.4% |
| 2% | 51.728 | 51.696 | 0.032 | 2.5% |
| 3% | 52.287 | 52.247 | 0.040 | 3.6% |
| 4% | n/a | 52.812 | n/a | 4.8% |

Actual % weight gains for 8 samples are set forth in Table 16.

TABLE 16

| | 1 | 2 | 3 | 4 | 5 | 6 | 7 | 8 |
|---|---|---|---|---|---|---|---|---|
| % coat target | 1% | 1% | 2% | 2% | 3% | 3% | 4% | 4% |
| Sample size | 50 | 50 | 50 | 50 | 50 | 50 | 50 | 50 |
| Net wt (g) | 25.475 | 25.686 | 25.811 | 25.905 | 26.067 | 26.194 | 26.340 | 26.477 |
| Avg Tab wt (mg)[1] | 509.5 | 513.7 | 516.2 | 518.1 | 521.3 | 523.9 | 526.8 | 529.5 |
| Actual % coat[2] | 1.7 | 1.5 | 3.0 | 2.4 | 4.0 | 3.6 | 5.1 | 4.7 |

[1]average tablet weight calculation: (net wt (g)/50) × 100 = average tablet weight gain.
[2]actual % coat calculation: [(avg tab wt (mg) − initial avg. tab wt (mg))/initial avg tab wt (mg)] × 100%

10. Dissolution testing was conducted.

During the dissolution testing, tablets with 3.0% coat showed tablet matrix hydrating, breaking through coat around the tablet face/band periphery edge at 2 hours and 27 minutes.

Tablets with 4.0% overcoat, at 2 hours and 25 minutes into the dissolution run, appeared to break through around the tablet face/band periphery edge (i.e., the intersection of the side wall with each face), but still retain the tablet shape.

At the same time, tablets with 5.1% coat showed some areas of gel/hydration break through around the tablet face/band periphery edge (i.e., the intersection of the side wall with each face).

The dissolution results were entered into Excel and graphs were created for the coated monolithic tablets with (i) a 1.9% Opadry® subcoat or 0.24% Opadry® subcoat, and (ii) 1.5%, 1.7%, 2.4%, 3.0%, 3.6%, or 4% actual Surelease coatings were created. The graphs, and corresponding pictures (where available) are depicted in FIGS. 8 to 11.

Tablet 2 (4% surelease coat) released slower than Tablet 1 and 3 with 4% surelease coat, because the film coat remained intact around the face/band edge (i.e., the intersection of the side wall with each face). The picture of Tablet 2, side two, shows the tablet face film and band film still completely connected. This means that the tablet was held in a cup shaped film-coat that provided for slower release (less tablet was exposed to the media).

Example 5

Specialized toolings for creation of different structures, peaks or indentations on the surface of a dosage form core (i.e., punch tip faces) was designed, and ordered from Elizabeth Carbide Die Co., Inc.

Figure 12:
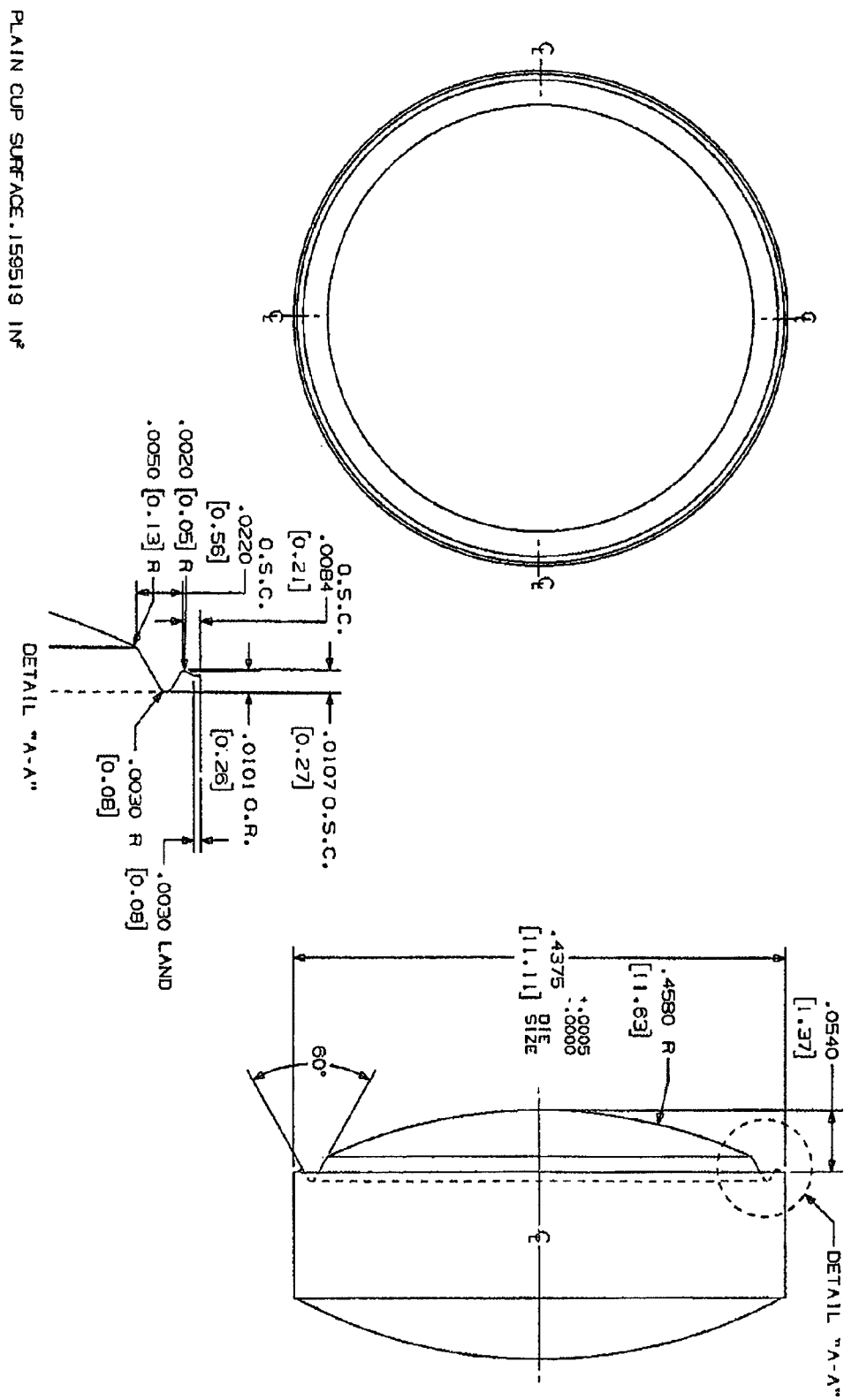
FIG. 12 is a drawing of a tablet core with a V-groove contour around periphery of the tablet face edge (drawing P-26644-A).

A punch tip face for creation of a tablet core having a surface with a structure in the form of a V-groove contour around periphery of the tablet face edge (i.e., the intersection of the side wall with a tablet face) was based on the drawing of the tablet core depicted in FIG. 12 (tooling drawing number P-266644-A).

Figure 13:
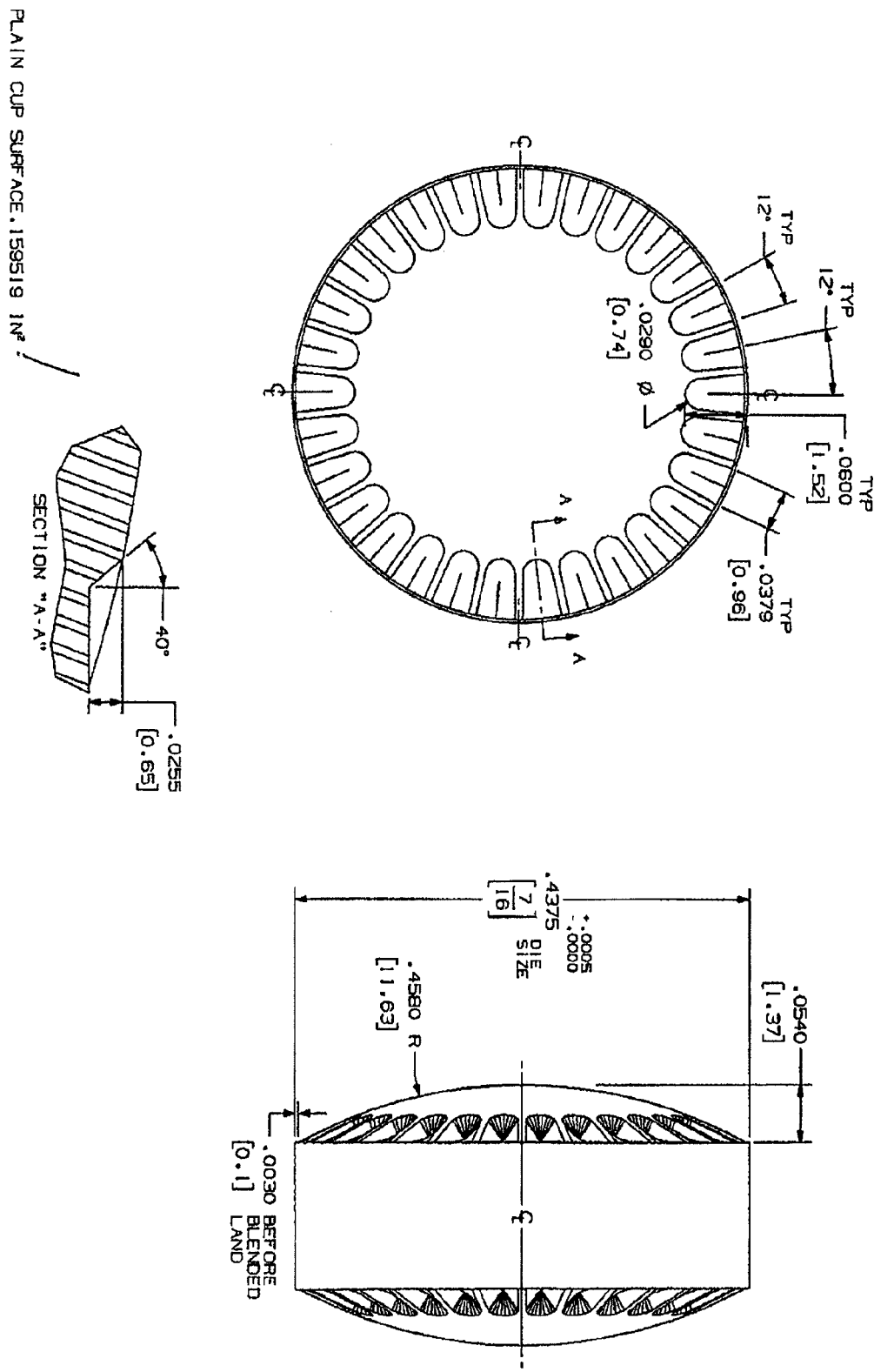
FIG. 13 is a drawing of a tablet core having a surface with peaks in the form of small serrations around the periphery of the tablet face edge that do not break the periphery edge of the punch (drawing P-26493-A).

A punch tip face for creation of a tablet core having a surface with peaks in the form of small serrations around the periphery of the tablet face edge, that do not break the periphery edge of the punch was designed based on the drawing of the tablet core depicted in FIG. 13 (tooling drawing number P-26493-A).

Figure 14:
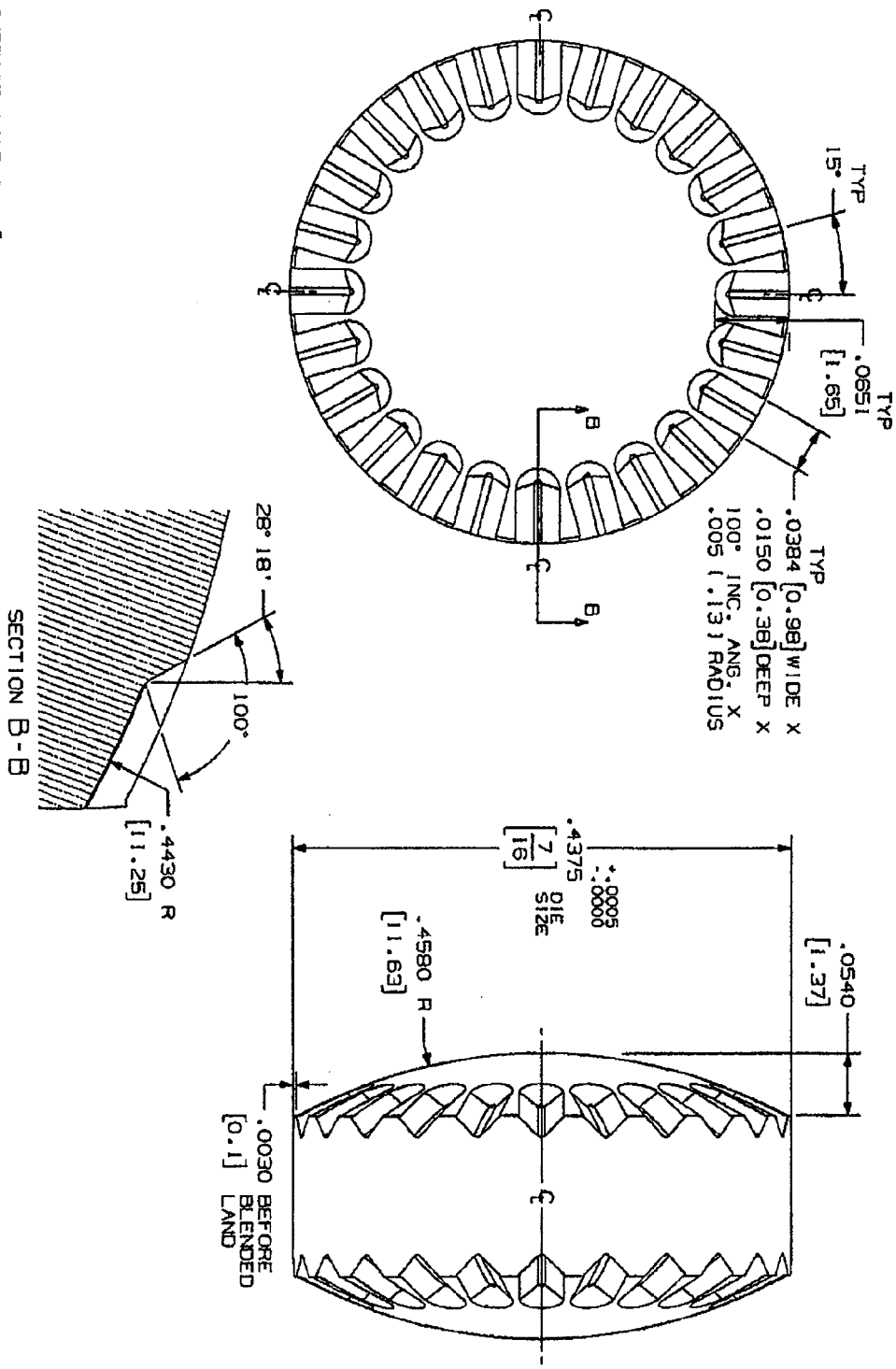
FIG. 14 is a drawing of a tablet with long serrated style groves around the periphery of the tablet face edge that break the face edge (drawing P-26494-A).

A punch tip face for creation of a tablet core having a surface with peaks and indentations in the form of long serrated style grooves around the periphery of the tablet face edge that break the face edge was ordered based on the drawing of the tablet core depicted in FIG. 14 (tooling drawing number P-26494-A).

Figure 15:
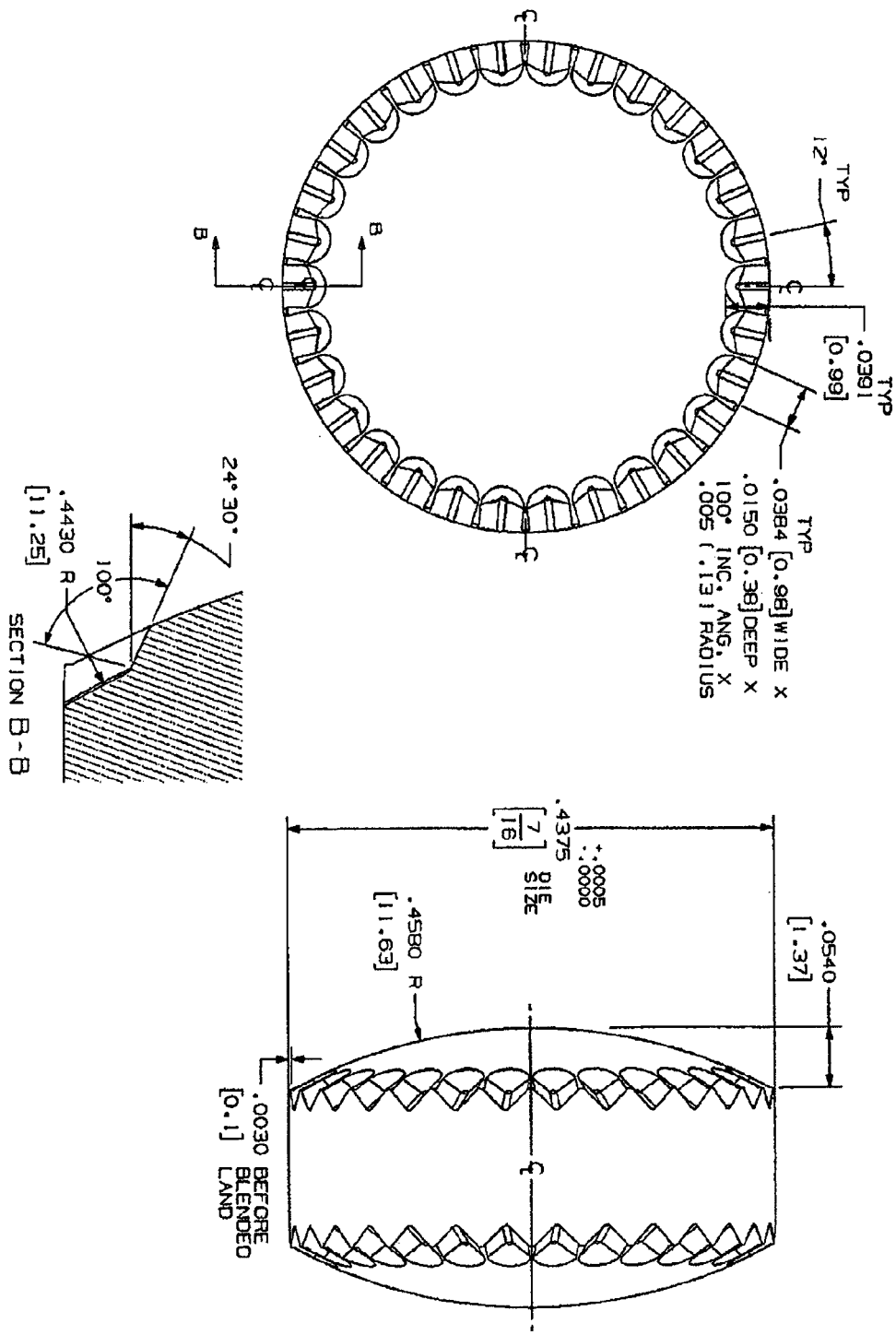
FIG. 15 is a drawing of a tablet core with short serrated style grooves around the periphery of the tablet face edge that break the face edge (drawing P-26495-A).

A punch tip face for creation of a tablet core having a surface with peaks and indentations in the form of short serrated style grooves around of the periphery of the tablet face edge that break the face edge was designed based on the drawing of the tablet core depicted in FIG. 15 (tooling drawing number P-26495-A).

An upper punch and a lower punch based on the punch tip faces described above (P-266644-A, P-26493-A, P-26494-A, P-26495-A) were ordered for a single station F3 Press (Manesty).

Example 6

1. Hydrocodone bitartrate granulation of the formulation set forth in Table 17 were prepared. Portions of each granulation were used to prepare a tablet blend set forth in Table 18.

TABLE 17

Formulation for Granulations Used Above
(Lot Number 1667-71, 1667-78, 1667-92

| Ingredient | mg/unit | Actual Amt Used (g) |
|---|---|---|
| Hydrocodone Bitartrate, USP | 120 | 660 |
| Hydroxypropyl Cellulose (Klucel EXF) | 8.18 | 45 |
| Microcrystalline Cellulose, NF (Avicel PH 101) | 8.18 | 45 |
| Total | 136.36 | 750 |
| Water, USP Purified * | | 180 |

* Removed during the drying process

TABLE 18

| Formulation: - Tablet Blend (target 120 mg/500 mg tablets) | | | | | | |
|---|---|---|---|---|---|---|
| Ingredient | mg/unit | Theoretical Amount (g) | Actual Amt Used (g) | Lot Number | Other info | |
| Milled HYD granulation | 136.36 (27.27%) | 681.75 | 682.32 | 1667-71 1667-78 1667-92 | 508.17 93.34 80.81 | Theoretical assay: 120 mg/ 136.36 mg |
| PEO 303 | 361.14 (72.23%) | 1805.75 | 1805.8 | XI2255S5R3 | LEO,viscosity 7860 cps (per CoA) | |
| Magnesium Stearate | 2.5 (0.5%) | 12.5 | 12.5 | C908740 | vegetable grade; Peter Greven | |
| Total | 500 | 2500 | 2500.62 | | | |

2. The hydrocodone bitartrate milled granulation and approximately half of the PEO were added to the 8 qt V-blender, and then the remaining PEO was added. These components were mixed for 5 minutes, NO I-bar.

3. Magnesium stearate (screened through a 20-mesh screen) was added, and mixed for 1 minute, NO I-bar.

4. A single station F3 tablet press was used to compress 500 mg tablets core (each containing 120 mg of hydrocodone bitartrate), using the specialized tooling (punch tip faces) described in Example 5. In addition, in Run 5 a control set of cores were compressed, using a conventional 7/16 inch (11 mm), round standard concave tooling (plain, no indicia). Five Runs were made.

Figure 16:
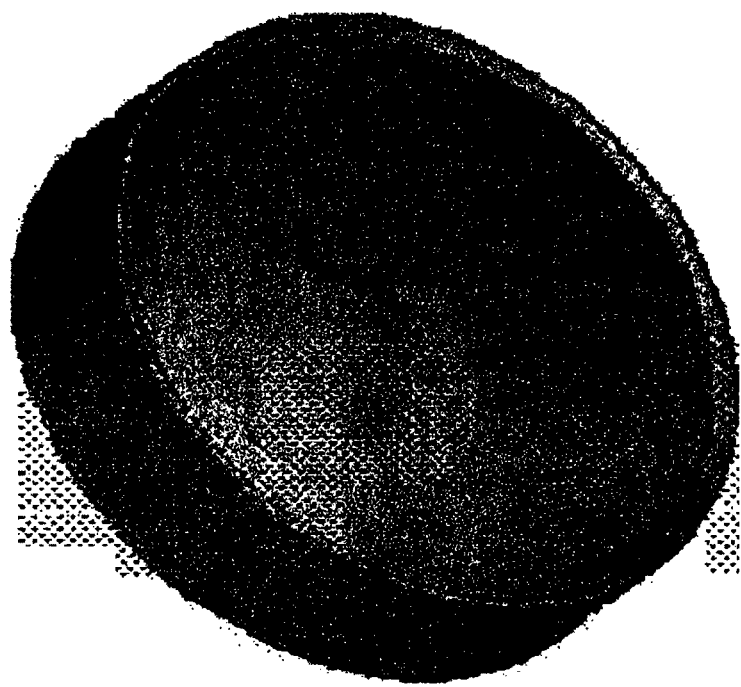
FIG. 16 is a computerized image of a tablet core compressed with a tooling design based on drawing P-26644-A.

In Run 1, compression with the tooling designed based on drawing number P-26644-A and using an upper punch depth setting of 27.5 mm resulted in a compressed tablet core having a surface with a structure in the form of a V-groove contour around periphery of the tablet face edge. A drawing of the tablet core produced in this Run is depicted in FIG. 16. 392.6 grams of tablet cores were produced. The weight, thickness and hardness of the tablet cores produced in this run are depicted in Table 19 (n=5).

TABLE 19

| Weight (mg) | | | | | Thickness (mm) | | | | | Hardness (Kp) | | | | |
|---|---|---|---|---|---|---|---|---|---|---|---|---|---|---|
| 505.5 | 507.1 | 508.6 | 507.4 | 507.3 | 6.03 | 6.05 | 6.03 | 6.05 | 6.05 | 20+ | 20+ | 20+ | 20+ | 20+ |

Figure 17:
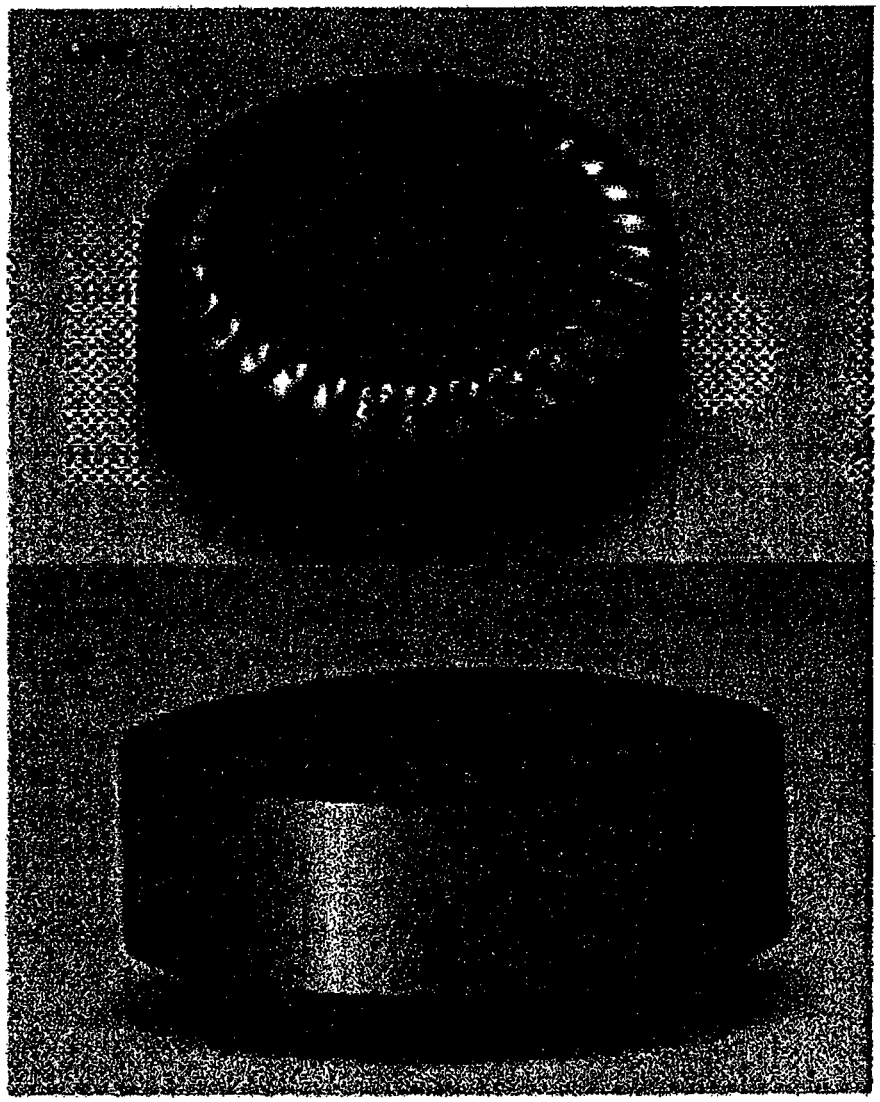
FIG. 17 is a computerized image of a tablet core compressed with a tooling design based on drawing P-26493-A.

In Run 2, compression with the tooling based on drawing number P-26493-A and using upper punch depth setting of 25.0 mm resulted in compressed tablet cores having surfaces with peaks and indentations in the form of small serrated style grooves around the periphery of the tablet face edge that do not break the periphery edge. A computerized image of the tablet core produced in this run is depicted in FIG. 17. 391.5 grams of tablet cores were produced. The weight, thickness and hardness of the tablet cores produced in this run are depicted in Table 20 (n=5).

TABLE 20

| Weight (mg) | | | | | Thickness (mm) | | | | | Hardness (Kp) | | | | |
|---|---|---|---|---|---|---|---|---|---|---|---|---|---|---|
| 503.4 | 505.0 | 504.9 | 506.4 | 506.0 | 6.26 | 6.24 | 6.24 | 6.25 | 6.24 | 20+ | 20+ | 20+ | 20+ | 20+ |

Figure 18:
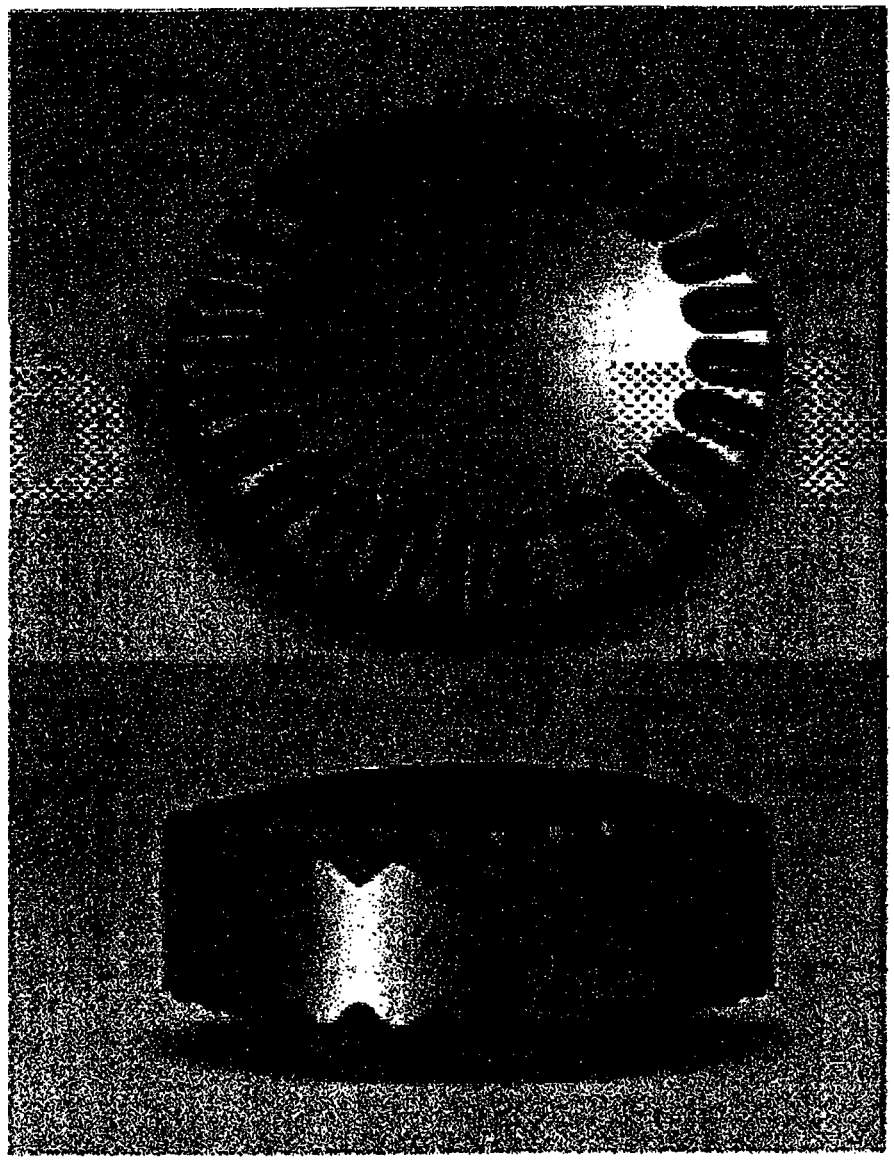
FIG. 18 is a computerized image of a tablet core compressed with a tooling design based on drawing P-26494-A.

In Run 3, compression with the tooling based on drawing number P-26494-A and using upper punch depth setting of 27.0 mm resulted in a tablet core having a surface with peaks and indentations in the form of long serrated style groves around the periphery of the tablet face edge that break the face edge. A computerized image of the tablet core produced in this run is depicted in FIG. 18. 427.5 grams of tablet cores were produced. The weight, thickness and hardness of the tablets produced in this run are depicted in Table 21 (n=5).

TABLE 21

| Weight (mg) | | | | | Thickness (mm) | | | | | Hardness (Kp) | | | | |
|---|---|---|---|---|---|---|---|---|---|---|---|---|---|---|
| 503.8 | 503.0 | 501.3 | 502.0 | 501.8 | 6.25 | 6.30 | 6.25 | 6.26 | 6.25 | 20+ | 20+ | 20+ | 20+ | 20+ |

Figure 19:
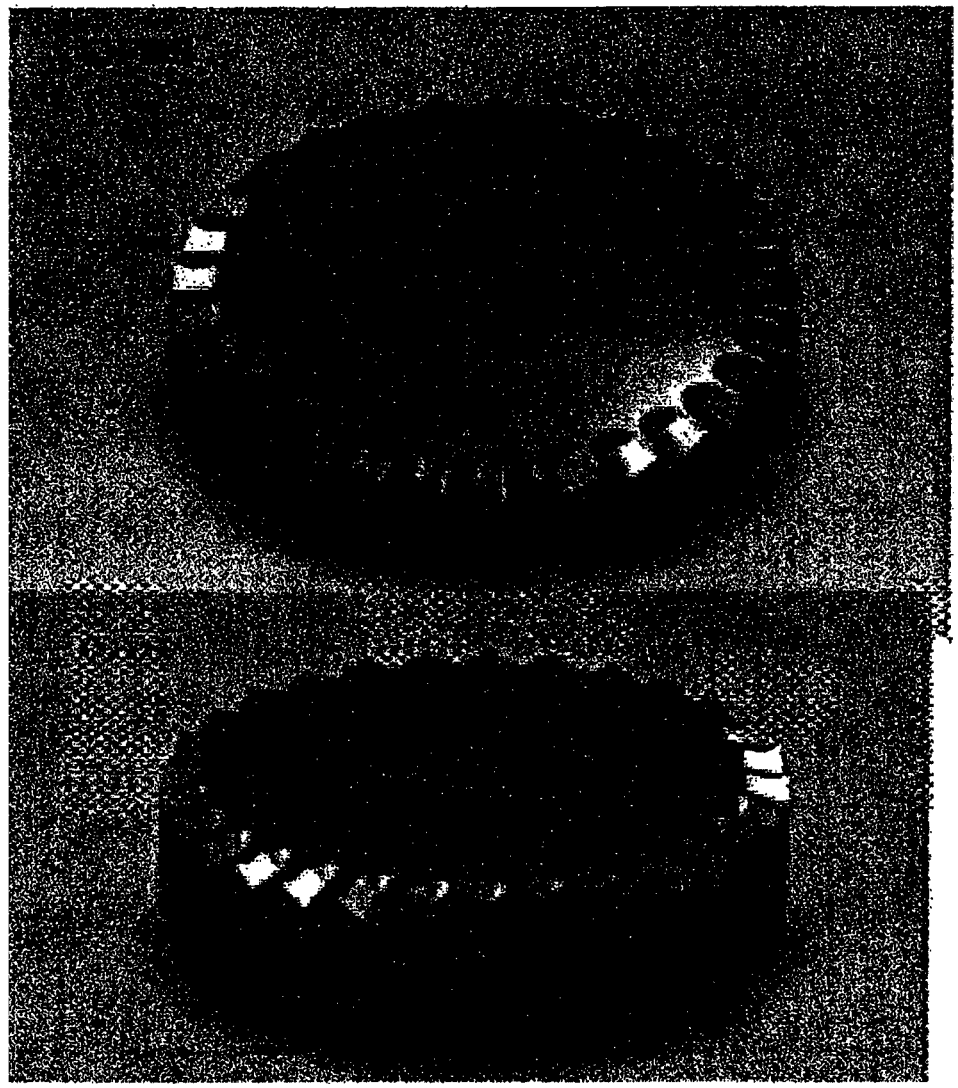
FIG. 19 is a computerized image of a tablet core compressed with a tooling design based on drawing P-26495-A.

In Run 4, compression with the tooling based on drawing number P-26495-A and using upper punch depth setting of 26.5 mm resulted in a tablet core having a surface with peaks and indentations in the form of short serrated style grooves around the periphery of the tablet face edge that break the face edge. A computerized image of the tablet core produced in this run is depicted in FIG. 19. 391.6 grams of tablet cores were produced. The weight, thickness and hardness of the tablets produced in this run are depicted in Table 22 (n=5).

TABLE 22

| Weight (mg) | | | | | Thickness (mm) | | | | | Hardness (Kp) | | | | |
|---|---|---|---|---|---|---|---|---|---|---|---|---|---|---|
| 505.7 | 509.4 | 508.1 | 507.7 | 504.3 | 6.30 | 6.32 | 6.33 | 6.30 | 6.29 | 20+ | 20+ | 20+ | 20+ | 20+ |

In Run 5, compression with 7/16 inch (11 mm), round standard concave die (plain, no indicia) resulted in a tablet having substantially uniform concave surface. The weight, thickness and hardness of the tablets produced in this run are depicted in Table 23 (n=5).

TABLE 23

| Weight (mg) | | | | | Thickness (mm) | | | | | Hardness (Kp) | | | | |
|---|---|---|---|---|---|---|---|---|---|---|---|---|---|---|
| 508.6 | 505.3 | 509.3 | 507.8 | 506.5 | 6.28 | 6.27 | 6.25 | 6.26 | 6.28 | 20+ | 20+ | 20+ | 20+ | 20+ |

6. The tablet cores from Run 1 and 2 were cured for 30 minutes at target exhaust 72° C. in a 15 inch coating pan. The curing information for tablet cores compressed with dies based on drawing number P-26644-A and drawing number P-26493-A is set forth in Table 24.

TABLE 24

| Time (min) | Temperature (° C.) | | | Air vol Cfm | Pan size 15 | |
| | Inlet Set | Inlet Actual | Exhaust | | Pan Rpm | inches Comments |
|---|---|---|---|---|---|---|
| 0 | 22/85 | 20.1 | 19.0 | 302 | 9.2 | Load tablets, start warming |
| 18.5 | 85 | 85.2 | 72.0 | 284 | 11.2 | Start curing |
| 33.5 | 79 | 78.8 | 72.0 | 280 | 11.2 | Tablets sticky, shorting cascade bed flow, a lot of tablets bouncing our of pan |
| 48.5 | 78.5 | 78.3 | 72.2 | 282 | 11.2/9.0 | Add 0.791 g of Mg stearate, start cooling, inlet set to 22° C. |
| 64 | 22 | 22.9 | 29.6 | 302 | 8.0 | End cooling, no sticking, observed during cool down |

The "stickiness" of the tablets during curing was addressed by dusting the tablets with magnesium stearate prior to cooling. Stickiness could also be eliminated or minimized by using a sub-coat of Opadry®.

7. A 10% solids dispersion of Surelease Clear® E-7-19040 (aqueous ethylcellulose dispersion) was prepared by mixing 200 grams of Surelease Clear® E-7-19040 with 300 grams of deionized water.

8. 150 grams of cured tablet cores from Run 1 were loaded into a 0.5 liter tablet coating pan (Vector LDCS). The tablet cores were warmed and sprayed with 45 grams of the 10% solids Surelease Clear® E-7-19040 dispersion. The spraying resulted in a weight gain of 2.9% (target 3%). The pan speed was 30 rpm, air flow 30 cfm, target spray rate 3 g/min, tablet bed temperature 38-41° C. The sprayed tablet cores were cooled for approximately 5 minutes and transferred to an oven at 40° C. for approximately 15 minutes.

9. 150 g of cured tablet cores from Run 2 were loaded into a 0.5 liter tablet coating pan (Vector LDCS) and warmed. 45 grams of the 10% solids Surelease Clear® E-7-19040 dispersion was sprayed onto the tablet cores. The spraying resulted in a weight gain of 3.0% (target 3%). The pan speed was 30 rpm, air flow 30 cfm, target spray rate 3 g/min, tablet bed temperature 38-41° C. The coated cores were cooled for approximately 5 minutes. After cooling, the coated tablet cores were transferred to an oven and held at 40° C. for approximately 15 minutes.

8. 40 grams of Opadry II Purple 33G100003 was mixed with 360 grams of deionized water to prepare 10% solids Opadry® dispersion.

Tablet cores from Run 3, 4 and 5 (150 grams of tablet cores from each run) were loaded into three 0.5 liter tablet coating pan (Vector LDCS), each pan having tablet cores from either Run 3, Run 4 or Run 5. The tablet cores were warmed and sprayed with 20 grams of the 10% solids Opadry® dispersion. The spraying resulted in a weight gain of 1.0% (target 1%).

9. The tablet cores coated with the 10% solids Opadry® coating dispersion were cured for 37 minutes in an oven at 72° C. The 10% solids Opadry® coating would serve as a sub-coat (i.e., a coating between the tablet core and the primary coating) in the dosage form.

10. After curing, the coated tablet cores (150 grams of coated cured cores from each of Run 3, 4 or 5) were loaded into three 0.5 liter tablet coating pan (Vector LDCS), each having tablet cores from either Run 3, Run 4 or Run 5. The tablet cores were warmed and sprayed with 45 grams of the 10% solids Surelease Clear® E-7-19040 dispersion. The pan speed was 30 rpm, air flow 30 cfm, target spray rate 3 g/min, tablet bed temperature 38-41° C. The coated, cured tablet cores from Run 3 were sprayed to a weight gain of 3.2%. The coated, cured tablet cores from Run 4 were sprayed to a weight gain of 2.6%. The coated, cured tablet cores from Run 5 were sprayed to a weight gain of 2.7%.

11. The tablet cores sprayed with the 10% solids Surelease Clear® E-7-19040 dispersion were cooled for approximately 5 minutes and transferred to an oven at 40° C. for approximately 15 minutes.

Figure 20:
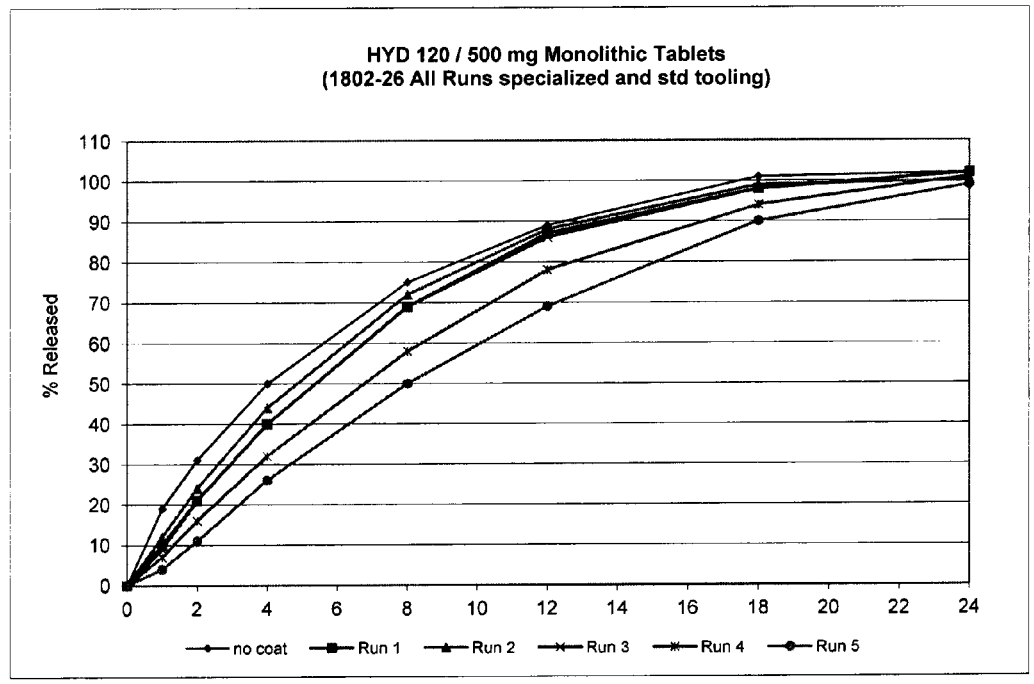
FIG. 20 a graph showing the results of dissolution testing of the coated cured tablet cores of Example 6.

12. The dissolution testing of the resulting coated cured tablet cores of Runs 1-5 was conducted. The results of the dissolution are provided in Table 25, and are graphically shown in FIG. 20.

TABLE 25

| | Uncoated Tablet from Run 2 | Run 1 | Run 2 | Run 3 | Run 4 | Run 5 |
|---|---|---|---|---|---|---|
| 0 | 0 | 0 | 0 | 0 | 0 | 0 |
| 1 | 19 | 10 | 12 | 9 | 7 | 4 |
| 2 | 31 | 21 | 24 | 21 | 16 | 11 |
| 4 | 50 | 40 | 44 | 40 | 32 | 26 |
| 8 | 75 | 69 | 72 | 69 | 58 | 50 |
| 12 | 89 | 87 | 88 | 86 | 78 | 69 |
| 18 | 101 | 98 | 99 | 98 | 94 | 90 |
| 24 | 102 | 102 | 100 | 102 | 101 | 99 |

Example 7

The coated cured tablet cores of Run 4 and Run 5 of Example 6 were used in two tablet hydration studies. During the hydration studies, the coated cured tablet cores were placed in SGF fluid and photographed at various time points. Photographs from the first hydration study are depicted in FIGS. 21A-21G. Photographs from the second hydration study are depicted in FIGS. 22A-22I.

The coated cured tablet cores of Run 4 had a surface with peaks and indentations in the form of short serrated style grooves around the periphery of the tablet face edge. The coated cured tablet cores of Run 5 had substantially uniform concave surface that broke the face edge. The coated cured tablet of both runs had cracks in the Opadry sub-coat along the tablet core's band before these tablets were placed in SGF fluid. Some or all of these cracks were formed in the Opadry coat during the curing process due to thermal expansion of the tablet and are visible, e.g., in Pic 1-4, Pic 1-5, Pic 2-4 and Pic 2-5 of FIGS. 21A and 22A. The affinity of the Surelease to adhere to the tablet core may have been a factor also. It is believed that formation of these cracks may be prevented or minimized by increasing the amount of the Opadry® coating and/or by increasing the amount of the Surelease coating. It is also believed that any formed cracks may be eliminated by applying additional Opadry coating after curing. The additional Opadry coating may be applied under and/or above the Surelease coating.

Figure 21A:
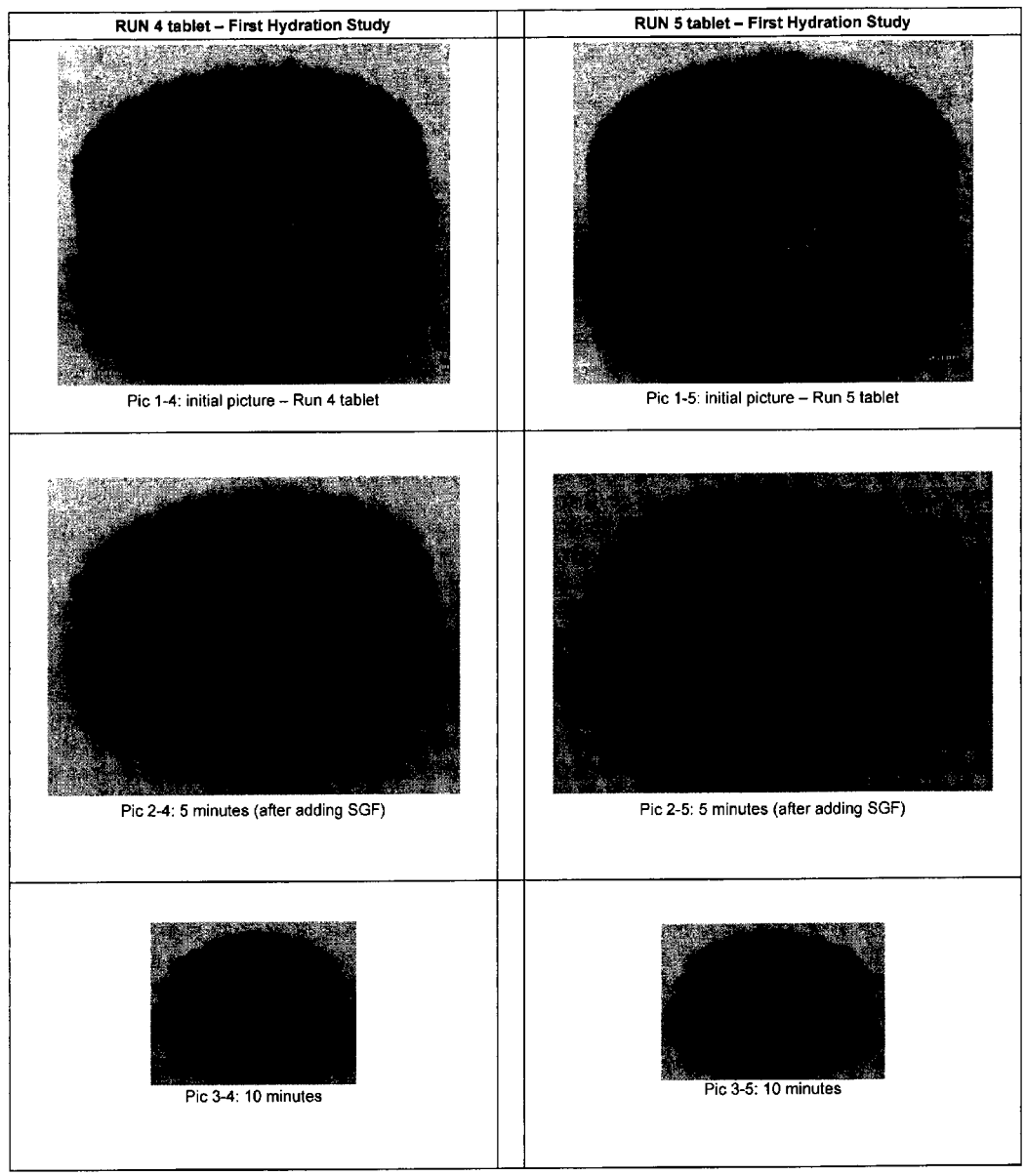
FIGS. 21A-21G are photographs from the first hydration study of Example 7 of Run 4 and 5 tablets. In Pic 1-4, initial picture—Run 4 tablet, Opadry subcoat cracks are visible along the tablet band, these cracks formed during the curing process due to thermal expansion of the tablet. In Pic 1-5, initial picture—Run 5 tablet, cracks in the Opadry subcoat are visible along the tablet band, these cracks formed during the curing process due to thermal expansion of the tablet. In Pic 2-4: 5 minutes (after adding SGF) the red oval shows that the media is penetrating through the cracks around the tablet band; apparently the surelease coating did not adequately coat/cover these areas to impede media penetration. The black arrow shows that the media is also penetrating at passageways formed immediately above or proximal to the structures around the periphery of the tablet face edge. In Pic 2-5, 5 minutes (after adding SGF), the media is penetrating through the cracks around the tablet band; apparently the surelease coating did not adequately coat/cover these areas to impede media penetration. This picture does not show any passageways around the periphery of the tablet face edge.
Figure 21B:
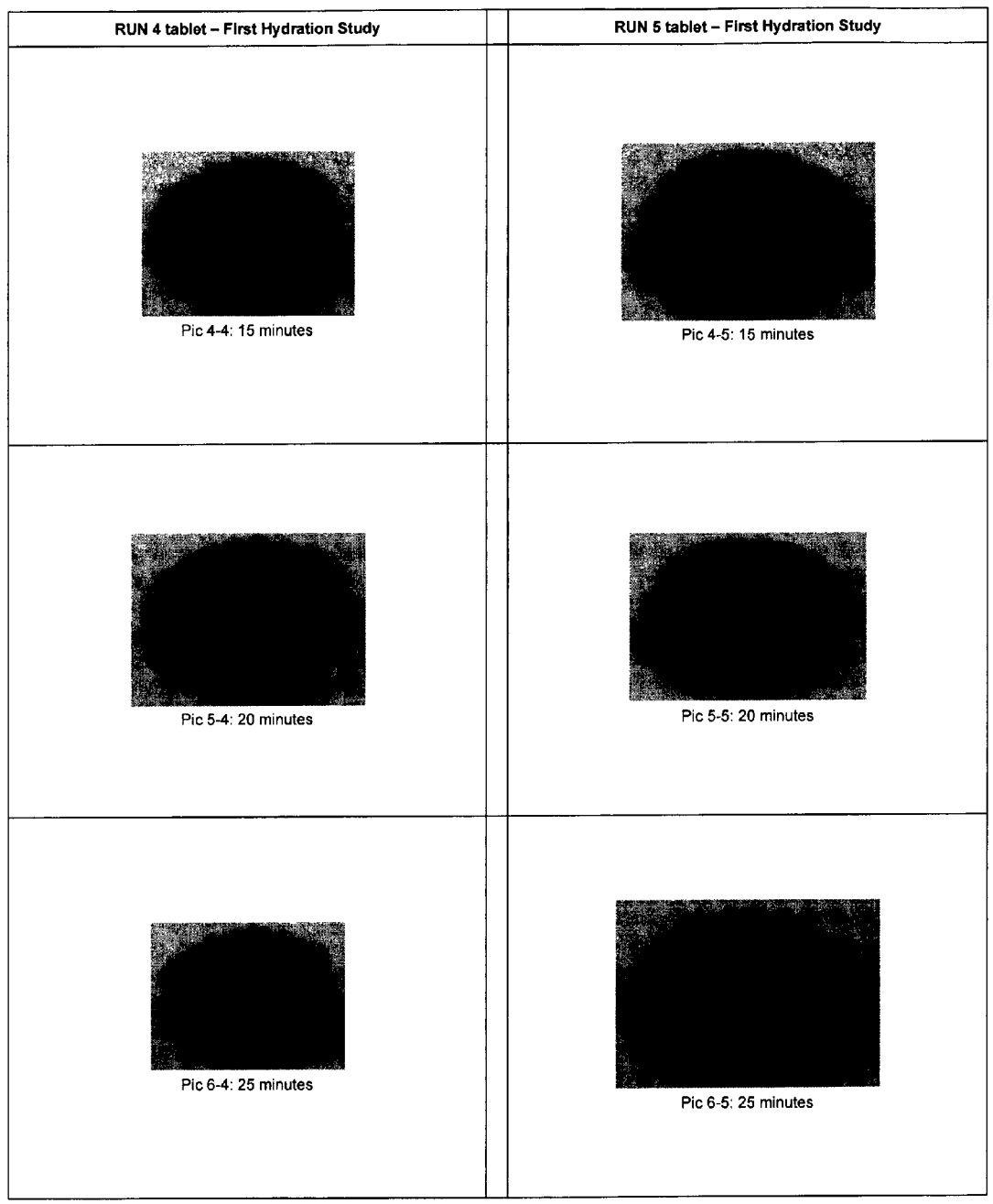
Figure 21C:
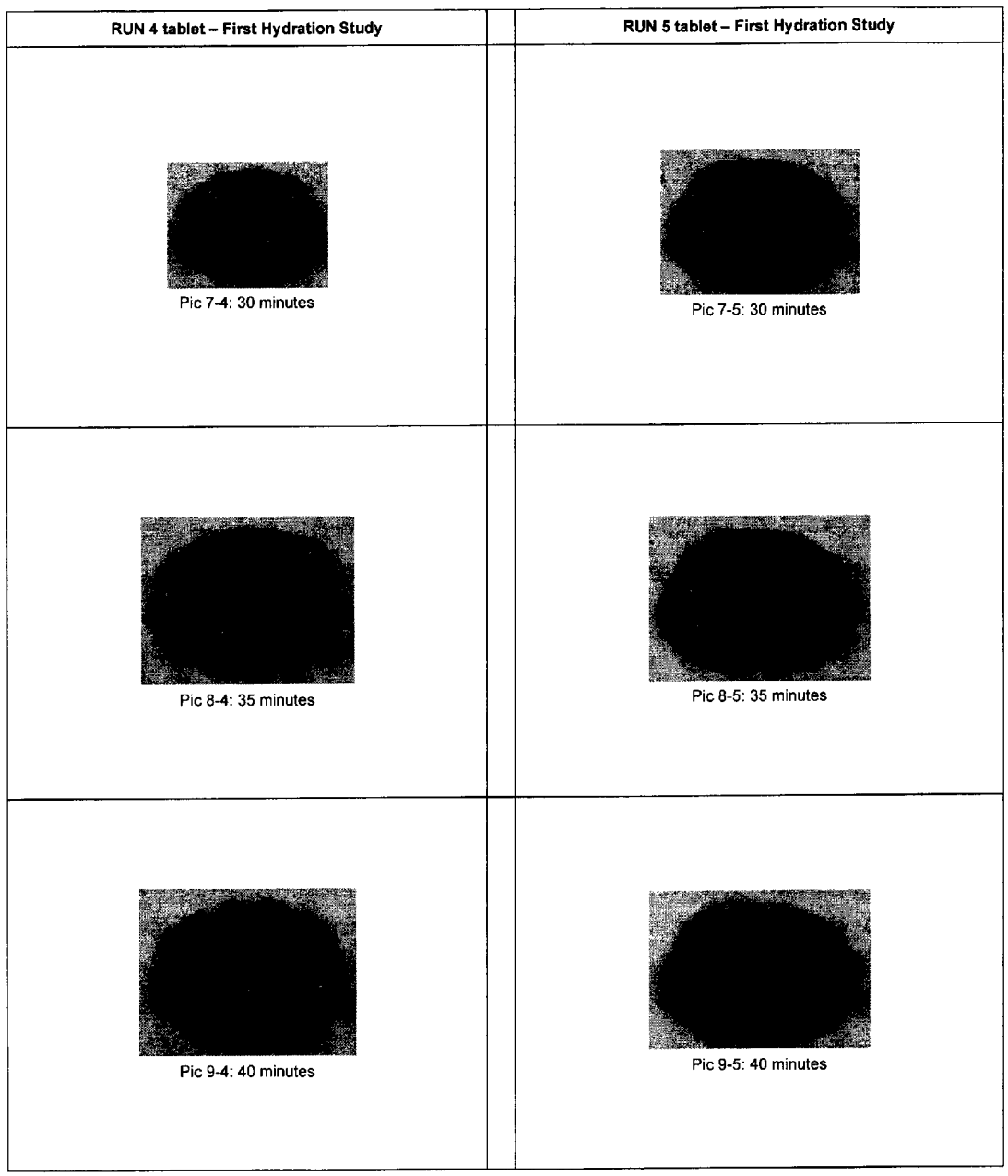
Figure 21D:
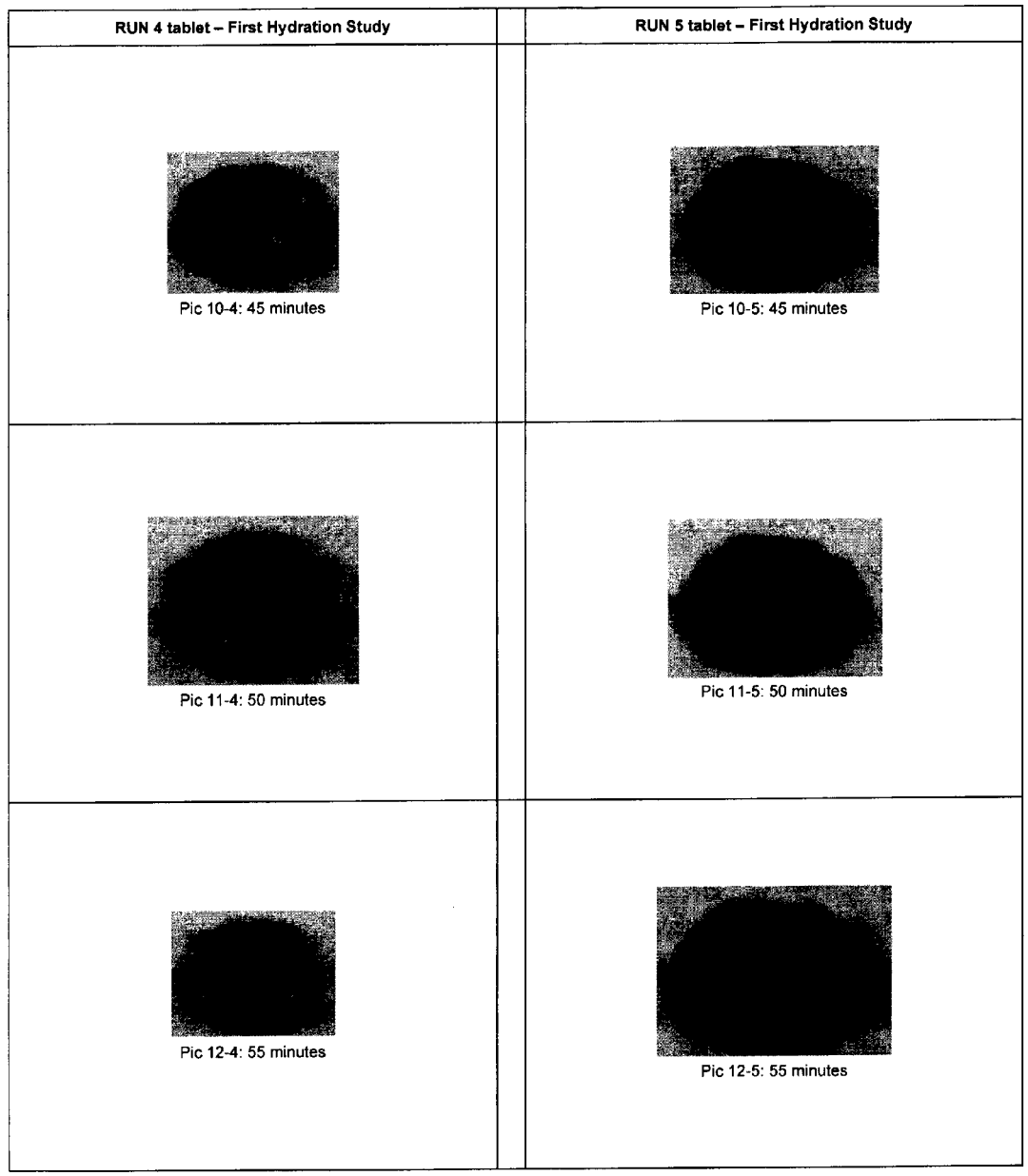
Figure 21E:
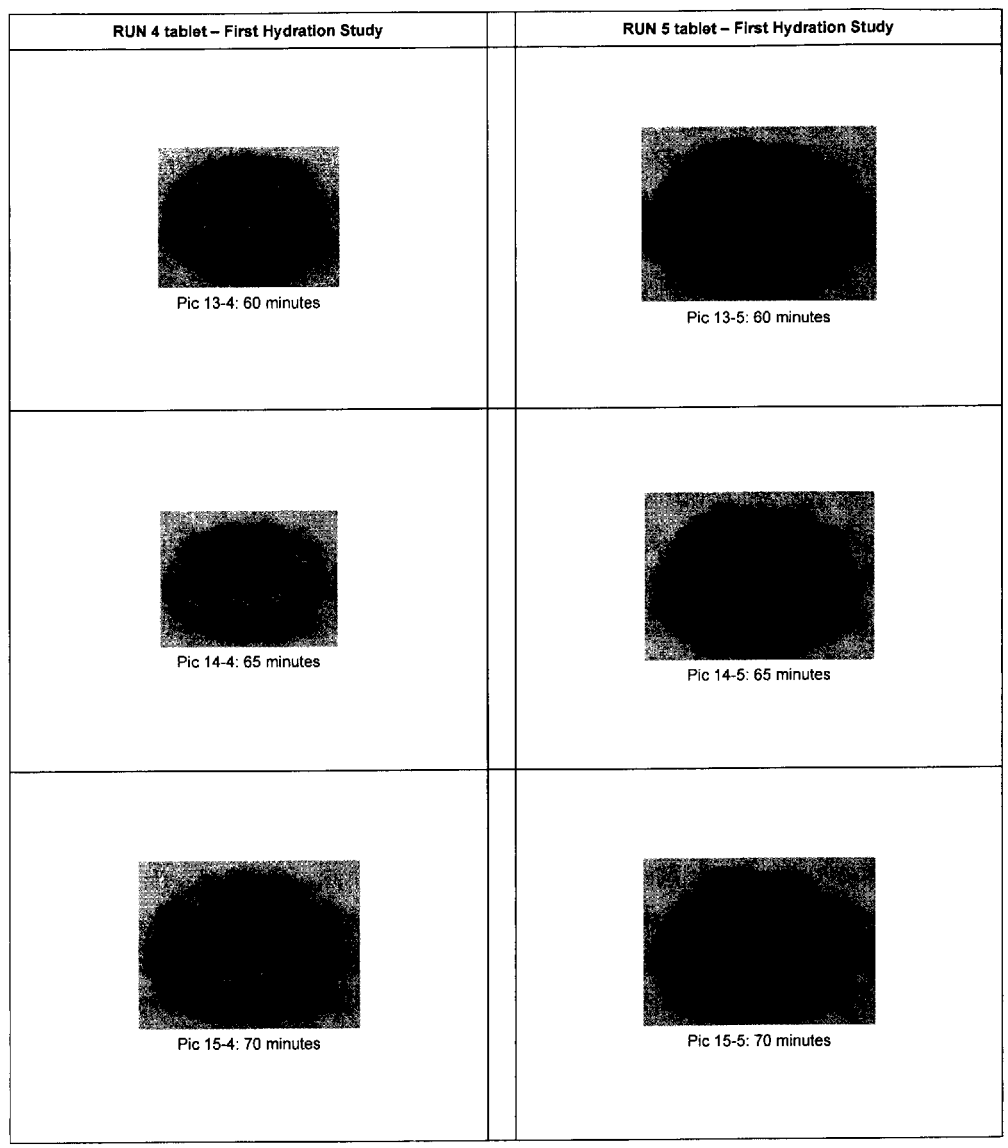
Figure 21F:
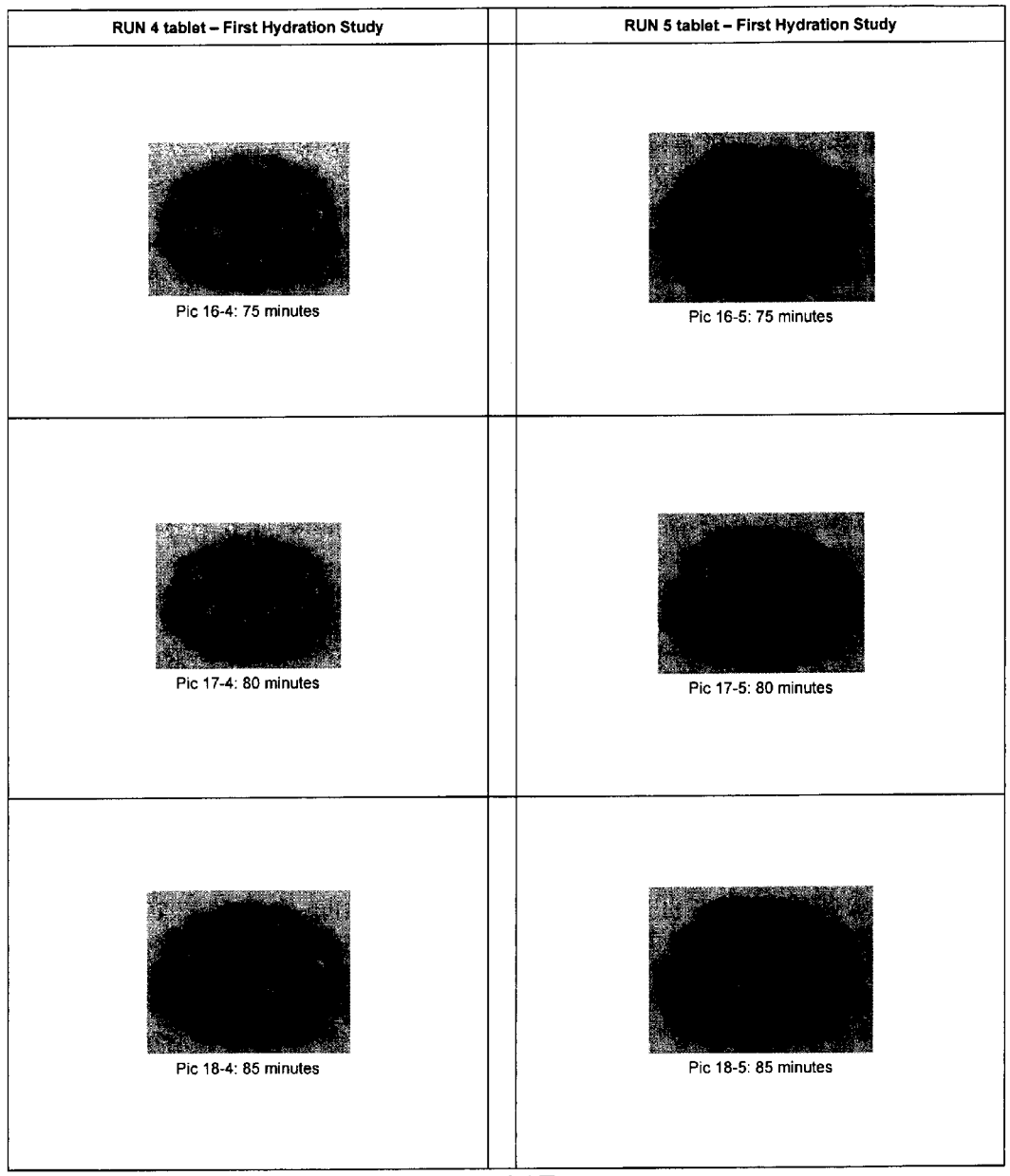
Figure 21G:
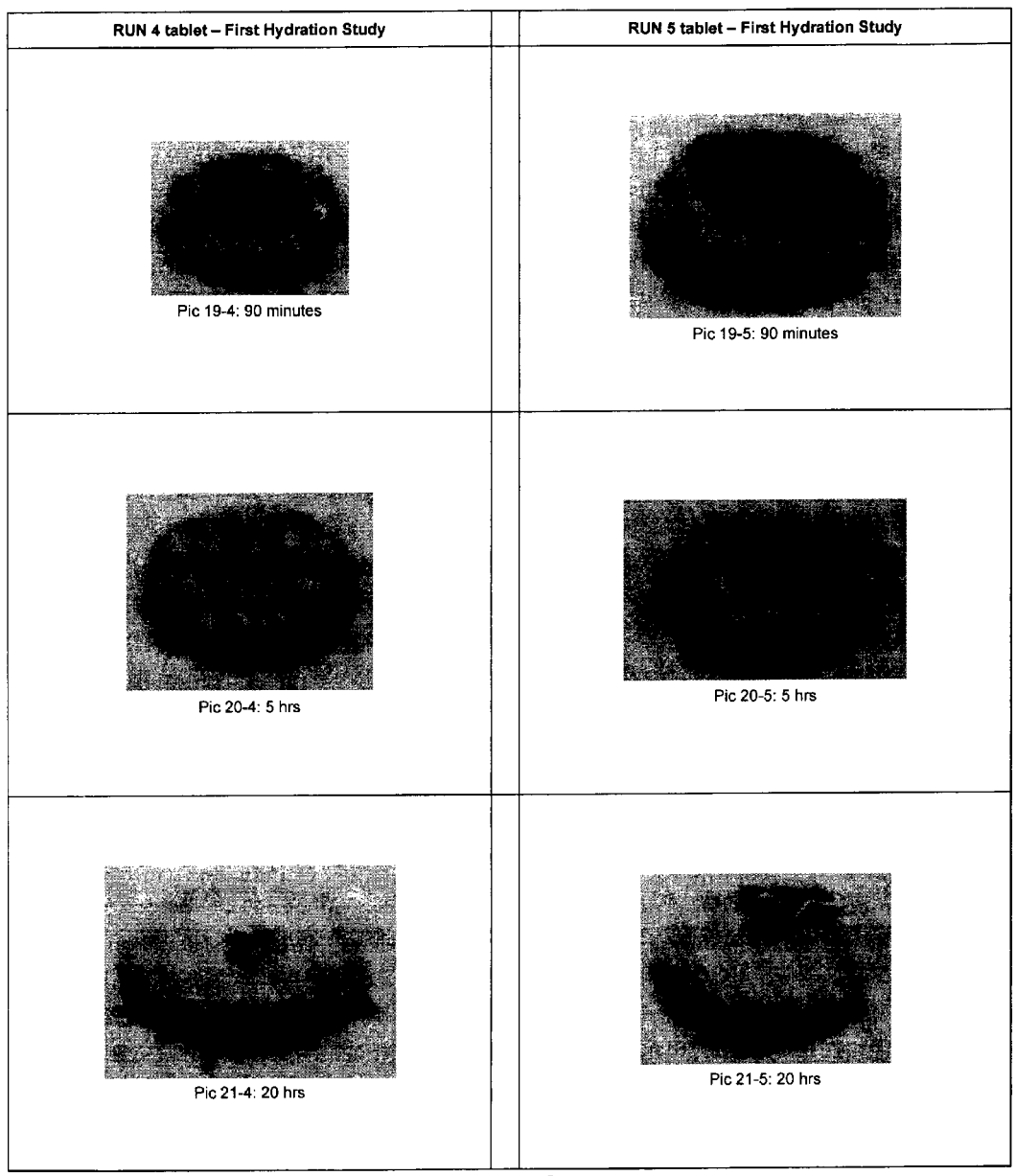
Figure 22A:
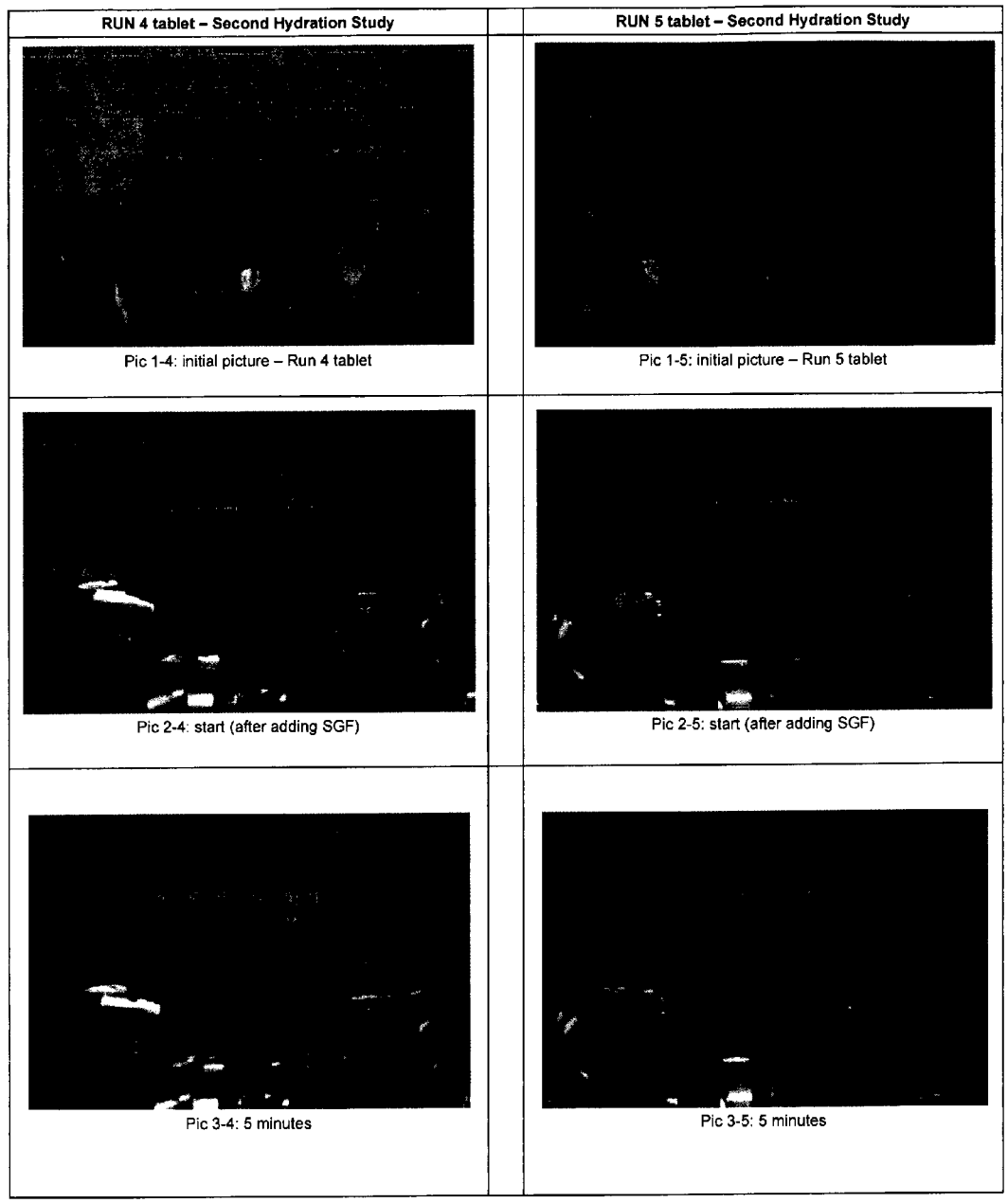
FIGS. 22A-22I are photographs from the second hydration study of Example 7 of Run 4 and 5 tablets. In Pic 1-4, the initial of Run 4 and 5 tablets, Run 4 tablet cracks in the Opadry subcoat are visible along the tablet band, these cracks formed during the curing process due to thermal expansion of the tablet. In Pic 1-5, initial picture, Run 5 tablet, cracks in the Opadry subcoat are visible along the tablet band, these cracks formed during the curing process due to thermal expansion of the tablet. In Pic 2-4, start (after adding SGF), cracks in Opadry subcoat along the tablet band are visible. In Pic 2-5, start (after adding SGF), cracks in Opadry subcoat along the tablet band are visible. In Pic 3-4, 5 minutes, the red oval shows that the media is penetrating through the cracks around the tablet band. Apparently the surelease coating did not adequately coat/cover these areas to impede media penetration. The black arrow shows that the media is also penetrating passageways formed immediately above or proximal to the structure points around the periphery of the tablet face edge. In Pic 3-5, 5 minutes, the media is penetrating through the cracks around the tablet band; apparently the surelease coating did not adequately coat/cover these areas to impede media penetration. The red circle shows that the media is also penetrating at a passageway on the tablet face edge.
Figure 22B:
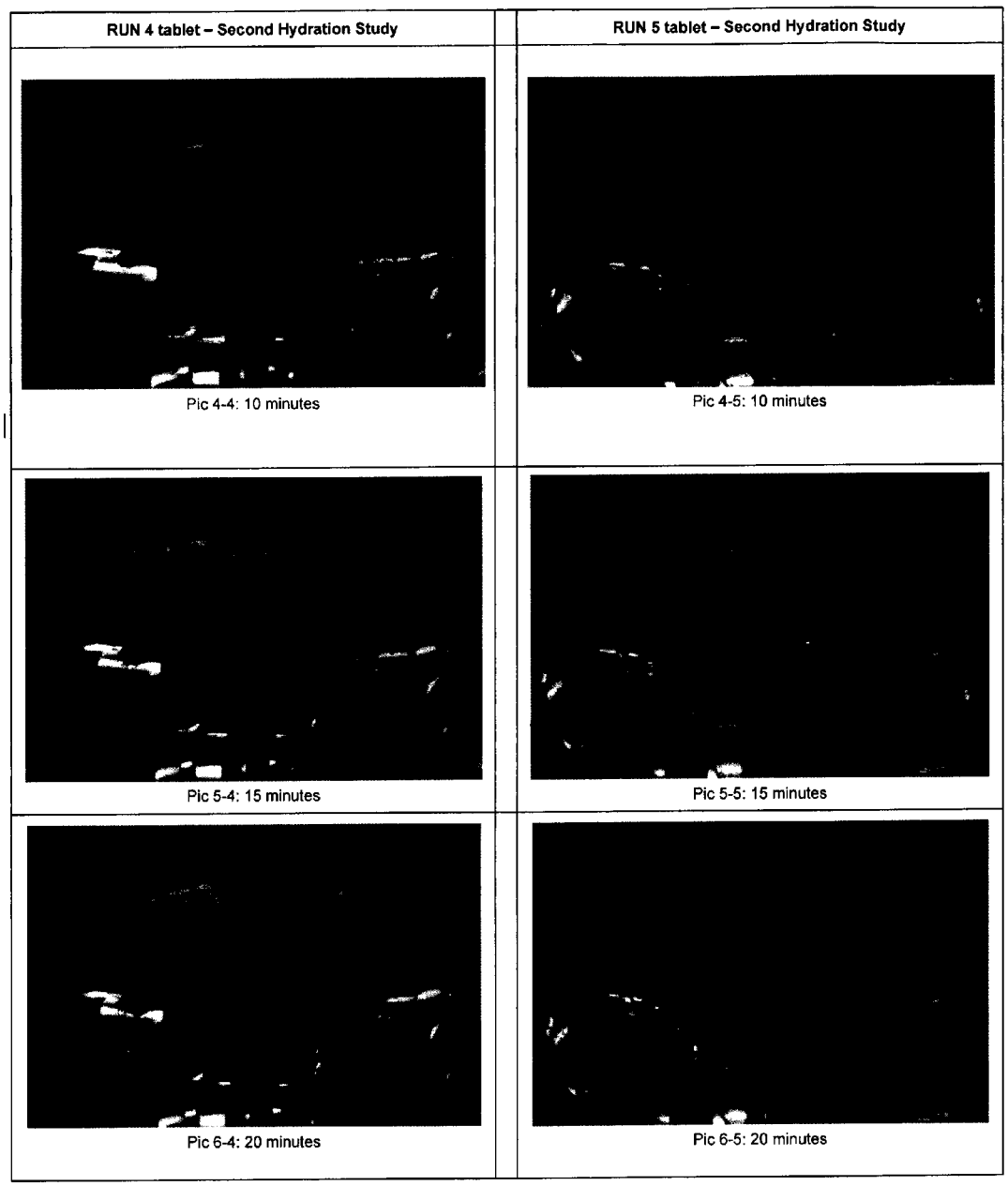
Figure 22C:
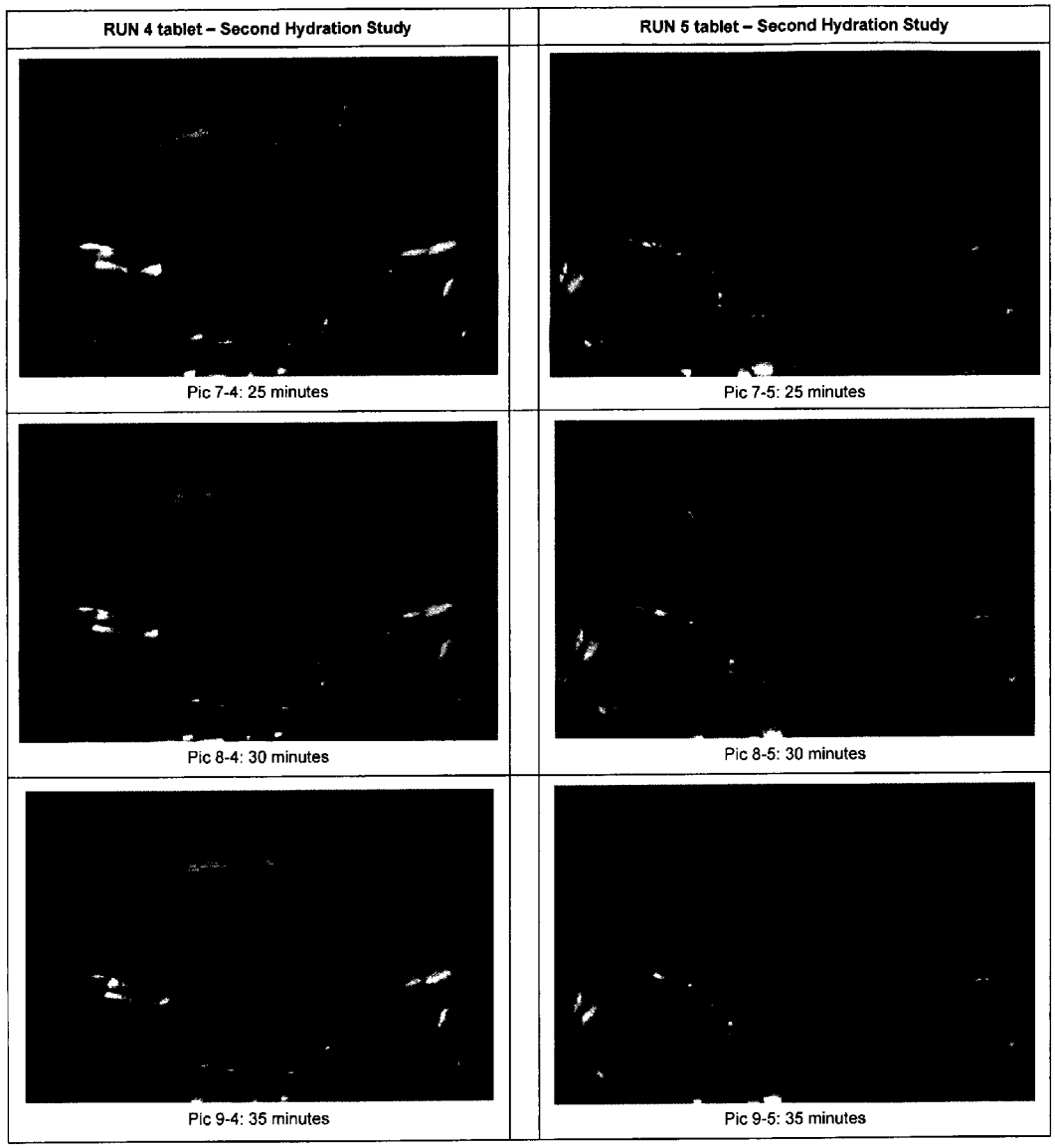
Figure 22D:
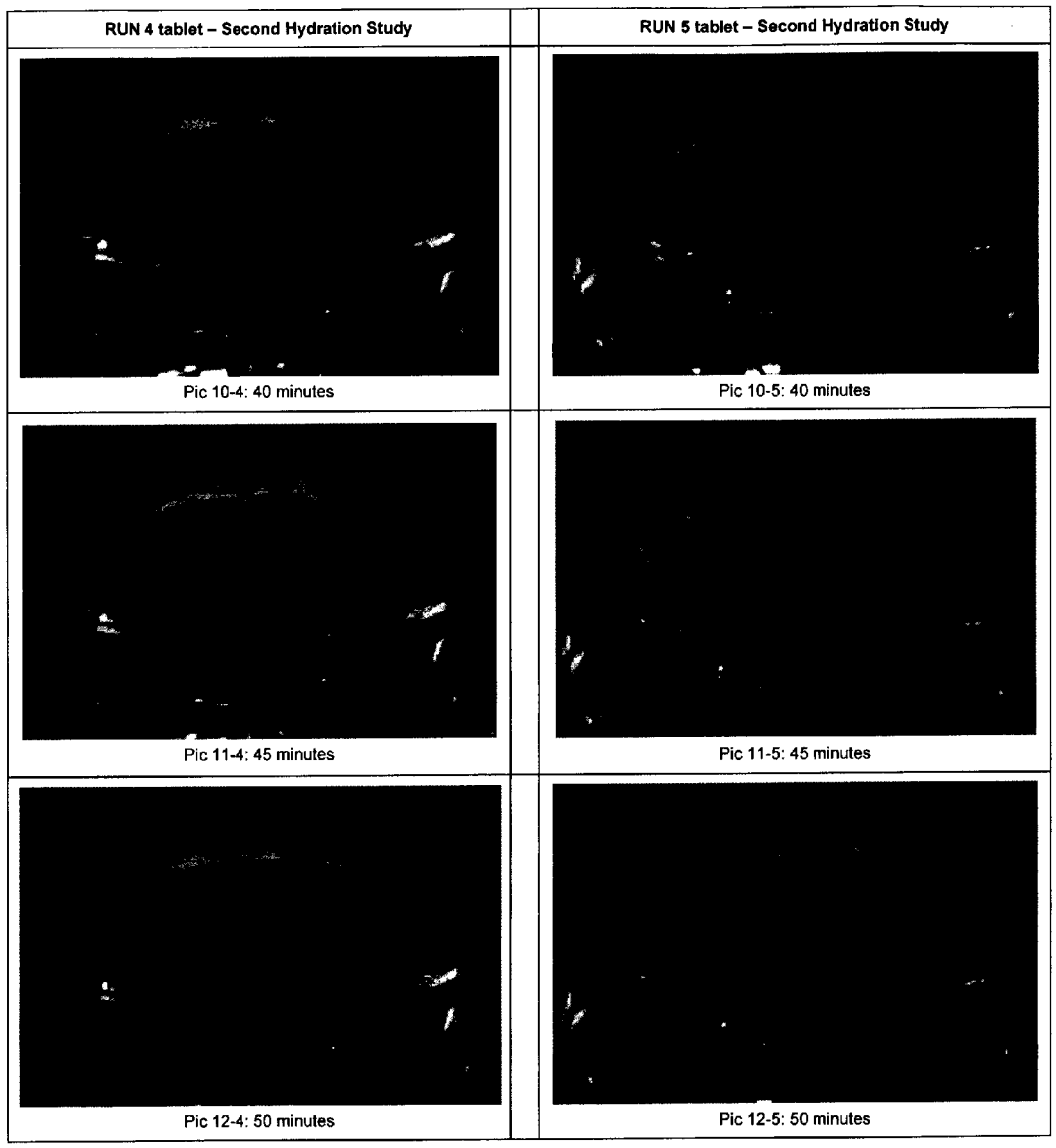
Figure 22E:
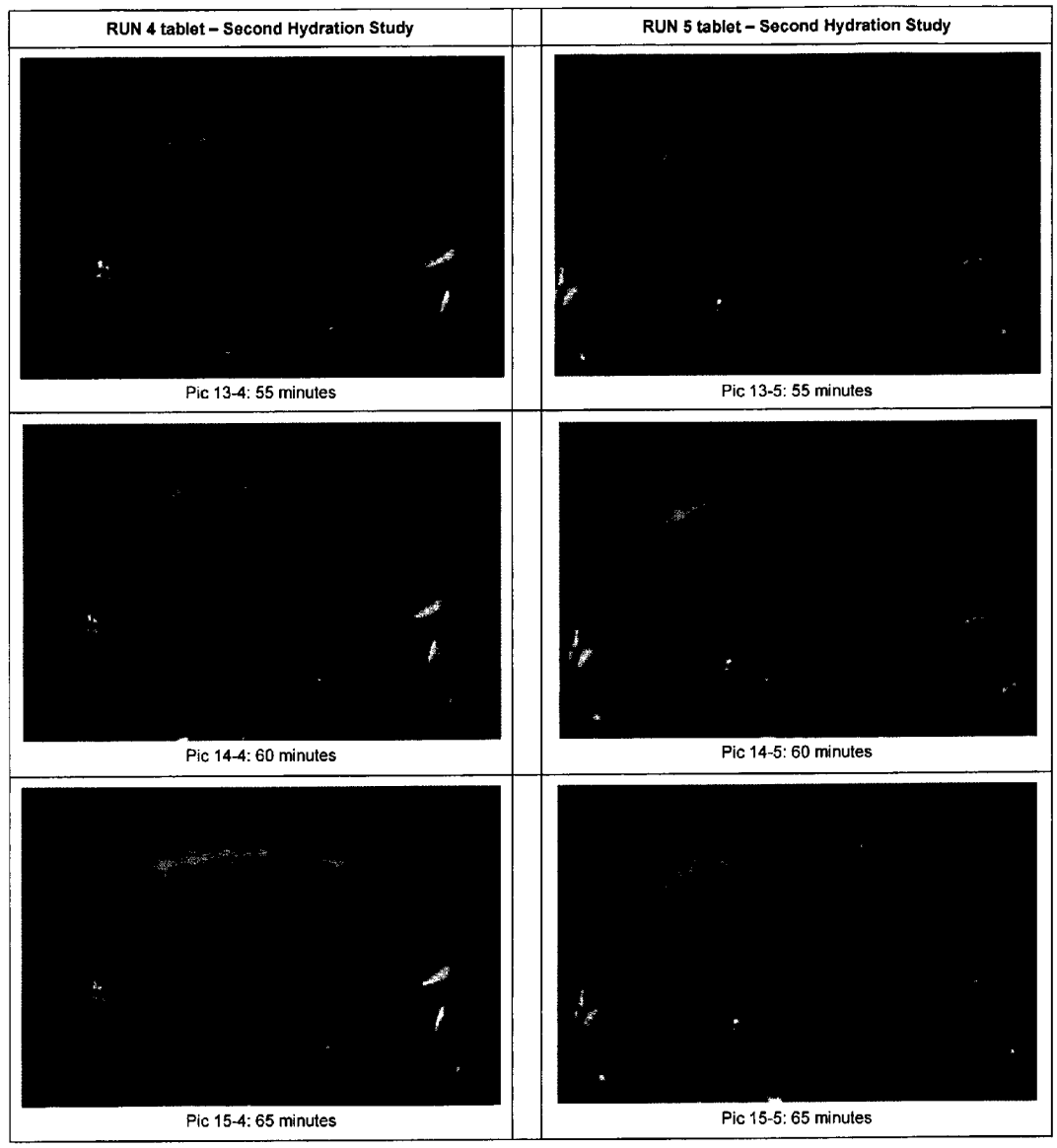
Figure 22F:
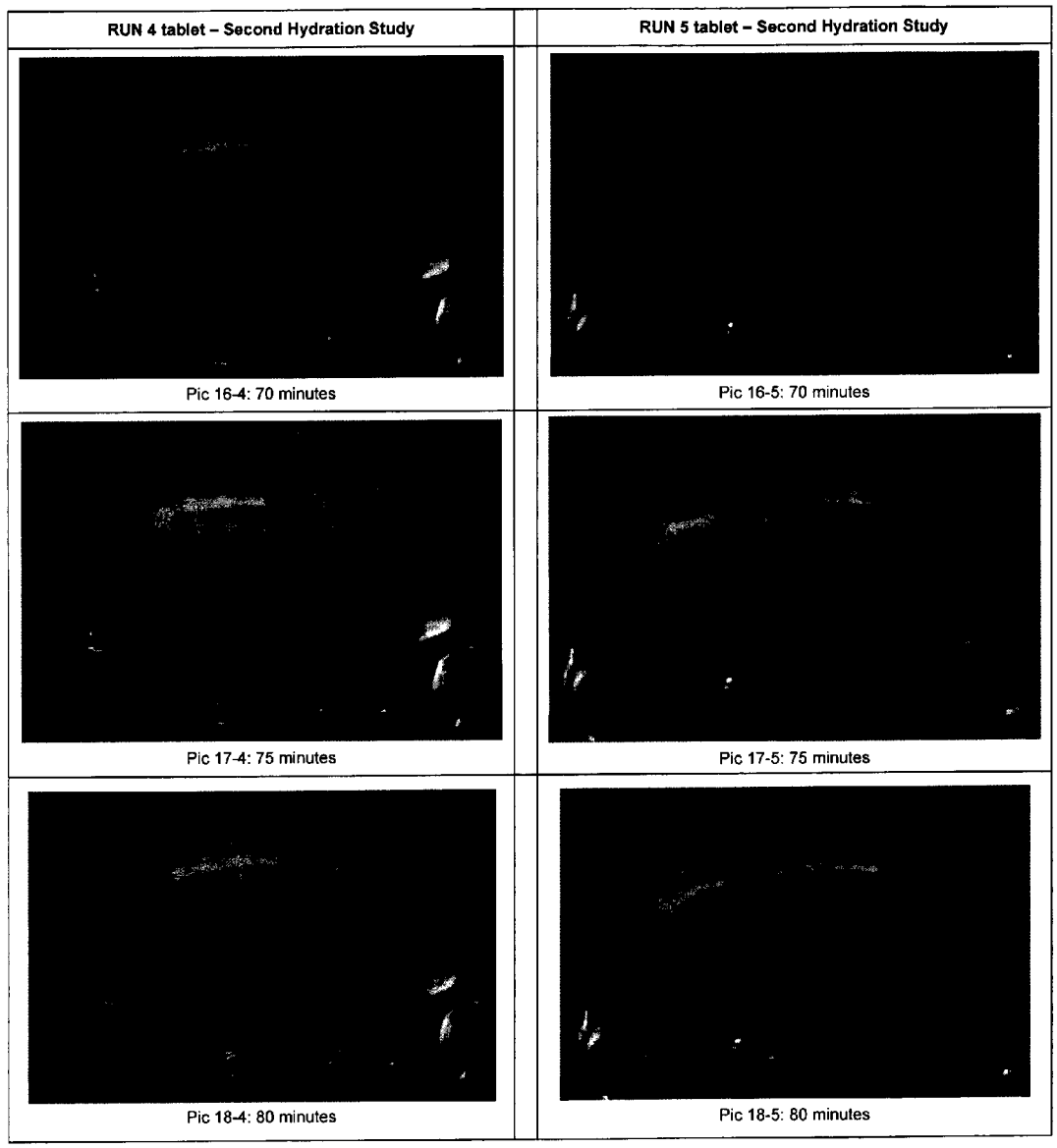
Figure 22G:
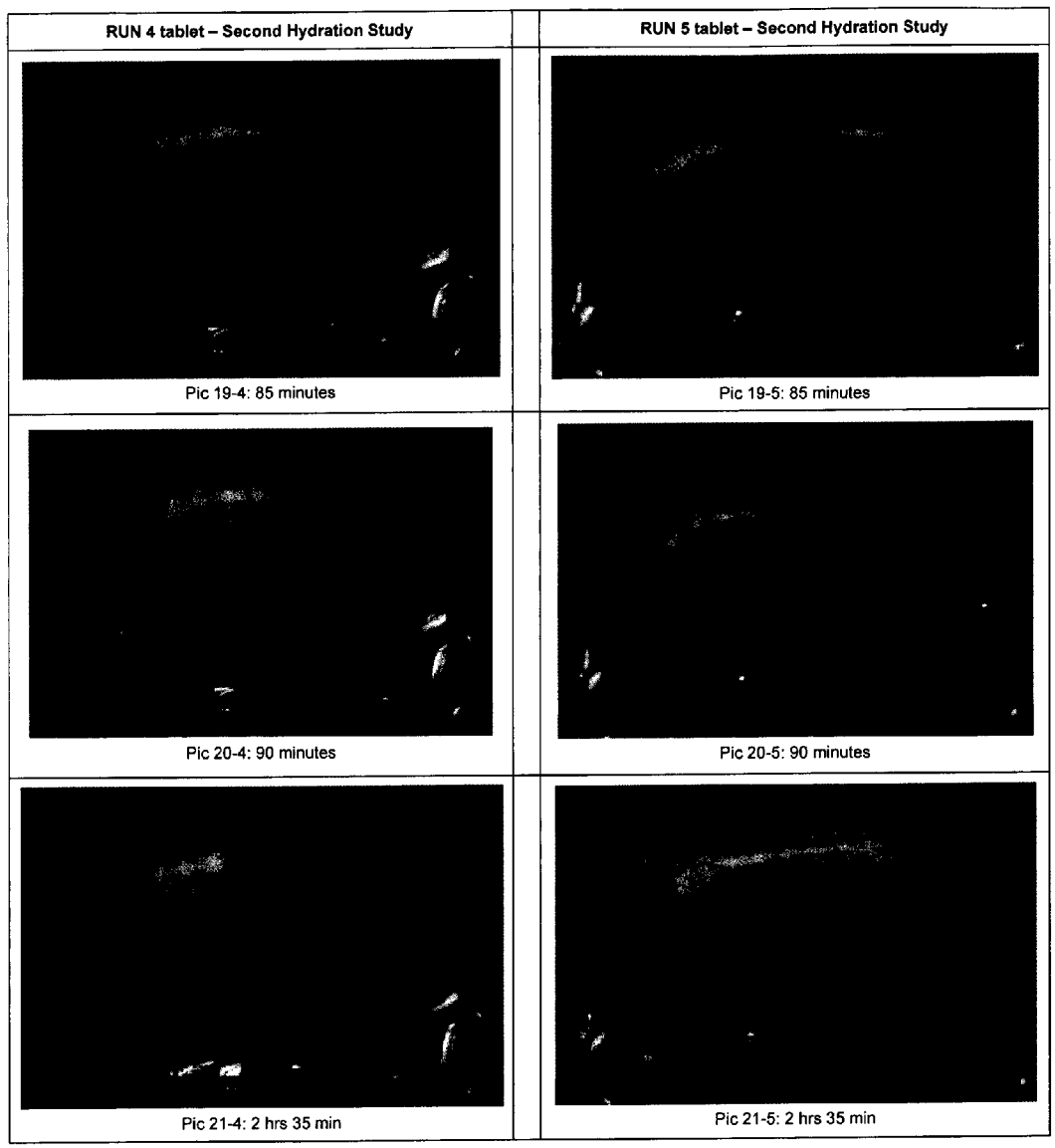
Figure 22H:
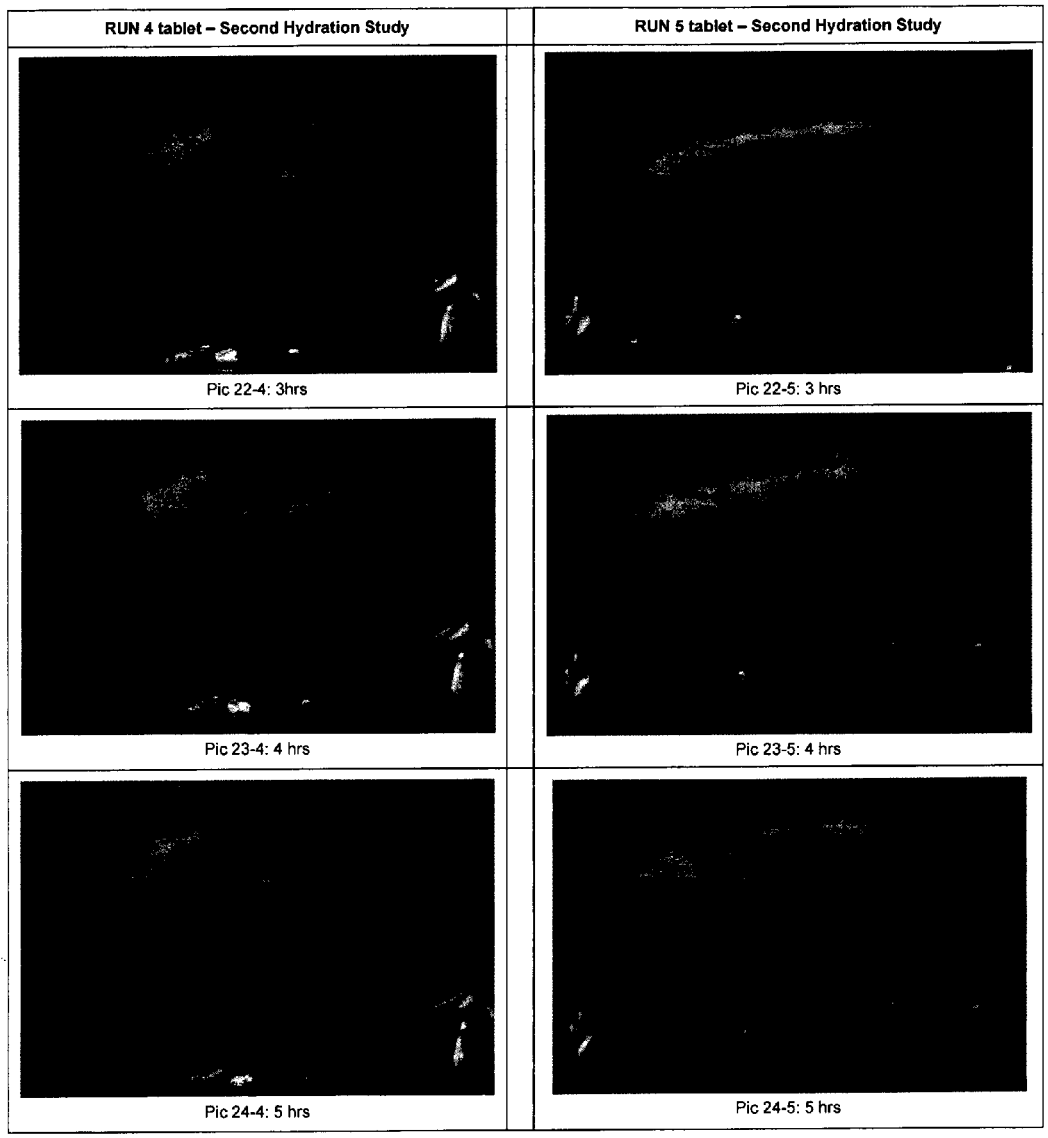
Figure 22I:
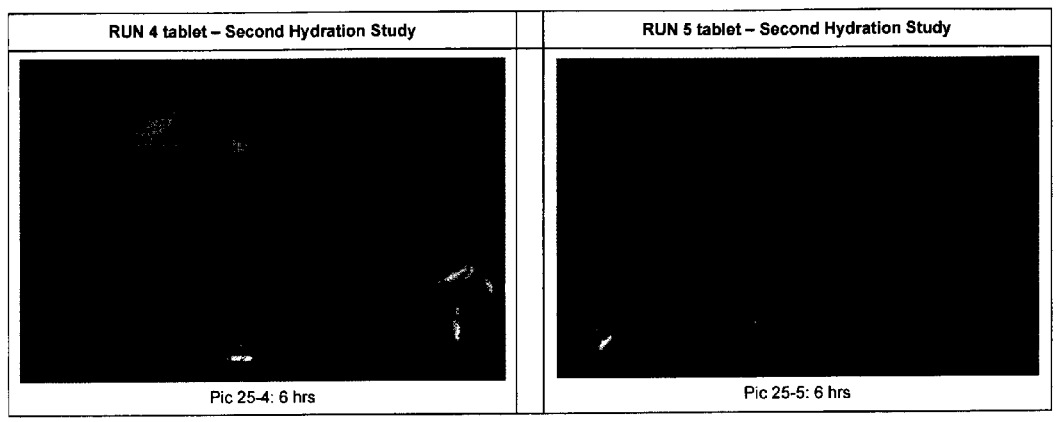

Photographs of the coated cured tablet cores of Run 4 taken in the first and second hydration studies five minutes after the coated cured tablet cores were placed in SGF show that the tablet cores' coatings preferentially ruptured and formed passageways immediately above or proximal to the groves, but were intact (with the exception of the cracks formed during curing along the tablet core's band) in the areas of the coatings distal to the groves or not immediately above the groves. These passageways are shown by black arrows in Pic 2-4 of FIG. 21A and Pic 2-4 of FIG. 22A. Pic 2-4 of FIG. 21A and Pic 2-4 of FIG. 22A show that the media was penetrating through these passageways. Pic 4-4 of FIG. 22B shows that the media continued selectively penetrating through these passageways ten minutes after the coated cured tablet core was placed in SGF. Red ovals in Pic 2-4 of FIG. 21A and Pic 2-4 of FIG. 22A show that the media was penetrating through the cracks formed in the tablet core's band during curing. Pic 6-4 of FIG. 22-B shows media penetration at a passageway formed on the tablet face of the coated cured tablet core of Run 4 twenty minutes after the coated cured tablet core was placed in SGF in the second hydration study.

The photograph of the coated cured tablet core of Run 5 taken in the first hydration study five minutes after the coated cured tablet core was placed in SGF show that the coating of this coated cured tablet core did not preferentially rupture and did not form passageways. With the exception of the cracks formed during curing along the tablet core's band, the coated cured tablet core remained intact five minutes after it was placed in SGF. Pic 2-5 of FIG. 21A shows that the media was penetrating through the cracks along the tablet core's band.

The photograph of the coated cured tablet core of Run 5 taken in the second hydration study five minutes after the coated cured tablet core was placed in SGF shows a passageway on the tablet core's face edge, and that the media is penetrating through this passageway. This rupture is shown by the red circle in Pic 3-5 of FIG. 22A. Pic 4-5 of FIG. 22B shows that the media continued penetration at the passageway on the tablet core's face edge ten minutes after the coated cured tablet core was placed in SGF, while the rest of the tablet core's face edge remained intact. Pic 3-5 also shows that the media was also penetrating through the cracks formed in the tablet core's band during curing. Pic 6-5 of FIG. 22B shows that the coated cured tablet core is hydrating and swelling through coating, and that the tablet core's face area remains intact twenty minutes after it was placed in SGF.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A controlled release dosage form comprising:
   a core comprising an active agent and having a surface with not substantially uniform topography comprising structures,
   the surface of the core coated with a coating comprising a controlled release material, the coating
   (i) completely covering the core and the structures, and
   (ii) having weak points in a portion of the coating immediately above the structures, such that the coating ruptures at the weak points at a predetermined time after the dosage form is placed in an aqueous medium to provide passageways in the portion of the coating immediately above the structures, wherein the active agent is then released from the dosage form substantially through the passageways at a predetermined rate for about 6 or more hours,
   wherein the structures are visibly discernable without the aid of any magnifying equipment and are selected from the group consisting of peaks, bumps, mounds, serrations, embossments, imprints, and combinations thereof, and
   the heights, widths, and/or depths of the structures are from about 1 millimeter to about 4 millimeters.

2. The controlled release dosage form of claim 1, wherein portions of the coating which are not immediately above the structures remain substantially intact and adhered to the core for about 8 to 36 hours after the dosage form is placed in the aqueous medium.

3. The dosage form of claim 1, wherein the controlled release material comprises a hydrophobic polymer.

4. The dosage form of claim 3, wherein the hydrophobic polymer is an acrylic polymer, an alkylcellulose or a mixture thereof.

5. The dosage form of claim 1, wherein the coating comprises from about 1% to about 5% of the dosage form by weight.

6. The dosage form of claim 1, wherein the coating adheres to the core until at least substantially all of the active agent is released from the dosage form through the passageways.

7. The dosage form according to claim 1, wherein the active agent is an opioid analgesic.

8. The dosage form according to claim 1, wherein the core comprises polyethylene oxide.

9. The dosage form of claim 8, wherein polyethylene oxide comprises from about 67% to 96% of the dosage form by weight.

10. The dosage form of claim 1, wherein the active agent comprises from about 4% to about 32% of the dosage form by weight.

11. The dosage form of claim 1, wherein the core consists essentially of the active agent, polyethylene oxide and a lubricant.

12. The dosage form of claim 1, which releases the active agent at substantially zero order release rate for about 0.5 to about 24 hours after the placement into the aqueous medium.

13. A method of controlling a rate of release of an active agent from a pharmaceutical dosage form, the dosage form comprising a substrate coated with a coating, the method comprising
   altering surface morphology of the substrate before the substrate is coated with the coating by creating a surface with a not substantially uniform topography comprising structures selected from the group consisting of peaks, bumps, mounds, serrations, embossments, imprints, and combinations thereof with heights, widths, and/or depths of from about 1 millimeter to about 4 millimeters on the surface of the substrate,
   coating the surface with a coating,
   wherein the structures are visibly discernable without the aid of any magnifying equipment of a height, width, shape and/or size which causes a rupture and formation of passageways in a portion of the coating immediately above the structures at a predetermined time after the dosage form is placed in an aqueous medium,
   and such that the active agent is released from the dosage form substantially through the passageways at a controlled rate for about 6 or more hours.

14. The method of claim 13, wherein the substrate is cured prior to being coated with the coating.

15. The method of claim 14, wherein the curing is at a temperature of about 46° C. to about 56° C. and for about 0.5 to 3 hours.

16. The dosage form of claim 1, wherein the structures are peaks.

17. The method of claim 13, wherein the structures are peaks.

18. The dosage form of claim 1, wherein the coating has the same thickness throughout.

19. The method of claim 13, wherein the coating has the same thickness throughout.

* * * * *